(12) United States Patent
Gianneschi et al.

(10) Patent No.: US 12,115,183 B2
(45) Date of Patent: *Oct. 15, 2024

(54) SYNTHETIC MELANIN NANOPARTICLES AND USES THEREOF

(71) Applicant: The Regents of the University of California, Oakland, CA (US)

(72) Inventors: Nathan C. Gianneschi, La Jolla, CA (US); Yuran Huang, La Jolla, CA (US); Yiwen Li, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 194 days.

This patent is subject to a terminal disclaimer.

(21) Appl. No.: 17/332,704

(22) Filed: May 27, 2021

(65) Prior Publication Data

US 2021/0393673 A1    Dec. 23, 2021

Related U.S. Application Data

(63) Continuation of application No. 16/317,003, filed as application No. PCT/US2017/041596 on Jul. 11, 2017, now Pat. No. 11,045,493.

(60) Provisional application No. 62/360,821, filed on Jul. 11, 2016.

(51) Int. Cl.
*A61K 31/787* (2006.01)
*A61K 9/51* (2006.01)

(52) U.S. Cl.
CPC ............ *A61K 31/787* (2013.01); *A61K 9/51* (2013.01)

(58) Field of Classification Search
CPC ................................ A61K 31/787; A61K 9/51
See application file for complete search history.

(56) References Cited

U.S. PATENT DOCUMENTS

| | | | |
|---|---|---|---|
| 4,861,760 | A | 8/1989 | Mazuel et al. |
| 4,911,920 | A | 3/1990 | Jani et al. |
| 5,212,162 | A | 5/1993 | Missel et al. |
| 5,403,841 | A | 4/1995 | Lang et al. |
| 5,441,542 | A | 8/1995 | Prota et al. |
| 5,547,658 | A | 8/1996 | Hansenne et al. |
| 8,067,044 | B2 | 11/2011 | Henry et al. |
| 8,586,090 | B2 | 11/2013 | Dadachova et al. |
| 11,045,493 | B2 | 6/2021 | Gianneschi et al. |
| 2009/0178209 | A1 | 7/2009 | Koike et al. |
| 2011/0020252 | A1* | 1/2011 | Shantha .................. A61K 8/44 424/59 |
| 2011/0236325 | A1 | 9/2011 | Mitchell et al. |
| 2013/0078205 | A1 | 3/2013 | Dayan et al. |
| 2013/0177616 | A1 | 7/2013 | de Olivera et al. |
| 2014/0044789 | A1* | 2/2014 | Dadachova .......... A61K 9/0019 514/224.5 |
| 2015/0093342 | A1 | 4/2015 | Domloge et al. |
| 2021/0393673 | A1 | 12/2021 | Gianneschi et al. |
| 2022/0332670 | A1 | 10/2022 | Zhou et al. |

FOREIGN PATENT DOCUMENTS

| | | |
|---|---|---|
| KR | 10-2016-0072590 | 6/2016 |
| WO | WO 1993/005759 | 4/1993 |
| WO | WO 2009/003037 | 12/2008 |
| WO | WO 2017/064672 | 4/2017 |
| WO | 2018/013609 A2 | 1/2018 |
| WO | 2021/021350 A2 | 2/2021 |
| WO | 2021/087076 A1 | 5/2021 |
| WO | 2021/096692 A1 | 5/2021 |

OTHER PUBLICATIONS

Apte, M et al. "Psychrotrophic yeast Yarrowia lipolytica NCYC 789 mediates the synthesis of antimicrobial silver nanoparticles via cell-associated melanin" AMB Express 2013, 3:32 (Year: 2013).*

Montefiori, D.C et al. "Inhibition of Human Immunodeficiency Virus Type 1 Replication and Cytopathicity by Synthetic Soluble Catecholamine Melanins In Vitro" Biochem. And Biophys. Res. Comm. 1990, 168 (1), 200-205 (Year: 1990).*

Akiladevi et al. (2010) "Ethosomes—A noninvasive approach for transdermal drug delivery," Int J Current Pharm Res 2(4): 1-4.

Alikhan et al. (2011) "Vitiligo: a comprehensive overview: part I. Introduction, epidemiology, quality of life, diagnosis, differential diagnosis, associations, histopathology, etiology, and work-up," J. Am. Acad. Dermatol. 65(3): 473-491.

Ando et al. (2007) "Approaches to identify inhibitors of melanin biosynthesis via the quality control of tyrosinase," J. Invest. Dermatol. 127(4): 751-761.

Ando et al. (2012) "Melanosomes are transferred from melanocytes to keratinocytes through the processes of packaging, release, uptake, and dispersion," J. Invest. Dermatol. 132(4): 1222-1229.

Apte et al. (2013) "Psychrotrophic yeast Yarrowia lipolytica NCYC 789 mediates the synthesis of antimicrobial silver nanoparticles via cell-associated melanin," AMB Express 3:32, pp. 1-8.

Beltran-Garcia et al. (2014) "Singlet Molecular Oxygen Generation by Light-Activated DHN-Melanin of the Fungal Pathogen Mycosphaerella fijiensis in Black Sigatoka Disease of Bananas," PLOS ONE 9(3): e91616, pp. 1-15.

Berge et al. (1977) "Pharmaceutical Salts," Journal of Pharmaceutical Sciences 66(1): 1-19.

Bernard et al. (publicly available Jan. 2016) "Consumption of hair dye products by the French women population: Usage pattern and exposure assessment," Food and Chemical Toxicology (Feb. 2016) 88: 123-132.

Bikle et al. (2012) "Calcium Regulation of Keratinocyte Differentiation," Expert Rev. Endocrinol. Metab. 7(4): 461-472.

(Continued)

*Primary Examiner* — Andrew S Rosenthal
(74) *Attorney, Agent, or Firm* — Leydig, Voit & Mayer, Ltd.

(57) ABSTRACT

Provided, inter alia, are synthetic melanin nanoparticles (MelNPs) useful for protecting keratinocytes from UV-damage and for treating melanin-defective diseases.

31 Claims, 19 Drawing Sheets

(56) References Cited

OTHER PUBLICATIONS

Borowska et al. (2015) "Metals in cosmetics: implications for human health," J Appl Toxicol 35(6): 551-572.
Boulton et al. (2001) "Retinal Photodamage," J. Photochem. Photobiol. B: Biol. 64(2-3): 144-161.
Brenner et al. (2008) "The Protective Role of Melanin Against UV Damage in Human Skin," Photochem. Photobiol. 84(3): 539-549.
Byers et al. (2003) "Role of Cytoplasmic Dynein in Perinuclear Aggregation of Phagocytosed Melanosomes and Supranuclear Melanin Cap Formation in Human Keratinocytes," J. Invest. Dermatol. 121(4): 813-820.
Byers et al. (2007) "Requirement of dynactin p150Glued subunit for the functional integrity of the keratinocyte microparasol," J. Investi. Dermatol. 127(7): 1736-1744.
Cecchini et al. (May 2017) "Modeling Fungal Melanin Buildup: Biomimetic Polymerization of 1,8-Dihydroxynaphthalene Mapped by Mass Spectrometry," Chem. Eur. J. 23: 8092-8098.
Chen et al. (2014) "Engineering fluorescent poly(dopamine) capsules," Langmuir 30(10): 2921-2925.
Chen et al. (Nov. 2016) "Nanoscale Polydopamine (PDA) Meets π-πInteractions: An Interface-Directed Coassembly Approach for Mesoporous Nanoparticles," Langmuir 32(46): 12119-12128.
Chonn et al. (1995) "Recent advances in liposomal drug-delivery systems," Curr. Opin. Biotechnol. 6(6): 698-708.
Dadachova et al. (2007) "Ionizing Radiation Changes the Electronic Properties of Melanin and Enhances the Growth of Melanized Fungi," Plos One 2(5): e457, pp. 1-13.
Dadachova et al. (2008) "Ionizing Radiation: How Fungi Cope, Adapt, and Exploit with the Help of Melanin," Curr. Opin. Microbiol. 11(6): 525-531.
Dadachova et al. (2008) "The radioprotective properties of fungal melanin are a function of its chemical composition, stable radical presence and spatial arrangement," Pigment Cell Melanoma Res 21(2): 192-199.
Dell'Angelica et al. (2000) "Lysosome-related organelles," FASEB J. 14(10): 1265-1278.
D'Ischia et al. (2015) "Melanins and Melanogenesis: from Pigment Cells to Human Health and Technological Applications," Pigm. Cell Melanoma Res. 28(5): 520-544.
Dolgova et al. (publicly available Jan. 2016) "Distribution of selenium in zebrafish larvae after exposure to organic and inorganic selenium forms," Metallomics (Mar. 2016) 8(3): 305-312.
Eisenman et al. (2005) "Microstructure of Cell Wall-Associated Melanin in the Human Pathogenic Fungus *Cryptococcus neoformans*," Biochemistry 44(10): 3683-3693.
Eyles et al. (1997) "Oral Delivery and Fate of Poly(lactic acid) Microsphere-encapsulated Interferon in Rats," J. Pharm. Pharmacol. 49(7): 669-674.
Fan et al. (2014) "Transferring biomarker into molecular probe: melanin nanoparticle as a naturally active platform for multimodality imaging," J. Am. Chem. Soc. 136(43): 15185-15194.
Gago-Dominguez et al. (2001) "Use of permanent hair dyes and bladder-cancer risk," Int J Cancer 91(4): 575-579.
Gao (1995) "Controlled Release of a Contraceptive Steroid from Biodegradable and Injectable Gel Formulations: In Vitro Evaluation," Pharm. Res. 12(6): 857-863.
Gao et al. (2013) "Mussel-Inspired Synthesis of Polydopamine-Functionalized Graphene Hydrogel as Reusable Adsorbents for Water Purification," ACS Applied Materials & Interfaces 5(2): 425-432.
Ghiani et al. (2008) "Characterization of human hair melanin and its degradation products by means of magnetic resonance techniques," Magn Reson Chem 46(5): 471-479.
Guerra-Tapia et al. (2014) "Hair cosmetics: dyes," Actas Dermo-Sifiliograficas 105(9): 833-839.
Haining et al. (Mar. 2017) "Neuromelanin, One of the Most Overlooked Molecules in Modern Medicine, is not a Spectator," Neural Regen. Res. 12(3): 372-375.
Hall et al. (Jul. 2016) "Protection against Radiotherapy-Induced Toxicity," Antioxidants (Basel) 5(3): 22, pp. 1-18.
Han et al. (Apr. 2015) "Dual-Stage-Light-Guided Tumor Inhibition by Mitochondria-Targeted Photodynamic Therapy," Adv. Funct. Mater. 25(20): 2961-2971.
Harrison et al. (2003) "Hair colouring, permanent styling and hair structure," J Cosmet Dermatol 2(3-4): 180-185.
Haveli et al. (2012) "Hair Fiber as a Nanoreactor in Controlled Synthesis of Fluorescent Gold Nanoparticles," Nano Lett 12(12): 6212-6217.
Hennessy et al. (2005) "Eumelanin and Pheomelanin Concentrations in Human Epidermis before and after UVB Irradiation," Pigm. Cell Res. 18(3): 220-223.
Hong et al. (2004) "Binding of Metal Ions to Melanin and Their Effects on the Aerobic Reactivity," Photochem. Photobiol. 80(3): 477-481.
Hong et al. (2007) "Current Understanding of the Binding Sites, Capacity, Affinity, and Biological Significance of Metals in Melanin," J. Phys. Chem. B 111(28): 7938-7947.
Huang et al. (publicly available May 2017) "Mimicking Melanosomes: Polydopamine Nanoparticles as Artificial Microparasols," and Suppl. Info., ACS Cent. Sci. (Jun. 2017) 3(6): 564-569 (22 pp. total).
Hunt et al. (1995) "Eumelanin and phaeomelanin contents of human epidermis and cultured melanocytes," Pigment Cell Res. 8(4): 202-208.
Im et al. (publicly available Feb. 2017) "Metal-Chelation-Assisted Deposition of Polydopamine on Human Hair: A Ready-to-Use Eumelanin-Based Hair Dyeing Methodology," Acs Biomater Sci Eng (Apr. 2017) 3(4): 628-636.
International Preliminary Report on Patentability, dated Jan. 24, 2019, corresponding to International Application No. PCT/US2017/041596 (filed Jul. 11, 2017), 10 pp.
Ito et al. (1980) "Co-polymerization of dopa and cysteinyldopa in melanogenesis in vitro," Experientia 36(7): 822-823.
Ito et al. (1985) "Microanalysis of eumelanin and pheomelanin in hair and melanomas by chemical degradation and liquid chromatography," Anal. Biochem. 144(2): 527-536.
Ito et al. (2003) "Quantitative analysis of eumelanin and pheomelanin in humans, mice, and other animals: a comparative review," Pigment Cell Res. 16(5): 523-531.
Ito et al. (2008) "Chemistry of Mixed Melanogenesis—Pivotal Roles of Dopaquinone," Photochem. Photobiol. 84(3): 582-592.
Iwamoto et al. (1999) "Different cell cycle mechanisms between UV-induced and X-ray-induced apoptosis in WiDr colorectal carcinoma cells," Apoptosis 4(1): 59-66.
Jin et al. (2012) "Genome-wide association analyses identify 13 new susceptibility loci for generalized vitiligo," Nat. Genet. 44(6): 676-680.
Johnson (Jul. 2017) Safety Assessment of Ammonia and Ammonium Hydroxide as Used in Cosmetics, Cosmetic Ingredient Review, 42 pages.
Ju et al. (2011) "Bioinspired polymerization of dopamine to generate melanin-like nanoparticles having an excellent free-radical-scavenging property," Biomacromolecules 12(3): 625-632.
Ju et al. (2013) "Bio-Inspired, Melanin-Like Nanoparticles as a Highly Efficient Contrast Agent for T1-Weighted Magnetic Resonance Imaging," Biomacromolecules 14(10): 3491-3497.
Ju et al. (publicly available Sep. 2014) "Bio-inspired Development of a Dual-Mode Nanoprobe for MRI and Raman Imaging," Small (Jan. 2015) 11(1): 84-89.
Kasraee et al. (2012) "Ebselen is a new skin depigmenting agent that inhibits melanin biosynthesis and melanosomal transfer," Exp. Dermatol. 21: 19-24.
Keogh et al. (1965) "Rate of Greying of Human Hair," Nature 207: 877-878.
Kim et al. (2010) "Biomimetic Approach to Confer Redox Activity to Thin Chitosan Films," Adv. Funct. Mater. 20(16): 2683-2694.
Kim et al. (2011) "Development of a high-content screening method for chemicals modulating DNA damage response," J. Biomol. Screen. 16(2): 259-265.
Kobayashi et al. (1993) "Melanin Reduces Ultraviolet-Induced DNA Damage Formation and Killing Rate in Cultured Human Melanoma Cells," J. Invest. Dermatol. 101(5): 685-689.

(56) References Cited

OTHER PUBLICATIONS

Kobayashi et al. (1998) "Supranuclear melanin caps reduce ultraviolet induced DNA photoproducts in human epidermis," J. Invest. Dermatol. 110(5): 806-810.

Kumar (2005) "Exploratory analysis of global cosmetic industry: major players, technology and market trends," Technovation 25(11): 1263-1272.

Kunwar et al. (2010) "In vivo radioprotection studies of 3,3'-diselenodipropionic acid, a selenocystine derivative," Free Radic Biol Med 48(3): 399-410.

Kunwar et al. (2011) " Anti-apoptotic, anti-inflammatory, and immunomodulatory activities of 3,3'-diselenodipropionic acid in mice exposed to whole body gamma-radiation," Arch Toxicol 85(11): 1395-1405.

Lampel et al. (Jun. 2017) "Polymeric Peptide Pigments with Sequence-Encoded Properties," Science 356(6342): 1064-1068.

Lee et al. (2007) "Mussel-Inspired Surface Chemistry for Multifunctional Coatings," Science 318(5849): 426-430.

Lee et al. (Feb. 2015) "Retinal development in albinism: a prospective study using optical coherence tomography in infants and young children," Lancet. 385(Suppl 1): p. S14.

Lent et al. (publicly available Nov. 2016) "Acute and subacute oral toxicity of periodate salts in rats," Regul Toxicol Pharmacol (Feb. 2017) 83: 23-37.

Li et al. (publicly available Dec. 2015) "Polycatechol Nanoparticle MRI Contrast Agents," Small (Feb. 2016) 12(5): 668-677.

Liebscher et al. (2013) "Structure of polydopamine: a never-ending story?" Langmuir 29(33): 10539-10548.

Lin et al. (publicly available Mar. 2016) "Multimodal-Imaging-Guided Cancer Phototherapy by Versatile Biomimetic Theranostics with UV and $\gamma$-Irradiation Protection," Adv Mater (May 2016) 28(17): 3273-3279.

Liu et al. (2004) "Ion-Exchange and Adsorption of Fe(III) by Sepia Melanin," Pigm. Cell Res. 17(3): 262-269.

Liu et al. (2013) "Mussel-Inspired Polydopamine: a Biocompatible and Ultrastable Coating for Nanoparticles in vivo," ACS Nano 7(10): 9384-9395.

Liu et al. (2014) "Polydopamine and its derivative materials: synthesis and promising applications in energy, environmental, and biomedical fields," Chem. Rev. 114(9): 5057-5115.

Liu et al. (publicly available Dec. 2016) "Comprehensive Insights into the Multi-Antioxidative Mechanisms of Melanin Nanoparticles and Their Application to Protect Brain from Injury in Ischemic Stroke," J. Am. Chem. Soc. (Jan. 2017) 139(2): 856-862.

Lusic et al. (2013) "X-ray-computed tomography contrast agents," Chem. Rev. 113(3): 1641-1666.

Ma et al. (2010) "Selenium-containing block copolymers and their oxidation- responsive aggregates," Polym. Chem. 1: 1609-1614.

MacLeod et al. (2015) "PEGylated N-Heterocyclic Carbene Anchors Designed to Stabilize Gold Nanoparticles in Biologically Relevant Media," J. Am. Chem. Soc. 137(25): 7974-7977.

Marks et al. (2001) "The melanosome: membrane dynamics in black and white," Nat. Rev. Mol. Cell Biol. 2: 738-748 (11 pages).

McFadden et al. (2007) "Allergy to hair dye—Its incidence is rising, as more and younger people dye their hair," Brit Med J 334: 220-220.

Meredith et al. (2006) "The physical and chemical properties of eumelanin," Pigment Cell Res. 19(6): 572-594.

Mironenko et al. (2000) "Intraspecific variation in gamma-radiation resistance and genomic structure in the filamentous fungus *Alternaria alternata:* a case study of strains inhabiting Chernobyl reactor No. 4," Ecotoxicol Environ Saf 45(2): 177-187.

Montoliu et al. (2014) "Increasing the complexity: new genes and new types of albinism," Pigment Cell Melanoma Res. 27(1): 11-18.

Morel et al. (2011) "Current Trends in the Chemistry of Permanent Hair Dyeing," Chem Rev 111(4): 2537-2561.

Mouret et al. (2006) "Cyclobutane pyrimidine dimers are predominant DNA lesions in whole human skin exposed to UVA radiation," Proc. Natl. Acad. Sci. 103(37): 13765-13770.

Mutsaers (2004) "The mesothelial cell," Int. J. Biochem. Cell Biol. 36(1): 9-16.

Nambiar et al. (2012) "Polymer-composite materials for radiation protection," ACS Appl Mater Interfaces 4(11): 5717-5726.

"NanoComposix's Guide to Dynamic Light Scattering Measurement and Analysis" [dated Feb. 2015 (version 1.4), published by nanoComposix of San Diego, CA, and available at nanoComposix_Guidelines_for_DLS_Measurements_and_Analysis (last accessed Jun. 26, 2019), pp. 1-8.

Napolitano et al. (2013) "Red Hair Benzothiazines and Benzothiazoles: Mutation-Inspired Chemistry in the Quest for Functionality," Acc. Chem. Res. 46(2): 519-528.

Nishimura et al. (2005) "Mechanisms of hair graying: Incomplete melanocyte stem cell maintenance in the niche," Science 307(5710): 720-724.

Nosanchuk et al. (2003) "The Contribution of Melanin to Microbial Pathogenesis," Cell. Microbiol. 5(4): 203-223.

Nosanchuk et al. (2015) "Fungal Melanin: What do We Know About Structure?" Front. Microbiol. 6, 1463: pp. 1-7.

Ochs et al. (2011) "Dopamine-mediated continuous assembly of biodegradable capsules," Chem. Mater. 23(13): 3141-3143.

Orlow (1995) "Melanosomes are specialized members of the lysosomal lineage of organelles," J. Invest. Dermatol. 105(1): 3-7.

Pacelli et al. (publicly available Jan. 2017) "Melanin is Effective in Protecting Fast and Slow Growing Fungi from Various Types of Ionizing Radiation," Environ. Microbiol. (Apr. 2017) 19(4): 1612-1624.

Park et al. (publicly available Nov. 2016) "Novel Neuroprotective Effects of Melanin-Concentrating Hormone in Parkinson's Disease," Mol. Neurobiol. (Dec. 2017) 54: 7706-7721.

Patel et al. (2013) "Trends in use of hair dye: a cross-sectional study," Int J Trichology 5(3): 140-143, 9 pages.

Pezzella et al. (1997) "Identification of Partially Degraded Oligomers of 5, 6-Dihydroxyindole-2-carboxylic Acid in Sepia Melanin by Matrix-assisted Laser Desorption/Ionization Mass Spectrometry," Rapid Commun. Mass Spectrom. 11(4): 368-372.

Pihet et al. (2009) "Melanin is an Essential Component for the Integrity of the Cell Wall of Aspergillus Fumigatus Conidia," BMC Microbiol. 9: 177, pp. 1-11.

Pyo et al. (publicly available Apr. 2016) "Artificial pheomelanin nanoparticles and their photo-sensitization properties," J Photochem Photobiol B (Jul. 2016) 160: 330-335.

Raposo et al. (2007) "Melanosomes—dark organelles enlighten endosomal membrane transport," Nat. Rev. Mol. Cell Biol. 8(10): 786-797.

Ricci et al. (Nov. 2016) "Drug-induced hair colour changes," Eur J Dermatol 26(6): 531-536.

RILEY (1997) "Melanin," Int J Biochem Cell B 29(11): 1235-1239.

Robertson et al. (2012) "Adaptation of the Black Yeast *Wangiella dermatitidis* to Ionizing Radiation: Molecular and Cellular Mechanisms," Plos One 7(11): e48674, pp. 1-18.

Rouse et al. (2007) "Effects of Mechanical Flexion on the Penetration of Fullerene Amino Acid-Derivatized Peptide Nanoparticles through Skin," Nano Letters 7(1): 155-160.

Schmaler-Ripcke et al. (2009) "Production of Pyomelanin, a Second Type of Melanin, via the Tyrosine Degradation Pathway in Aspergillus fumigatus," Appl. Environ. Microbiol. 75(2): 493-503.

Schweitzer et al. (2009) "Physico-Chemical Evaluation of Rationally Designed Melanins as Novel Nature-Inspired Radioprotectors," PLOS ONE 4(9): e7229, pp. 1-8.

Schweitzer et al. (2010) "Melanin-Covered Nanoparticles for Protection of Bone Marrow during Radiation Therapy of Cancer," Int. J. Radiat. Oncol. Biol. Phys. 78(5): 1494-1502.

Scott et al. (2002) "Filopodia are conduits for melanosome transfer to keratinocytes," J. Cell Sci. 115(7): 1441-1451.

Seagle et al. (2005) "Melanin photoprotection in the human retinal pigment epithelium and its correlation with light-induced cell apoptosis," Proceedings of the National Academy of Sciences of the United States of America 102(25): 8978- 8983.

Seagle et al. (2005) "Time-Resolved Detection of Melanin Free Radicals Quenching Reactive Oxygen Species," J. Am. Chem. Soc. 127(32): 11220-11221.

(56) References Cited

OTHER PUBLICATIONS

Search Report and Written Opinion, dated Feb. 26, 2021, corresponding to International Patent Application No. PCT/US2020/039769, 13 pages.
Search Report and Written Opinion, dated Jan. 26, 2021, corresponding to International Patent Application No. PCT/US2020/057902, 11 pages.
Search Report and Written Opinion, dated Jan. 30, 2018, corresponding to International Application No. PCT/US2017/041596 (filed Jul. 11, 2017), 12pp.
Search Report and Written Opinion, dated Mar. 4, 2021, corresponding to International Patent Application No. PCT/US2020/057939, 16 pages.
Seo et al. (2012) "Hydrogen peroxide and monoethanolamine are the key causative ingredients for hair dye-induced dermatitis and hair loss," J Dermatol Sci 66(1): 12-19.
Simon et al. (2010) "The Red and the Black," Acc. Chem. Res. 43(11): 1452-1460.
Sing et al. (1985) "Reporting physisorption data for gas/solid systems with special reference to the determination of surface area and porosity," Pure Appl. Chem. 57(4): 603-619.
Solano (2014) "Melanins: Skin Pigments and Much More-Types, Structural Models, Biological Functions, and Formation Routes," New J. Sci. 2014, 498276: 1-28.
Solano (publicly available Apr. 2016) "Photoprotection versus photodamage: updating an old but still unsolved controversy about melanin," Polym. Int. (Nov. 2016) 65(11): 1276-1287.
Song et al. (2007) "Supramolecular Nanofibers by Self-Organization of Bola-amphiphiles through a Combination of Hydrogen Bonding and π-π Stacking Interactions," Adv. Mater. 19(3): 416-420.
Sosted et al. (2005) "Contact dermatitis to hair dyes in a Danish adult population: an interview-based study," Brit J Dermatol 153(1): 132-135.
Steinmann et al. (2010) "Selenium and sulfur in exchange reactions: a comparative study," J Org Chem 75(19): 6696-6699.
Strube et al. (Mar. 2015) "Site-Specific In Situ Synthesis of Eumelanin Nanoparticles by an Enzymatic Autodeposition-like Process," Biomacromolecules. 16(5): 1608-1613.
Tada et al. (2010) "Scavenging or Quenching Effect of Melanin on Superoxide Anion and Singlet Oxygen," J. Clin. Biochem. Nutr. 46(3): 224-228.
Tadokoro et al. (2003) "UV-induced DNA damage and melanin content in human skin differing in racial/ethnic origin," FASEB J. 17(9): 1177-1179.
Takkouche et al. (2005) "Personal use of hair dyes and risk of cancer—A meta-analysis," JAMA—J Am Med Assoc 293(20): 2516-2525.
THOMSON (1974) "The Pigments of Reddish Hair and Feathers," Angew. Chem., Int. Ed. 13(5): 305-312.
Tokura et al. (2018) "Fabrication of Defined Polydopamine Nanostructures by DNA Origami-Templated Polymerization," Angew. Chem. Int. Ed. Engl. 57: 1587-1591.
Tran et al. (2006) "Chemical and structural disorder in eumelanins: a possible explanation for broadband absorbance," Biophys. J. 90(3): 743-752.
Van Neste et al. (2004) "Hair cycle and hair pigmentation: dynamic interactions and changes associated with aging," Micron 35(3): 193-200.
Velasco et al. (2009) "Hair fiber characteristics and methods to evaluate hair physical and mechanical properties," Braz J Pharm Sci 45(1): 153-162.
Vliegenthart et al. (2011) "Compression, crumpling and collapse of spherical shells and capsules," New J. Phys. 13: 045020, pp. 1-24.
Wakamatsu et al. (2003) "The Structure of Neuromelanin as Studied by Chemical Degradative Methods," J. Neurochem. 86(4): 1015-1023.
Walter et al. (2006) "Early use of PbS nanotechnology for an ancient hair dyeing formula," Nano Lett 6(10): 2215-2219.
Wang et al. (2018) "Skin Pigmentation-Inspired Polydopamine Sunscreens," Adv. Funct. Mater. 28: 1802127: 1-9.
Wang et al. (publicly available Sep. 2017) "A Novel UV-Shielding and Transparent Polymer Film: When Bioinspired Dopamine-Melanin Hollow Nanoparticles Join Polymers," Acs Appl Mater Inter (Oct. 2017) 9(41): 36281-36289.
Wang et al. (publicly available Sep. 2017) "Tunable, Metal-Loaded Polydopamine Nanoparticles Analyzed by Magnetometry," Chem. Mater. (Oct. 2017) 29(19): 8195-8201.
Watt et al. (2009) "The supramolecular structure of melanin," Soft Matter 5(19): 3754-3760.
Wogelius et al. (2011) "Trace metals as biomarkers for eumelanin pigment in the fossil record," Science 333(6049): 1622-1626.
Wu et al. (2012) "Melanoregulin regulates a shedding mechanism that drives melanosome transfer from melanocytes to keratinocytes," Proc. Natl. Acad. Sci. 109(31): E2101-E2109.
Xiao et al. (May 2015) "Bio-Inspired Structural Colors Produced via Self-Assembly of Synthetic Melanin Nanoparticles," ACS nano 9(5): 5454-5460.
Xu et al. (2013) "Selenium-Containing Polymers: Promising Biomaterials for Controlled Release and Enzyme Mimics," Acc. Chem. Res. 46(7): 1647-1658.
Yi et al. (Jul. 2017) "Liquid-immune structural colors with angle-independence inspired from hollow melanosomes," Chem Commun 53(66): 9234-9237.
Yu et al. (2014) "Formation of polydopamine nanofibers with the aid of folic acid," Angew. Chem. Int. Ed. 53(46): 12600-12604.
Zhang et al. (2012) "Biocompatible Polydopamine Fluorescent Organic Nanoparticles: Facile Preparation and Cell Imaging," Nanoscale 4(18): 5581-5584.
Zhang et al. (publicly available Jan. 2016) "CuSO4/H2O2-Induced Rapid Deposition of Polydopamine Coatings with High Uniformity and Enhanced Stability," Angew Chem Int Ed Engl (Feb. 2016) 55(9): 3054-3057.
Zhou et al. (2014) "Rapidly-Deposited Polydopamine Coating via High Temperature and Vigorous Stirring: Formation, Characterization and Biofunctional Evaluation," Plos One 9(11): e113087, pp. 1-10.
Zucca et al. (2014) "Neuromelanin of the human substantia nigra: an update," Neurotox. Res. 25: 13-23.
Abcam Flow cytometric analysis of cell cycle with propidium iodide DNA staining. https://www.abcam.com/protocols/flow-cytometric-analysis-of-cell-cycle-with-propidium-iodide-dna-staining.
Al-Muhammed et al. (1996) "In-vivo studies on dexamethasone sodium phosphate liposomes," J. Microencapsul. 13(3): 293-306.
Bardestani et al. (2019) "Experimental methods in chemical engineering: specific surface area and pore size distribution measurements-BET, BJH, and DFT," The Canadian Journal of Chemical Engineering 97(11): 2781-2791.
Battistella et al. (2020) "Mimicking Natural Human Hair Pigmentation with Synthetic Melanin," ACS Cent. Sci. 6(7): 1179-1188.
Chung (Sep. 2016) "Azo dyes and human health: A review," J Environ Sci Health C Environ Carcinog Ecotoxicol Rev 34: 233-261.
Cordero et al. (2020) "Melanin." Curr Biol 30 (4), R142-R143.
D'Alba et al. (2019) "Melanosomes: Biogenesis, Properties, and Evolution of an Ancient Organelle," Physiol. Rev. 99: 1-19.
Dong et al. (2019) "Melanin-mimetic multicolor and low-toxicity hair dye," RSC Adv 9: 33617.
Etebari et al. (2015) "Evaluation of protective effect of amifostine on dacarbazine induced genotoxicity" Res Pharm Sci 10, (1), 68-74.
Foote et al. (1996) Active Oxygen in Chemistry (Book).
Gao et al. (2019) "Rapid preparation of polydopamine coating as a multifunctional hair dye," Rsc Adv 9: 20492-20496.
Glass et al. (2012) "Direct chemical evidence for eumelanin pigment from the Jurassic period" Proc. Natl. Acad. Sci. U. S. A. 109, (26), 10218-23.
Hasegawa et al. (2015) "Health effects of radiation and other health problems in the aftermath of nuclear accidents, with an emphasis on Fukushima." Lancet 386, (9992), 479-488.

(56) References Cited

OTHER PUBLICATIONS

Huang et al. (2018) "Recent Advances and Progress on Melanin-like Materials and Their Biomedical Applications," Biomacromolecules 19: 1858-1868.
Ito S. (1989) "Optimization of conditions for preparing synthetic pheomelanin." Pigment Cell Res 2, (1), 53-6.
Kang et al. (2018) "Reverse Engineering To Characterize Redox Properties: Revealing Melanin's Redox Activity through Mediated Electrochemical Probing," Chem. Mater. 30: 5814-5826.
Kawamura et al. (2016) "Full-Color Biomimetic Photonic Materials with Iridescent and Non-Iridescent Structural Colors." Sci Rep 6, 33984.
Kim et al. (2018) "Enzymatic film formation of nature-derived phenolic amines" Nanoscale 10 (28), 13351-13355.
Kim et al. (2017) "Spectroelectrochemical Reverse Engineering Demonstrates That Melanin's Redox and Radical Scavenging Activities Are Linked," Biomacromolecules 18(12): 4084-4098.
Korner et al. (1982) "Mammalian tyrosinase catalyzes three reactions in the biosynthesis of melanin," Science 217(4565): 1163-1165.
Lee et al. (2007) "A reversible wet/dry adhesive inspired by mussels and geckos." Nature 448, (7151), 338-41.
Lemaster et al. (2019) "Gadolinium Doping Enhances the Photoacoustic Signal of Synthetic Melanin Nanoparticles: A Dual Modality Contrast Agent for Stem Cell Imaging," Chem. Mater. 31(1): 251-259.
Liu et al. (2003) "Comparison of the Structural and Physical Properties of Human Hair Eumelanin Following Enzymatic or Acid/Base Extraction." Pigment Cell Res. 16, (4), 355-365.
Liu et al. (2019) "Role of Polydopamine's Redox-activity on Its Pro-oxidant, Radical-scavenging, and Antimicrobial Activities," Acta Biomater. 88: 181-196.
Luo et al. (2018) "Multifunctional Graphene Hair Dye," Chem-US 4: 784-794.
Maia et al. (2013) "Key ornamental innovations facilitate diversification in an avian radiation." Proc. Natl. Acad. Sci. U. S. A. 110, (26), 10687-10692.
Manini et al. (2018) "Characterization and Fate of Hydrogen-Bonded Free-Radical Intermediates and Their Coupling Products from the Hydrogen Atom Transfer Agent 1,8-Naphthalenediol," ACS Omega 3: 3918-3927.
Manini et al. (2019) "A Robust Fungal Allomelanin Mimic: An Antioxidant and Potent pi-Electron Donor with Free-Radical Properties that can be Tuned by Ionic Liquids," Chempluschem 84(9): 1331-1337.
Manini et al. (2020) "Synthetic mycomelanin thin films as emergent bio-inspired interfaces controlling the fate of embryonic stem cells," J Mater Chem B 8(20): 4412-4418.
Martinez et al. (2019) "Production of Melanins With Recombinant Microorganisms" Front Bioeng Biotechnol 7, 285.
Mbonyiryivuze et al. (2015) "Fourier Transform Infrared Spectroscopy for Sepia Melanin" Phys. Mater. Chem. 3, (2), 25-29.
Mostert et al. (2018) "The photoreactive free radical in eumelanin," Science Advances 4(3).
Ni et al. (2020) "Chemoenzymatic elaboration of the Raper-Mason pathway unravels the structural diversity within eumelanin pigments" Chem Sci 11, 7836-7841.
Panzella et al. (2013) "Atypical structural and pi-electron features of a melanin polymer that lead to superior free-radical-scavenging properties." Angew. Chem. Int. Ed. 2013, 52, (48), 12684-7.
Premi et al. (2015) "Chemiexcitation of melanin derivatives induces DNA photoproducts long after UV exposure" Science 347, (6224), 842-847.
Prota, G. (2000) "Melanins, melanogenesis and melanocytes: looking at their functional significance from the chemist's viewpoint" Pigment Cell Res 13 (4), 283-93.
Qstio, Am. J Hasp. Pharm. 46: 1576-1587, 1989.
Rao (1995) "Recent developments of collagen-based materials for medical applications and drug delivery systems," J Biomater Sci. Polym. Ed 7(7): 623-645.
Ren et al. (2013) "High level production of tyrosinase in recombinant Escherichia coli" BMC Biotechnol 13, 18.
Ryu et al. (2018) "Polydopamine Surface Chemistry: A Decade of Discovery," ACS Appl Mater Interfaces 10(9): 7523-7540.
Sealy et al. (1982) "Eumelanins and pheomelanins: characterization by electron spin resonance spectroscopy," Science 217(4559): 545-547—Abstract Only.
Seo et al. (2003) "Mushroom tyrosinase: Recent prospects" J Agr Food Chem 51 (10), 2837-2853.
Smyth et al. (1951) "A study of pigments from red, brown, and buff feathers and hair." Physiol Zool 24, (3), 205-16.
Sun et al. (2019) "Melanin-dot-mediated delivery of metallacycle for NIR-II/photoacoustic dual-modal imaging-guided chemo-photothermal synergistic therapy," Proc Natl Acad Sci USA 116(34): 16729-16735.
Taieb et al. (2011) "Melanins and Melanosomes: Biosynthesis, Biogenesis, Physiological, and Pathological Functions," Wiley-VCR Verlag Gmbh & Co., Weinheim.
Thureau et al. (2012) "Probing the motional behavior of eumelanin and pheomelanin with solid-state NMR spectroscopy: new insights into the pigment properties." Chem.: Eur. J. 18, (34), 10689-700.
Wang et al. (2019) "Characterization and application of melanin produced by the fast-growing marine bacterium Vibrio natriegens through heterologous biosynthesis." Appl Environ Microbiol DOI: 10.1128/AEM.02749-19.
Xiao et al. (2017) "Bioinspired Bright Noniridescent Photonic Melanin Supraballs," Sci. Adv. 3(9): e1701151.
Zaidi et al. (2014) "Purification and characterization of melanogenic enzyme tyrosinase from button mushroom" Enzyme Res 120739.
Zanoni et al. (2018) "Allergens of permanent hair dyes induces epidermal damage, skin barrier loss and IL-1 alpha increase in epidermal in vitro model," Food Chem Toxicol 112: 265-272.
Zhou et al. (2019) "Artificial Allomelanin Nanoparticles," ACS Nano 13(10): 10980-10990.
Zhu et al. (2018) "A rapid deposition of polydopamine coatings induced by iron (III) chloride/hydrogen peroxide for loose nanofiltration," J Colloid Interf Sci 523: 86-97.

\* cited by examiner

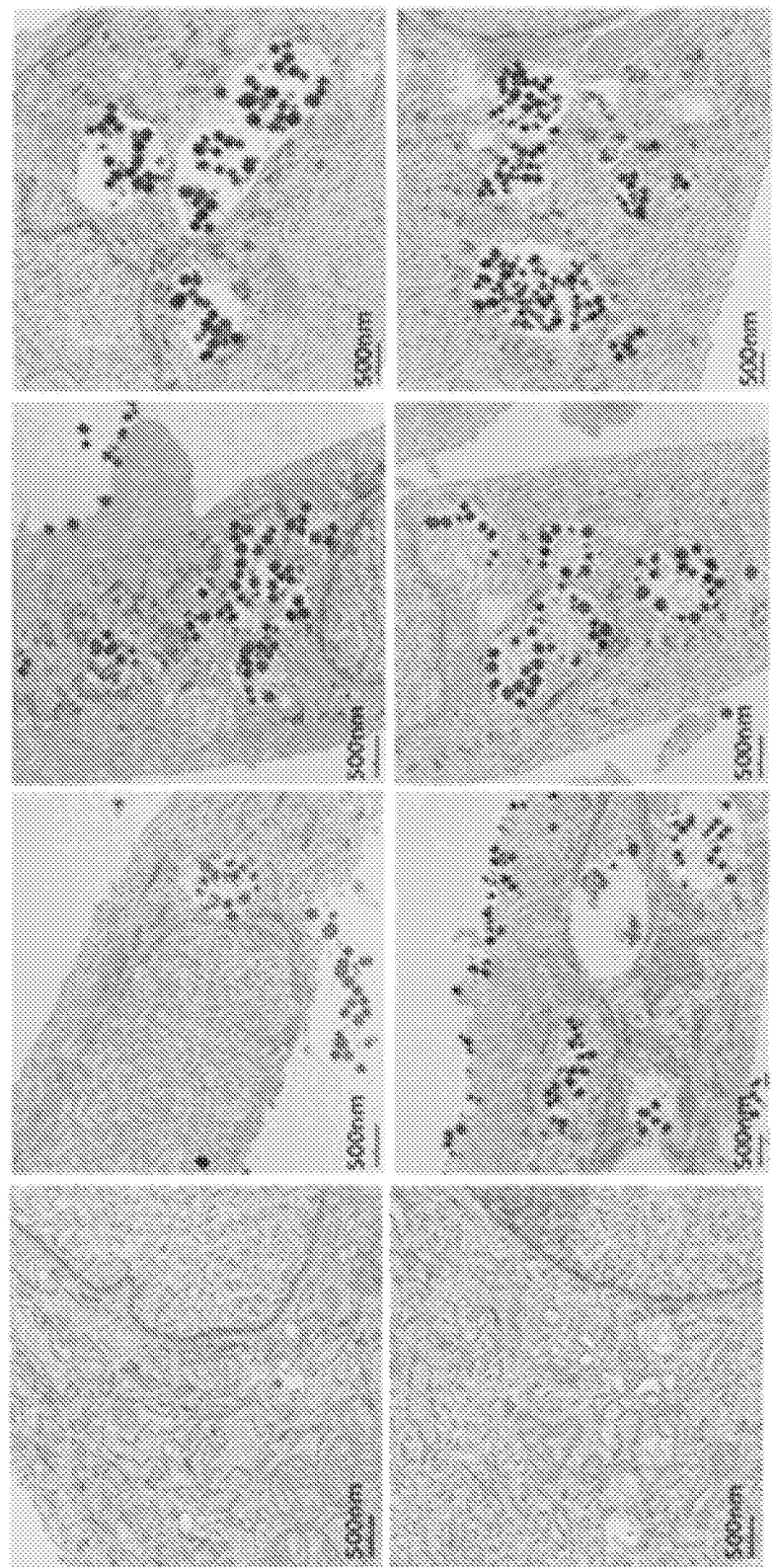

SYNTHETIC MELANIN NANOPARTICLES AND USES THEREOF

CROSS-REFERENCE TO RELATED APPLICATIONS

This application is a continuation application of U.S. application Ser. No. 16/317,003, filed Jan. 10, 2019, which is a U.S. National Stage Application of International Application No. PCT/US2017/041596, filed Jul. 11, 2017; which claims the benefit of and priority to U.S. Provisional Application No. 62/360,821 filed Jul. 11, 2016. The disclosures of each of the prior applications is incorporated herein in their entireties for all purposes.

STATEMENT AS TO RIGHTS TO INVENTIONS MADE UNDER FEDERALLY SPONSORED RESEARCH OR DEVELOPMENT

This invention was made with Government support under grant number FA9550-11-1-0105 awarded by the Air Force Office of Scientific Research. The Government has certain rights in this invention.

BACKGROUND

A role of melanin in skin cells is, inter alia, the prevention of UV-induced nuclear DNA damage. Melanin is delivered to keratinocytes in the skin after being excreted as melanosomes from melanocytes. Defects in melanin production in humans can cause diseases, many of which currently lack effective treatments due to their genetic origins (e.g. skin cancer, vitiligo and albinism). The widespread prevalence of melanin-related diseases and an increasing interest in the performance of various polymeric materials related to melanin necessitates novel synthetic routes for preparing melanin-like materials and use thereof. Accordingly, the present disclosure provides solutions to these and other problems in the art.

SUMMARY

In an aspect, a method for protecting a cell from ultraviolet (UV) damage is provided, the method comprising contacting a cell with a synthetic melanin nanoparticle, the synthetic melanin nanoparticle comprising one or more melanin polymers, wherein the synthetic melanin nanoparticle is capable of functioning as a pigment for the protection of the cell from UV damage In another aspect, a method for treating a melanin-defective disease in a subject in need thereof is provided, the method comprising administering to the subject a synthetic melanin nanoparticle, the synthetic melanin nanoparticle comprising one or more melanin polymers, wherein the synthetic melanin nanoparticle is capable of protecting the subject from UV damage.

In another aspect, a pharmaceutical composition comprising a synthetic melanin nanoparticle and one or more pharmaceutically acceptable excipients is provided, the synthetic melanin nanoparticle comprising one or more melanin polymers.

BRIEF DESCRIPTION OF THE DRAWINGS

FIG. 1A: Synthetic scheme for the preparation of MelNPs; FIG. 1B: UV-vis spectrum for an aqueous solution of MelNPs and photograph of a vial containing a sample at 10 mg/ml; FIG. 1C: TEM image and FIG. 1D: SEM image of MelNPs.

FIG. 2A: TEM images for HEKa cells incubated with 0.02 mg/ml MelNPs for 4 hours, 1 day, and 3 days: MelNPs were taken up by HEKa cells and transported to the perinuclear area to form supranuclear caps. FIG. 2B: Confocal Laser Scanning Microscopy images for co-localization of MelNPs and lysosomes in HEKa cells. Nuclei of HEKa cells were stained by Hoechst 33342 (blue); lysosomes were stained by LYSOTRACKER® Red DND-99; MelNPs were black in HEKa cells under bright field microscopy (indicated with arrows); the co-localization of bright-field, black MelNPs and red fluorescence for labeled lysosomes are indicated with yellow arrows. Scale bars are 10 μm. FIG. 2C: Scheme for the uptake, transportation and accumulation of MelNPs in HEKa cells. FIG. 2D: Magnification of TEM image for HEKa cells incubated with 0.02 mg/ml MelNPs for 3 days. Melanosomes are indicated with black arrows, and keratin fibers indicated with black arrowheads.

FIG. 3A: DNA damage evaluated by light microscopy for HEKa cells with/without incubation with MelNPs. Nuclei were stained by Hochest 33342 and indicated as blue; Cell membranes were stained by Image-iT DEAD Green and showed as green. Scale bars are 80 μm. FIG. 3B: Crystal violet assay for HEKa cell viability with/without UV or/and MelNP treatment. * $p<0.05$.

FIGS. 5A-5D. Stained TEM images for HEKa cells incubated with different concentrations of MelNPs for 4 hours. FIG. 5A: 0 mg/ml; FIG. 5B: 0.4 mg/ml; FIG. 5C: 0.1 mg/ml; FIG. 5D: 0.02 mg/ml.

FIG. 10A: TEM images of AuNPs with diameters around 150 nm; FIG. 10B: Zeta-potentials of MelNPs and AuNPs: FIG. 10C: DLS measurement of AuNPs (average diameter=180 nm).

DETAILED DESCRIPTION

Definitions

Figure 1A:
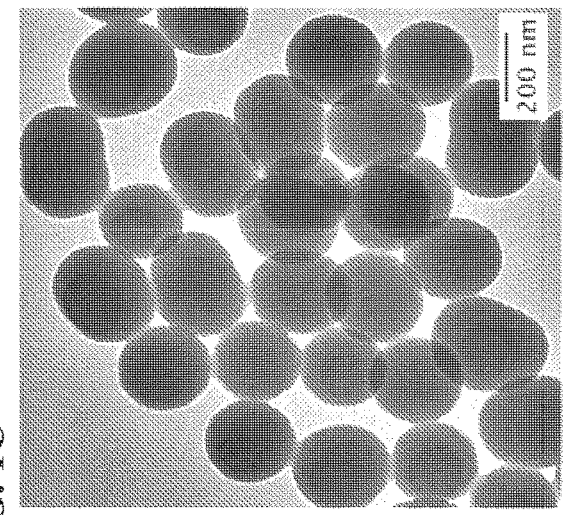
FIGS. 1A-1D. Synthesis and characterization of synthetic melanosomes.
Figure 1C:
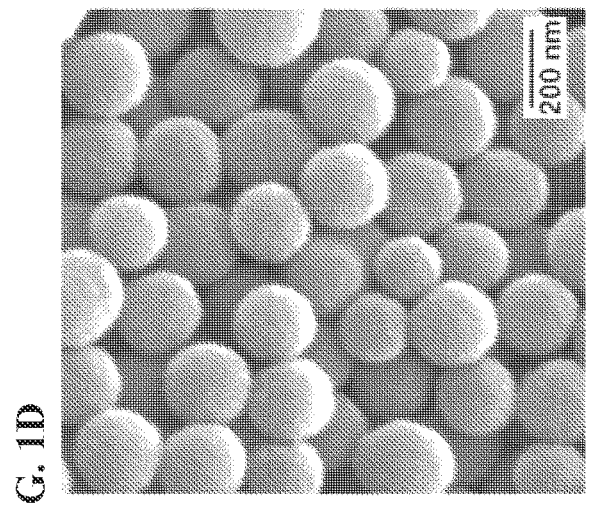
Figure 1B:
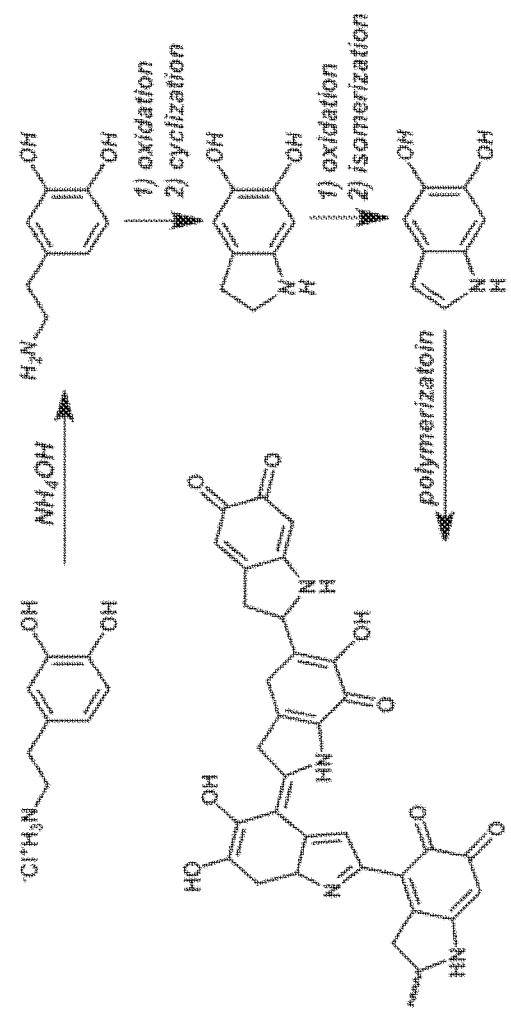
Figure 1D:
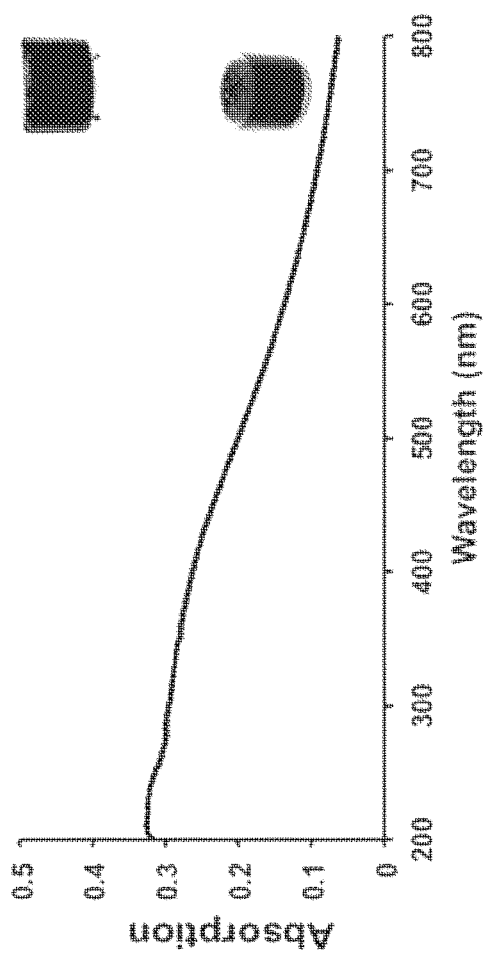
Figure 1E:
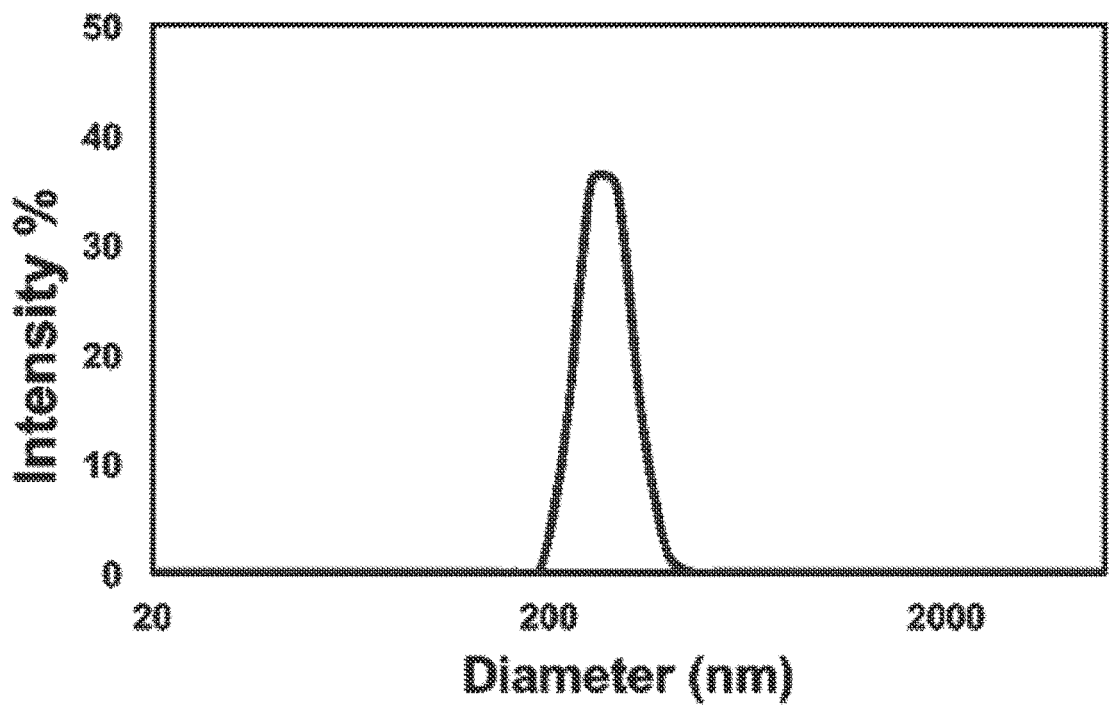
FIG. 1E. Dynamic light scattering (DLS) measurement of MelNPs.

While various embodiments and aspects of the present invention are shown and described herein, it will be obvious to those skilled in the art that such embodiments and aspects are provided by way of example only. Numerous variations, changes, and substitutions will now occur to those skilled in the art without departing from the invention. It should be understood that various alternatives to the embodiments of the invention described herein may be employed in practicing the invention.

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

The abbreviations used herein have their conventional meaning within the chemical and biological arts. The chemical structures and formulae set forth herein are constructed according to the standard rules of chemical valency known in the chemical arts.

The following definitions are provided to facilitate understanding of certain terms used frequently herein and are not meant to limit the scope of the present disclosure. The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The terms "melanin-defective disease" or "melanin-defective diseases" as used herein refer to a disorder or disease caused by a deficiency in melanin such as, for example, albinism (including oculocutaneous albinism), vitiligo and skin cancer.

The term "albinism" as used herein, refers to congenital disorder characterized by the complete or partial absence of pigment in the skin, hair and eyes. Albinism is associated with a number of vision defects, such as photophobia, nystagmus, and amblyopia. Lack of skin pigmentation makes for more susceptibility to sunburn and skin cancers. In rare cases such as Chediak-Higashi syndrome, albinism may be associated with deficiencies in the transportation of melanin granules. This also affects essential granules present in immune cells leading to increased susceptibility to infection. Various types of oculocutaneous albinism include, for example, OCA1-4, Hermansky-Pudlak syndrome, Chediak-Higashi syndrome, and Griscelli syndrome.

The term "vitiligo" as used herein, refers to a long term skin condition characterized by patches of the skin losing their pigment. The patches of skin affected become white and usually have sharp margins. The hair from the skin may also become white. Inside the mouth and nose may also be involved. Typically both sides of the body are affected. Often the patches begin on areas of skin that are exposed to the sun. It is more noticeable in people with dark skin. Vitiligo may result in psychological stress and those affected may be stigmatized.

The terms "synthetic melanin nanoparticles", "melanin-like nanoparticles" and "MelNPs", as used interchangeably herein, and which are intended to have the same meaning throughout the present disclosure, refer to a non-natural nanoparticle composed of (e.g. consisting of or consisting essentially of) melanin that is not bound to, conjugated to, attached to, coated by, encompassed by or otherwise associated with a proteinaceous lipid (i.e. a lipid comprising one or more proteins such as the lipid (plasma) membrane of a melanocyte or melanosome). In embodiments, the non-natural nanoparticle of the present disclosure is composed of melanin and is not bound to, conjugated to, attached to, coated by, encompassed by or otherwise associated with a lipid (e.g. a lipid bilayer, lipid membrane or phospholipid compound). Synthetic melanin particles are capable of functioning as a pigment.

The terms "melanin" and "melanin polymer" as used interchangeably herein, refer to a polymer (i.e., "melanin polymer" comprising two or more melanin monomers) or a plurality of polymers (i.e. a plurality of melanin polymers) that function as a pigment, particularly when in nanoparticle form.

The terms "keratinocyte" and "keratinocytes" as used herein, refer to the predominant cell type in the epidermis, the outermost layer of the skin, constituting the majority (e.g., 90°%-95%) of the cells found there. Keratinocytes are found in the deepest basal layer of the stratified epithelium that comprises the epidermis, and are sometimes referred to as basal cells or basal keratinocytes. Keratinocytes are maintained at various stages of differentiation in the epidermis and are responsible for forming tight junctions with the nerves of the skin. They also keep Langerhans cells of the epidermis and lymphocytes of the dermis in place. Keratinocytes contribute to protecting the body from UV radiation by taking up melanosomes. Keratinocytes contribute to protecting the body from UV radiation by taking up melanosomes, vesicles containing the endogenous photoprotectant melanin, from epidermal melanocytes. Each melanocyte in the epidermis has several dendrites that stretch out to connect it with many keratinocytes. The melanin is then stored within keratinocytes and melanocytes in the perinuclear area as "supranuclear caps", where it protects the DNA from UV-induced damage. In addition to their structural role, keratinocytes play a role in immune system function. The skin is the first line of defense and keratinocytes serve as a barrier between an organism and its environment. In addition to preventing toxins and pathogens from entering an organisms body, they prevent the loss of moisture, heat and other important constituents of the body. In addition to their physical role, keratinocytes serve a chemical immune role as immunomodulaters, responsible for secreting inhibitory cytokines in the absence of injury and stimulating inflammation and activating Langerhans cells in response to injury. Langerhans cells serve as antigen-presenting cells when there is a skin infection and are the first cells to process microbial antigens entering the body from a skin breach.

The term "endocytosis" as used herein, refers to a form of active transport in which a cell transports molecules (such as proteins) into the cell by engulfing them in an energy-using process. Endocytosis includes pinocytosis and phagocytosis. Pinocytosis is a mode of endocytosis in which small particles are brought into the cell, forming an invagination, and then suspended within small vesicles. These pinocytotic vesicles subsequently fuse with lysosomes to hydrolyze (break down) the particles. Phagocytosis is the process by which a cell engulfs a solid particle to form an internal compartment known as a phagosome.

The term "perinuclear aggregation" as used herein, refers to an abnormal distribution of mitochondria within a cell characterized by a reduction in the mitochondrial numerical density at the periphery of the ceil (e.g., 60-100μιη from the nucleus) in comparison to the distribution observed in a cell from a healthy subject The term "fused ring melanin polymer" as used herein, is a melanin polymer which includes (e.g. consists of or consists essentially of) a plurality of fused ring heteroaryl monomers and/or fused ring heterocycloalkyl monomers, a plurality of dopamine monomers, or a plurality of fused ring metal-binding melanin monomers, and the like. The fused ring melanin polymer can be cross-linked.

The terms "fused ring heteroaryl monomer" or "fused ring heteroaryl monomers" as used herein, refer to a monomer (e.g. a monovalent, divalent of trivalent monomer) of a polymer that includes a fused ring heteroaryl moiety (e.g. a monovalent, divalent of trivalent moiety). In embodiments, the fused ring heteroaryl monomer is a fused ring heteroaryl moiety (e.g. a monovalent, divalent of trivalent moiety).

The terms "fused ring heterocycloalkyl monomer" or "fused ring heterocycloalkyl monomers" as used herein, refer to a monomer (e.g. a monovalent, divalent of trivalent monomer) of a polymer that includes a fused ring heterocycloalkyl moiety (e.g. a monovalent, divalent of trivalent moiety). In embodiments, the fused ring heterocycloalkyl monomer as used herein refer, is a fused ring heterocycloalkyl moiety (e.g. a monovalent, divalent of trivalent moiety).

Each of a fused ring heteroaryl monomer and/or fused ring heterocycloalkyl monomer may be substituted with one or more substituents selected from hydroxyl, carboxyl and/or oxy. In embodiments, the fused ring heteroaryl monomer is not substituted with an oxy. Each of the fused ring heteroaryl monomer is a 6,6-fused ring heteroaryl monomer, a 5,6-fused ring heteroaryl monomer or 6,5-fused ring heteroaryl monomer and each of the fused ring heterocycloalkyl moieties is a 6,6-fused ring heterocycloalkyl monomer, a 5,6-fused ring heterocycloalkyl 1 monomer or 6,5- fused ring heterocycloalkyl monomer. The fused ring heteroaryl monomer and/or fused ring heterocycloalkyl monomer (in the monovalent or bivalent form) are selected from indole monomers (including but not limited to dihydroxyindole, 5,6-dihydroxyindole (DHI), 5,6-dihydroxyindole-2-carboxylic acid, dioxyindole, 5,6-dioxyindole, and 5,6-droxyindole-2-carboxylic acid), benzothiazine monomers and benzothiazole monomers. The fused ring monomelic units of the fused ring melanin polymer can be dihydroxy fused ring units (e.g. dihydroxy fused ring heteroaryl moieties and/or dihydroxy fused ring heterocycloalkyl moieties) wherein the hydroxy substituents are attached to adjacent carbons of a 6 membered ring (e.g. 6 membered carbon ring) of a fused ring monomer (also referred to herein as a "catechol fused ring monomer"). The fused ring melanin polymer may also contained oxidized versions of the dihydroxy fused ring units wherein one or both of the hydroxyl substituents are oxy substituents.

The terms "dopamanine monomer" and "dopamine monomers" as used herein, include but are not intended to be limited to a monomer including a dihydoxydopamine moiety, 3,4-dihydoxydopamine moiety, dioxydpoamine moiety or a 3,4-dioxydopamine moietyV In embodiments, the dopamanine monomer is a dihydoxydopamine moiety, 3,4-dihydoxydopamine moiety, dioxydpoamine moiety or 3,4-dioxydopamine moiety The term "metal-binding melanin polymer" as used herein, refers to a melanin polymer bound to a plurality of transitions metals including but not limited to iron. In embodiments, the metal-binding melanin polymer is a fused ring melanin polymer.

The term "nanoparticle" as used herein, refers to a particle whose longest dimension is less than 1μιη.

The term "sphere" as used herein, in the usual and customary sense, refers to a round or substantially round geometrical object in three-dimensional space that is substantially the surface of a completely round ball, analogous to a circular object in two dimensions. A sphere may be defined mathematically as the set of points that are all at the same or substantially all at the same distance r from a given point, but in three-dimensional space, where r is the radius of the mathematical ball and the given point is the center or substantially the center of the mathematical ball. In embodiments, the longest straight line through the ball, connecting two points of the sphere, passes through the center and its length is thus twice the radius; it is a diameter of the ball. A nanosphere is a nanoparticle having a radius of less than 1μιη.

The term "nanorod" as used herein, in the usual and customary sense, refers to a nanoparticle having a rod-like morphology. In embodiments, the longest dimension of the nanorod is less than 1μιη. In embodiments, the longest dimension of the nanorod is from about 1-100 nm. Nanorods may be synthesized by direct chemical synthesis where a combination of ligands act as shape control agents and bond to different facets of the nanorod with different strengths. This can allow different faces of the nanorod to grow at different rates, producing a substantially elongated object. In embodiments, the aspect ratio (length divided by width) of a nanorod is about 3-5.

The term "high aspect ratio" as used herein, in the usual and customary sense, refers to the ratio of the sizes of a geometric shape in different dimensions. For example, the aspect ratio of a rectangle is the ratio of its longer side to its shorter side, i.e., the ratio of width to height, when the rectangle is oriented in a landscape view.

The term "transdermal patch" or "patch" as used herein, in the usual and customary sense, refers to an adhesive patch, typically incorporated with a pharmaceutical composition or formulation containing a drug or medicament, that is placed on the skin of a subject or patient to deliver a specific dose of a drug or medicament through the skin and into the bloodstream. For example, this promotes healing directly to an injured area of the body. The transdermal delivery of a drug or medicament typically provides, or can provide, a controlled release of the medication into a patient, or subject, usually through either a porous membrane covering a reservoir of drug or medicament or through body heat melting thin layers of drug or medicament embedded in the adhesive.

The term "biocompatible" as used herein refers, in the usual and customary sense, to toleration of a non-physiological composition by an organism or cell.

The terms "ultraviolet induced damage" and "UV induced damage" as used interchangeably herein refer, in the usual and customary sense, to chemical changes attending irradiation of light of sufficient energy. UV induced damage can include scission of nucleic acids (e.g., DNA or RNA), and breaking of bonds in proteins, lipids, and other physiological molecules. For example, the damage can be damage resulting from reactive oxygen species (ROS).

The terms "reactive oxygen species" and "ROS" as used interchangeably herein refer, in the usual and customary sense, to transient species, typically formed during exposure to radiation (e.g., UV irradiation) capable of inducing oxidative decomposition.

The terms "under conditions suitable to afford uptake", "taken up" and "take up" as used herein, refer, in the usual and customary sense, to experimental conditions well known in the art which allow uptake (e.g., endocytosis) of a species into a cell.

The terms "treating" or "treatment" as used herein, refers to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating," and conjugations thereof, include prevention of an injury, pathology, condition, or disease.

The term "effective amount" as used herein, refers to an amount sufficient to accomplish a stated purpose (e.g. Achieve the effect for which it is administered, treat a disease, reduce one or more symptoms of a disease or condition, and the like). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

The term "administering" as used herein, refers to oral administration, administration as an inhaled aerosol or as an inhaled dry powder, suppository, topical contact, intravenous, parenteral, intraperitoneal, intramuscular, intralcsional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies, for example cancer therapies such as chemotherapy, hormonal therapy, radiotherapy, or immunotherapy. The compound of the invention can be administered alone or can be co-administered to the patient. Co-administration is meant to include simultaneous or sequential administration of the compound individually or in combination (more than one compound or agent). The compositions of the present invention can be delivered transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions of the present invention can also be delivered as microspheres for slow release in the body. For example, microspheres can be administered via intradermal injection of drug-containing microspheres, which slowly release subcutaneously (see Rao, *J Biomater Sci. Polym. Ed* 7:623-645, 1995: as biodegradable and injectable gel formulations (see, e.g., Gao *Pharm. Res.* 12:857-863, 1995); or, as microspheres for oral administration (see, e.g., Eyles, *J Pharm. Pharmacol.* 49:669-674, 1997). In another embodiment, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, *J. Microencapsul.* 13:293306, 1996; Chonn, *Curr. Opin. Biotechnol.* 6:698-708, 1995; Ostro, *Am. J Hasp. Pharm.* 46:1576-1587, 1989).

The term "alkyl," by itself or as part of another substituent, means, unless otherwise stated, a straight (i.e., unbranched) or branched carbon chain (or carbon), or combination thereof, which may be fully saturated, mono- or polyunsaturated and can include di- and multivalent radicals, having the number of carbon atoms designated (i.e., $C_i$-$C_{i_0}$ means one to ten carbons). Alkyl is not cyclized. Examples of saturated hydrocarbon radicals include, but are not limited to, groups such as methyl, ethyl, n-propyl, isopropyl, n-butyl, t-butyl, isobutyl, sec-butyl, (cyclohexyl) methyl, homologs and isomers of, for example, n-pentyl, n-hexyl, n-heptyl, n-octyl, and the like. An unsaturated alkyl group is one having one or more double bonds or triple bonds (e.g. alkene, alkyne). Examples of unsaturated alkyl groups include, but are not limited to, vinyl, 2-propenyl, crotyl, 2-isopentenyl, 2-(butadienyl), 2,4-pentadienyl, 3-(1, 4-pentadienyl), ethynyl, 1- and 3-propynyl, 3-butynyl, and the higher homologs and isomers. An alkoxy is an alkyl attached to the remainder of the molecule via an oxygen linker (—O—).

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched non-cyclic chain, or combinations thereof, including at least one carbon atom and at least one heteroatom (e.g. O, N, P, Si, and S), and wherein the nitrogen and sulfur atoms may optionally be oxidized, and the nitrogen heteroatom may optionally be quaternized. The heteroatom(s) (e.g. O, N, P, S, and Si) may be placed at any interior position of the heteroalkyl group or at the position at which the alkyl group is attached to the remainder of the molecule. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, —O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH)$_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P). The term "heteroalkenyl," by itself or in combination with another term, means, unless otherwise stated, a heteroalkyl including at least one double bond. A heteroalkenyl may optionally include more than one double bond and/or one or more triple bonds in additional to the one or more double bonds. The term "heteroalkynyl," by itself or in combination with another term, means, unless otherwise stated, a heteroalkyl including at least one triple bond. A heteroalkynyl may optionally include more than one triple bond and/or one or more double bonds in additional to the one or more triple bonds.

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —RC(O)$_2$—. As described above, heteroalkyl groups, as used herein, include those groups that are attached to the remainder of the molecule through a heteroatom, such as —C(O)R, —C(O)NR', —NR'R", —OR, —SR, and/or —SO$_2$R. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, non-aromatic cyclic versions of "alkyl" and "heteroalkyl," respectively, wherein the carbons making up the ring or rings do not necessarily need to be bonded to a hydrogen due to all carbon valencies participating in bonds with non-hydrogen atoms. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, 3-hydroxy-cyclobut-3-enyl-1,2, dione, 1H-1,2,4-triazolyl-5(4H)-one, 4H-1,2,4-triazolyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively. A heterocycloalkyl moiety may include one ring heteroatom (e.g., O, N, S, Si, or P). A heterocycloalkyl moiety may include two optionally different ring heteroatoms (e.g., O, N, S, Si, or P). A heterocycloalkyl moiety may include three optionally different ring heteroatoms (e.g., O, N, S, Si, or P). A heterocycloalkyl moiety may include four optionally different ring heteroatoms (e.g., O, N, S, Si, or P). A heterocycloalkyl moiety may include five optionally different ring heteroatoms (e.g., O, N, S, Si, or P). A heterocycloalkyl moiety may include up to 8 optionally different ring heteroatoms (e.g., O, N, S, Si, or P).

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$) alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). In embodiments, the fused ring heteroaryl is two rings fused together wherein at least one of the fused rings is a heteroaromatic group. A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. Non-limiting examples of heteroaryl groups include pyridinyl, pyrimidinyl, thiophenyl, thienyl, furanyl, indolyl, benzoxadiazolyl, benzodioxolyl, benzodioxanyl, thianaphthanyl, pyrrolopyridinyl, indazolyl, quinolinyl, quinoxalinyl, pyridopyrazinyl, quinazolinonyl, benzoisoxazolyl, imidazopyridinyl, benzofuranyl, benzothienyl, benzothiophenyl, phenyl, naphthyl, biphenyl, pyrrolyl, pyrazolyl, imidazolyl, pyrazinyl, oxazolyl, isoxazolyl, thiazolyl, furylthienyl, pyridyl, pyrimidyl, benzothiazolyl, purinyl, benzimidazolyl, isoquinolyl, thiadiazolyl, oxadiazolyl, pyrrolyl, diazolyl, triazolyl, tetrazolyl, benzothiadiazolyl, isothiazolyl, pyrazolopyrimidinyl, pyrrolopyrimidinyl, benzotriazolyl, benzoxazolyl, or quinolyl. The examples above may be substituted or unsubstituted and divalent radicals of each heteroaryl example above are non-limiting examples of heteroarylene. A heteroaryl moiety may include one ring heteroatom (e.g., O, N, or S). A heteroaryl moiety may include two optionally different ring heteroatoms (e.g., O, N, or S). A heteroaryl moiety may include three optionally different ring heteroatoms (e.g., O, N, or S). A heteroaryl moiety may include four optionally different ring heteroatoms (e.g., O, N, or S). A heteroaryl moiety may include five optionally different ring heteroatoms (e.g., O, N, or S). An aryl moiety may have a single ring. An aryl moiety may have two optionally different rings. An aryl moiety may have three optionally different rings. An aryl moiety may have four optionally different rings. A heteroaryl moiety may have one ring. A heteroaryl moiety may have two optionally different rings. A heteroaryl moiety may have three optionally different rings. A heteroaryl moiety may have four optionally different rings. A heteroaryl moiety may have five optionally different rings.

A fused ring heterocyloalkylaryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substituents described herein. Thus, the term "heterocyloalkylaryl" includes fused ring heterocyloalkylaryl groups (i.e., multiple rings fused together wherein at least one of the fused rings is a heteroaromatic ring). In embodiments, the fused ring heterocyloalkylaryl is two rings fused together wherein at least one of the fused rings is a heteroaromatic group. A 5,6-fused ring heterocyloalkylarylene refers to two rings fused together, wherein one ring has 5 members and the other ring has 6 members, and wherein at least one ring is a heterocyloalkylaryl ring. Likewise, a 6,6-fused ring heterocyloalkylarylene refers to two rings fused together, wherein one ring has 6 members and the other ring has 6 members, and wherein at least one ring is a heterocyloalkylaryl ring. And a 6,5-fused ring heterocyloalkylarylene refers to two rings fused together, wherein one ring has 6 members and the other ring has 5 members, and wherein at least one ring is a heterocyloalkylaryl ring.

The term "oxo," as used herein, means an oxygen that is double bonded to a carbon atom.

Each of the above terms (e.g., "alkyl," "heteroalkyl," "aryl," and "heteroaryl") includes both substituted and unsubstituted forms of the indicated radical. Preferred substituents for each type of radical are provided below.

The term "alkylsulfonyl," as used herein, means a moiety having the formula —S($O_2$)—R', where R' is a substituted or unsubstituted alkyl group as defined above. R' may have a specified number of carbons (e.g., "$C_1$-$C_4$ alkylsulfonyl").

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR, =O, =NR', =N—OR, —NR'R", —SR, -halogen, —SiRR'R", —OC(O)R, —C(O)R, —$CO_2$R, —CONR'R", —OC(O)NR'R", —NR"C(O)R, —NR'—C(O) NR"R", —NR"C(O)$_2$R, —NR—C(NR'R"R''')=NR"", —NR—C(NR'R")=NR''', —S(O)R, —S(O)$_2$R, —S(O)$_2$ NR'R", —NRSO$_2$R, —NR'NR"R", —ONR'R", —NR'C(O)NR'NR"'R"", —CN, —NO$_2$, monophosphate (or derivatives thereof), diphosphate (or derivatives thereof), triphosphate (or derivatives thereof), in a number ranging from zero to (2m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound of the invention includes more than one R group, for example, each of the R groups is independently selected as are each R', R", R'", and R"" group when more than one of these groups is present. When R and R' are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR"', —S(O)R', —S(O)$_2$R', —S(O)$_2$NR'R", —NRSO$_2$R', —NR'NR"R'", —ONR'R", —NR'C(O)NR"NR"'R"", —CN, —NO$_2$, —R', —N$_3$, —CH(Ph)$_2$, fluoro(C$_1$-C$_4$)alkoxy, and fluoro(C$_1$-C$_4$)alkyl, monophosphate (or derivatives thereof), diphosphate (or derivatives thereof), triphosphate (or derivatives thereof), in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R", R'", and R"" groups when more than one of these groups is present.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In embodiments, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'— (C"R"R'")$_d$—, where s and d are independently integers of from 0 to 3, and X' is —O—, —NR'—, —S—, —S(O)—, —S(O)$_2$—, or —S(O)$_2$NR'—. The substituents R, R', R", and R'" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include, oxygen (O), nitrogen (N), sulfur (S), phosphorus (P), and silicon (Si).

A "substituent group," as used herein, means a group selected from the following moieties:

(A) oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, heteroaryl, substituted with at least one substituent selected from:

(i) oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, heteroaryl, substituted with at least one substituent selected from:

(a) oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NH C(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, heteroaryl, substituted with at least one substituent selected from: oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted $C_i$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{i0}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_i$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{i0}$ aryl, and each substituted or unsubstituted heteroaryl is a substituted or unsubstituted 5 to 9 membered heteroaryl.

In embodiments, each substituted group described in the compounds herein is substituted with at least one substituent group. For example, in embodiments, each fused ring heteroaryl moiety or heterocycloalkyl moiety described herein are substituted with at least one substituent group. In other embodiments, at least one or all of these moieties are substituted with at least one size-limited substituent group. In other embodiments, at least one or all of these moieties are substituted with at least one lower substituent group.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., *Journal of Pharmaceutical Science* 66:1-19 (1977)). Certain specific compounds of the present invention contain both basic and acidic functionalities that allow the compounds to be converted into either base or acid addition salts. Other pharmaceutically acceptable carriers known to those of skill in the art are suitable for the present invention. Salts tend to be more soluble in aqueous or other protonic solvents than are the corresponding free base forms. In other cases, the preparation may be a lyophilized powder in 1 mM-50 mM histidine, 0.1%-2% sucrose, 2%-7% mannitol at a pH range of 4.5 to 5.5, that is combined with buffer prior to use.

Thus, the compounds of the present invention may exist as salts, such as with pharmaceutically acceptable acids. The present invention includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

Provided herein are agents (e.g. compounds, drugs, therapeutic agents) that may be in a prodrug form. Prodrugs of the compounds described herein are those compounds that readily undergo chemical changes under select physiological conditions to provide the final agents (e.g. compounds, drugs, therapeutic agents). Additionally, prodrugs can be converted to agents (e.g. compounds, drugs, therapeutic agents) by chemical or biochemical methods in an ex vivo environment. Prodrugs described herein include compounds that readily undergo chemical changes under select physiological conditions to provide agents (e.g. compounds, drugs, therapeutic agents) to a biological system (e.g. in a subject).

Certain complexes and compounds of the present disclosure can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical or chiral centers) or double bonds; the enantiomers, racemates, diastereomers, tautomers, geometric isomers, stereoisomeric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

The terms "pharmaceutically acceptable excipient" and "pharmaceutically acceptable carrier" as used herein, refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" as used herein, is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

The term "contacting" as used herein is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents which can be produced in the reaction mixture.

The term "contacting" may include allowing two species to react, interact, or physically touch, wherein the two species may be, for example, a pharmaceutical composition as provided herein and a cell. In embodiments contacting includes, for example, allowing a pharmaceutical composition as described herein to interact with a cell or a patient.

The term "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaryotic cells. Prokaryotic cells include but are not limited to bacteria. Eukaryotic cells include but are not limited to yeast cells and cells derived from plants and animals, for example mammalian, insect (e.g., *Spodoptera*) and human cells.

The terms "analog" and "analogue" are used interchangeably and are used in accordance with their plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound, including isomers thereof. Accordingly, an analog is a compound that is similar or comparable in function and appearance but not in structure or origin to a reference compound.

The terms "oleosome" and "oleosomes" as used herein, refer structures found naturally in all oil bearing plant seeds. Oleosomes serve as natural storehouses of energy and are used by seeds until germination. Oleosomes are micron sized spheres of emollient plant oils combined with vitamin E, and surrounded by a phospholipid membrane and protein coat. The structure of oleosomes allows the oil component and vitamin E to be delivered to the skin in a delayed release manner.

The term "safflower oleosomes" as used herein, refers to oleosomes that contain safflower oil. Safflower oleosomes can be dispersed, for example, in a combination of purified water and vegetable glycerin. The structure of the oleosomes allows the sweet almond oil and vitamin E to be delivered to the skin in a delayed release manner. A portion of the nutrients reach the skin immediately and result in instantly smoother, softer skin.

The terms "elaiosome" and "elaiosomes" as used herein, refer to fleshy structures that are attached to the seeds of many plant species. The elaiosomes are is rich in lipids and proteins, and may be variously shaped. Elaiosomes develop in various ways either from seed tissues (chalaza, funiculus, hilum, raphe-antiraphe) or from fruit tissues (exocarp, receptacle, flower tube, perigonium, style or spicule).

The terms "ethasome" and "ethasomes" as used herein, refer to a vesicular carrier comprising a hydroalcoholic or hydro/alcoholic/glycolic phospholipid composition which enable delivery of high concentration of active ingredients through skin.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I), or carbon-14 ($^{14}$C). All isotopic variations of the compounds of the present invention, whether radioactive or not, are encompassed within the scope of the present invention.

The symbol "⤳" denotes the point of attachment of a chemical moiety to the remainder of a molecule or chemical formula.

In embodiments, a compound as described herein may include multiple instances of $R^2$ and/or other variables. In such embodiments, each variable may optional be different and be appropriately labeled to distinguish each group for greater clarity. For example, where each $R^2$ is different, they may be referred to, for example, as $R^{2.1}$, $R^{2.2}$, $R^{2.3}$, and/or $R^{2.4}$ respectively, wherein the definition of $R^2$ is assumed by $R^{2.1}$, $R^{2.2}$, $R^{2.3}$, and/or $R^{2.4}$. The variables used within a definition of $R^2$ and/or other variables that appear at multiple instances and are different may similarly be appropriately labeled to distinguish each group for greater clarity. In some embodiments, the compound is a compound described herein (e.g., in an aspect, embodiment, example, claim, table, scheme, drawing, or figure).

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted C1-C20 alkyl, or unsubstituted 2 to 20 membered heteroalkyl," the group may contain one or more unsubstituted C1-C20 alkyls, and/or one or more unsubstituted 2 to 20 membered heteroalkyls. Moreover, where a moiety is substituted with an R substituent, the group may be referred to as "R-substituted."

Where a moiety is R-substituted, the moiety is substituted with at least one R substituent and each R substituent is optionally different. Where a particular R group is present in the description of a chemical genus, a Roman alphabetic symbol may be used to distinguish each appearance of that particular R group. For example, where multiple $R^{13}$ substituents are present, each $R^{13}$ substituent may be distinguished as $R^{13A}$, $R^{13B}$, $R^{13C}$, $R^{13D}$, etc., wherein each of $R^{13A}$, $R^{13B}$, $R^{13C}$, $R^{13D}$, etc. is defined within the scope of the definition of $R^{13}$ and optionally differently.

Descriptions of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

As used herein, the term "about" means a range of values including the specified value, which a person of ordinary skill in the art would consider reasonably similar to the specified value. In embodiments, about means within a standard deviation using measurements generally acceptable in the art. In embodiments, about means a range extending to +1-10% of the specified value. In embodiments, about means the specified value.

The terms "disease" or "condition" refer to a state of being or health status of a patient or subject capable of being treated with a compound, pharmaceutical composition, or method provided herein. In embodiments, the disease is cancer (e.g. lung cancer, ovarian cancer, osteosarcoma, bladder cancer, cervical cancer, liver cancer, kidney cancer, skin cancer (e.g., Merkel cell carcinoma), testicular cancer, leukemia, lymphoma, head and neck cancer, colorectal cancer, prostate cancer, pancreatic cancer, melanoma, breast cancer, neuroblastoma). The disease may be an autoimmune, inflammatory, cancer, infectious, metabolic, developmental, cardiovascular, liver, intestinal, endocrine, neurological, or other disease.

A "control" sample or value refers to a sample that serves as a reference, usually a known reference, for comparison to a test sample. For example, a test sample can be taken from a patient suspected of having a given disease (cancer) and compared to samples from a known cancer patient, or a known normal (non-disease) individual. A control can also represent an average value gathered from a population of similar individuals, e.g., cancer patients or healthy individuals with a similar medical background, same age, weight, etc. A control value can also be obtained from the same individual, e.g., from an earlier-obtained sample, prior to disease, or prior to treatment. One of skill will recognize that controls can be designed for assessment of any number of parameters. One of skill in the art will understand which controls are valuable in a given situation and be able to analyze data based on comparisons to control values. Controls are also valuable for determining the significance of data. For example, if values for a given parameter are widely variant in controls, variation in test samples will not be considered as significant.

The term "melanoma" is taken to mean a tumor arising from the melanocytic system of the skin and other organs. Melanomas that may be treated with a compound, pharmaceutical composition, or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

As used herein, the terms "metastasis," "metastatic," and "metastatic cancer" can be used interchangeably and refer to the spread of a proliferative disease or disorder, e.g., cancer, from one organ or another non-adjacent organ or body part. Cancer occurs at an originating site, e.g., breast, which site is referred to as a primary tumor, e.g., primary breast cancer. Some cancer cells in the primary tumor or originating site acquire the ability to penetrate and infiltrate surrounding normal tissue in the local area and/or the ability to penetrate the walls of the lymphatic system or vascular system circulating through the system to other sites and tissues in the body. A second clinically detectable tumor formed from cancer cells of a primary tumor is referred to as a metastatic or secondary tumor. When cancer cells metastasize, the metastatic tumor and its cells are presumed to be similar to those of the original tumor. Thus, if lung cancer metastasizes to the breast, the secondary tumor at the site of the breast consists of abnormal lung cells and not abnormal breast cells. The secondary tumor in the breast is referred to a metastatic lung cancer. Thus, the phrase metastatic cancer refers to a disease in which a subject has or had a primary tumor and has one or more secondary tumors. The phrases non-metastatic cancer or subjects with cancer that is not metastatic refers to diseases in which subjects have a primary tumor but not one or more secondary tumors. For example, metastatic lung cancer refers to a disease in a subject with or with a history of a primary lung tumor and with one or more secondary tumors at a second location or multiple locations, e.g., in the breast.

The term "associated" or "associated with" in the context of a substance or substance activity or function associated with a disease (e.g., melanin-defective diseases, diabetes, cancer (e.g. prostate cancer, renal cancer, metastatic cancer, melanoma, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma) means that the disease (e.g. melanin-defective disease, lung cancer, ovarian cancer, osteosarcoma, bladder cancer, cervical cancer, liver cancer, kidney cancer, skin cancer (e.g., Merkel cell carcinoma), testicular cancer, leukemia, lymphoma, head and neck cancer, colorectal cancer, prostate cancer, pancreatic cancer, melanoma, breast cancer, neuroblastoma) is caused by (in whole or in part), or a symptom of the disease is caused by (in whole or in part) the substance or substance activity or function.

"Patient" or "subject in need thereof" refers to a living organism suffering from or prone to a disease or condition that can be treated by administration of a composition or pharmaceutical composition as provided herein. Non-limiting examples include humans, other mammals, bovines, rats, mice, dogs, monkeys, goat, sheep, cows, deer, and other non-mammalian animals. In some embodiments, a patient is human.

Synthetic Melanin Nanoparticles

According to the present disclosure, synthetic melanin nanoparticles, also referred to interchangeably herein as melanin-like nanoparticles (MelNPs), were prepared by spontaneous oxidation of melanin monomers in an aqueous solution under alkaline conditions, to produce biocompatible, synthetic analogues of naturally occurring melanosomes. The uptake, transport, distribution and UV-protective capabilities of the synthetic melanin nanoparticles in human keratinocytes were investigated. In particular, the synthetic melanin nanoparticles are endocytosed, undergo perinuclear aggregation, and form a supranuclear cap, or so called microparasol in human epidermal keratinocytes (HEKa), mimicking the behavior of natural melanosomes in terms of cellular distribution and to serve to protect the cells from UV damage.

The present disclosure provides synthetic melanin nanoparticles, compositions, pharmaceutical formulations and uses thereof. The synthetic melanin nanoparticles of the present disclosure can be, for example, monodisperse, and demonstrate similar broad band ultraviolet (UV) absorption as with natural melanins. In addition, the synthetic melanin nanoparticles of the present disclosure are capable of accumulating around a perinuclear area to form a supranuclear cap after incubating with human epidermal keratinocytes cells, as with natural melanin in the same type of cells. Moreover, the synthetic melanin nanoparticles of the present disclosure can also degrade in lysosomes, as with natural melanins, to form melanosomes. When treated with the synthetic melanin nanoparticles of the present disclosure, human epidermal keratinocytes cells show higher ability of tolerance for UV damage, indicating the similar photoprotection capability of the synthetic melanin nanoparticles of the present disclosure as with natural melanins. Moreover, photoprotection of UV irradiation of synthetic melanin nanoparticles is useful for application in melanin-defective diseases, such as albinism and vitiligo.

In embodiments, the synthetic melanin nanoparticles of the present disclosure are non-natural nanoparticles composed of (e.g. consisting of or consisting essentially of) melanin that is not bound to, conjugated to, attached to, coated by, encompassed by or otherwise associated with a lipid (i.e. a lipid comprising one or more proteins such as the lipid (plasma) membrane of a melanocyte or melanosome).

In embodiments, the synthetic melanin nanoparticles of the present disclosure are non-natural nanoparticles composed of (e.g. consisting of or consisting essentially of) melanin that is not bound to, conjugated to, attached to, coated by, encompassed by or otherwise associated with a proteinaceous lipid (i.e. a lipid comprising one or more proteins such as the lipid (plasma) membrane of a melanocyte or melanosome).

In embodiments, the melanin polymer is a fused ring melanin polymer which includes (e.g. consists of or consists essentially of) monomers of fused ring heteroaryl monomer and/or fused ring heterocycloalkyl monomers.

In embodiments, the melanin polymer is a fused ring metal-binding melanin polymer comprising a melanin polymer bound to a plurality of transitions metals including but not limited to iron.

In embodiments, the fused ring melanin polymer is a dopamine monomer, including but not limited to dihydoxydopamine, 3,4-dihydoxydopamine, dioxydpoamine and/or 3,4-dioxydopamine.

In embodiments, each of a fused ring heteroaryl monomer and/or fused ring heterocycloalkyl monomer may be substituted with one or more substituents selected from hydroxyl, carboxyl and/or oxy. Each of the fused ring heteroaryl monomer is a 6,6-fused ring heteroaryl monomer, a 5,6-fused ring heteroaryl monomer or 6,5-fused ring heteroaryl monomer and each of the fused ring heterocycloalkyl moieties is a 6,6-fused ring heterocycloalkyl monomer, a 5,6-fused ring heterocycloalkyl 1monomer or 6,5-fused ring heterocycloalkyl monomer. In embodiments, the fused ring heteroaryl monomers and/or fused ring heterocycloalkyl monomers (in the monovalent or bivalent form) are selected from indole (such as dihydroxyindole, 5,6-dihydroxyindole (DHI), 5,6-dihydroxyindole-2-carboxylic acid, dioxyindole, 5,6-dioxyindole, 5,6-droxyindole-2-carboxylic acid), benzothiazine, benzothiazole. In embodiments, the fused ring monomelic units of the fused ring melanin polymer are dihydroxy fused ring units (e.g. dihydroxy fused ring heteroaryl monomers and/or dihydroxy fused ring heterocycloalkyl monomers) wherein the hydroxy substituents are attached to adjacent carbons of a 6 membered ring (e.g. 6 membered carbon ring) of a fused ring monomer (also referred to herein as a "catechol fused ring monomer"). The fused ring melanin polymer may also contained oxidized versions of the dihydroxy fused ring units wherein one or both of the hydroxyl substituents are oxy substituents.

In embodiments, the synthetic melanin nanoparticles can be in the form of a sphere, hollow sphere, nanorod, worm-like configuration, cylindrical configuration, and the like, with at least one dimensional axis thereof of from about 1 nm to about 1000 nm, from about 1 nm to about 1000 nm, from about 50 nm to about 500 nm, or from about 100 nm to about 300 nm, preferably with a high aspect ratio.

In embodiments, the synthetic melanin nanoparticles is in the form of a sphere of from about 50 nm to about 500 nm, from about 100 nm to about 300 nm, from about 150 nm to about 250 nm, or about 250 nm in average diameter.

In embodiments, the synthetic melanin nanoparticles are in the form of a hollow sphere, optionally filled with silica.

In embodiments, the synthetic melanin nanoparticles are capable of functioning as a pigment.

Methods of Treating

In an aspect, a method for protecting a cell from ultraviolet (UV) damage is provided, the method comprising contacting a cell with a synthetic melanin-nanoparticle, the synthetic melanin nanoparticle comprising one or more melanin polymers, wherein the synthetic melanin nanoparticle is capable of functioning as a pigment for the protection of the cell from UV damage.

In another aspect, a method for treating a melanin-defective disease in a subject in need thereof is provided, the method comprising administering to the subject a synthetic melanin nanoparticle, the synthetic melanin nanoparticle comprising one or more melanin polymers, wherein the synthetic melanin nanoparticle is capable of protecting the subject from UV damage.

In embodiments, the synthetic melanin nanoparticle is biocompatible.

In embodiments, the cell is a keratinocyte.

In embodiments, the one or more melanin polymers is not bound to, conjugated to, attached to, coated by, encompassed by or otherwise associated with a lipid.

In embodiments, the one or more melanin polymers is not bound to, conjugated to, attached to, coated by, encompassed by or otherwise associated with a proteinaceous lipid.

In embodiments, the one or more melanin polymers is a metal-binding melanin polymer.

In embodiments, the metal component of the metal-binding melanin polymer is a transition metal.

In embodiments, the transition metal is iron.

In embodiments, the one or more melanin polymers is a fused ring melanin polymer comprising a plurality of fused ring heteroaryl monomers.

In embodiments, the one or more melanin polymers is a fused ring melanin polymer comprising a plurality of fused ring heterocycloalkyl monomers.

In embodiments, the fused ring melanin polymer is a fused ring metal-binding melanin polymer.

In embodiments, the metal component of the metal-binding melanin polymer is a transition metal.

In embodiments, the transition metal is iron.

In embodiments, the fused ring melanin polymers comprise a plurality of dopamine monomers.

In embodiments, the dopamine monomers are selected from the group consisting of dihydoxydopamine monomers, 3,4-dihydoxydopamine monomers, dioxydpoamine monomers and 3,4-dioxydopamine monomers.

In embodiments, the fused ring heteroaryl monomers are substituted with one or more substituents selected from the group consisting of hydroxyl and carboxyl.

In embodiments, the fused ring heterocycloalkyl monomers are substituted with one or more substituents selected from the group consisting of hydroxyl, carboxyl and oxy.

In embodiments, the fused ring heteroaryl monomers and/or fused ring heterocycloalkyl monomers are selected from the group consisting of indole monomers, benzothiazine monomers and benzothiazole monomers.

In embodiments, the indole monomers are selected from the group consisting of dihydroxyindole monomers, 5,6-dihydroxyindole (DHI) monomers, 5,6-dihydroxyindole-2-carboxylic acid monomers, dioxyindole monomers, 5,6-dioxyindole monomers, and 5,6-droxyindole-2-carboxylic acid monomers.

In embodiments, the fused ring heteroaryl monomers are a 6,6-fused ring heteroaryl monomer, a 5,6-fused ring heteroaryl monomer or a 6,5-fused ring heteroaryl monomer.

In embodiments, the fused ring heterocycloalkyl monomers are a 6,6-fused ring heterocycloalkyl monomer, a 5,6-fused ring heterocycloalkyl 1monomer or 6,5-fused ring heterocycloalkyl monomer.

In embodiments, the monomers are dihydroxy fused ring heteroaryl monomers.

In embodiments, the monomers are dihydroxy fused ring heterocycloalkyl monomers.

In embodiments, the monomers are a catechol fused ring monomer comprising hydroxy substituents attached to adjacent carbons of a 6 membered ring of the catechol fused ring monomer.

In embodiments, the fused ring melanin polymer is branched.

In embodiments, the melanin polymer results from spontaneous oxidation of a plurality of melanin monomers in an aqueous solution and under alkaline conditions.

In embodiments, the synthetic melanin nanoparticle is a sphere, a nanorod or a hollow sphere.

In embodiments, the synthetic melanin nanoparticle is a sphere.

In embodiments, the synthetic melanin nanoparticle is a hollow sphere.

In embodiments, the sphere comprises silica.

In embodiments, the synthetic melanin nanoparticle comprises at least one axis having a dimension of from about 1 nm to about 1000 nm.

In embodiments, the synthetic melanin nanoparticle comprises at least one axis having a dimension of from about 50 nm to about 500 nm.

In embodiments, the synthetic melanin nanoparticle comprises at least one axis having a dimension of from about 100 nm to about 300 nm.

In embodiments, the synthetic melanin nanoparticle comprises at least one axis having a dimension of from about 150 nm to about 250 nm.

In embodiments, the sphere is from about 150 nm to about 250 nm in average diameter.

In embodiments, the sphere is about 250 nm in average diameter.

In embodiments, the synthetic melanin nanoparticle undergoes endocytosis in the cell.

In embodiments, the synthetic melanin nanoparticle undergoes perinuclear aggregation in a cell.

In embodiments, the synthetic melanin nanoparticle comprises a supranuclear cap in a cell.

In embodiments, the damage is DNA damage.

In embodiments, the damage results from reactive oxygen species (ROS).

In embodiments, the synthetic melanin nanoparticle forms part of a synthetic melanin nanoparticle composition wherein the synthetic melanin nanoparticle is present at a concentration of from about 0.01 mg/ml to about 1.0 mg/ml within the synthetic melanin nanoparticle composition.

In embodiments, the synthetic melanin nanoparticle forms part of a synthetic melanin nanoparticle composition wherein the synthetic melanin nanoparticle is present at a concentration of from about 0.01 mg/ml to about 0.4 mg/ml within the synthetic melanin nanoparticle composition.

In embodiments, the synthetic melanin nanoparticle forms part of a synthetic melanin nanoparticle composition wherein the synthetic melanin nanoparticle is present at a concentration of about 0.02 mg/ml within the synthetic melanin nanoparticle composition.

In embodiments, the melanin-defective disease is vitiligo.

In embodiments, the melanin-defective disease is albinism.

In embodiments, the melanin-defective disease is skin cancer.

In embodiments, the synthetic melanin nanoparticle is administered topically.

In embodiments, the synthetic melanin nanoparticle is administered topically as a cream, gel, ointment, lotion, aerosol or liquid.

In embodiments, the synthetic melanin nanoparticle is administered topically with a transdermal patch.

In embodiments, the synthetic melanin nanoparticle is administered intravenously.

In embodiments, the synthetic melanin nanoparticle is administered orally.

In embodiments, the synthetic melanin nanoparticle is administered by injection.

In embodiments, the injection is an intraocular injection.

In embodiments, the injection is a localized injection.

In embodiments, the synthetic melanin nanoparticle is administered prior to, simultaneous with, or subsequent to UV exposure.

Pharmaceutical Compositions

In another aspect, a pharmaceutical composition comprising a synthetic melanin nanoparticle and one or more pharmaceutically acceptable excipients is provided, the synthetic melanin nanoparticle comprising one or more melanin polymers.

In embodiments, the synthetic melanin nanoparticle of the pharmaceutical composition is biocompatible.

In embodiments, the one or more melanin polymers of the pharmaceutical composition is not bound to, conjugated to, attached to, coated by, encompassed by or otherwise associated with a lipid.

In embodiments, the one or more melanin polymers of the pharmaceutical composition is not bound to, conjugated to, attached to, coated by, encompassed by or otherwise associated with a proteinaceous lipid.

In embodiments, the one or more melanin polymers of the pharmaceutical composition is a metal-binding melanin polymer.

In embodiments, the metal component of the metal-binding melanin polymer of the pharmaceutical composition is a transition metal.

In embodiments, the transition metal of the pharmaceutical composition is iron.

In embodiments, the one or more melanin polymers is a fused ring melanin polymer comprising a plurality of fused ring heteroaryl monomers.

In embodiments, the one or more melanin polymers of the pharmaceutical composition is a fused ring melanin polymer comprising a plurality of fused ring heterocycloalkyl monomers.

In embodiments, the fused ring melanin polymer of the pharmaceutical composition is a fused ring metal-binding melanin polymer.

In embodiments, the metal component of the fused ring metal-binding melanin polymer of the pharmaceutical composition is a transition metal.

In embodiments, the transition metal of the pharmaceutical composition is iron.

In embodiments, the fused ring melanin polymers of the pharmaceutical composition comprise a plurality of dopamine monomers.

In embodiments, the dopamine monomers of the pharmaceutical composition are selected from the group consisting of dihydoxydopamine monomers, 3,4-dihydoxydopamine monomers, dioxydpoamine monomers and 3,4-dioxydopamine monomers.

In embodiments, the fused ring heteroaryl monomers of the pharmaceutical composition are substituted with one or more substituents selected from the group consisting of hydroxyl and carboxyl.

In embodiments, the fused ring heterocycloalkyl monomers of the pharmaceutical composition are substituted with one or more substituents selected from the group consisting of hydroxyl, carboxyl and oxy.

In embodiments, the fused ring heteroaryl monomers and/or fused ring heterocycloalkyl monomers of the pharmaceutical composition are selected from the group consisting of indole monomers, benzothiazine monomers and benzothiazole monomers.

In embodiments, the indole monomers of the pharmaceutical composition are selected from the group consisting of dihydroxyindole monomers, 5,6-dihydroxyindole (DHI) monomers, 5,6-dihydroxyindole-2-carboxylic acid monomers, dioxyindole monomers, 5,6-dioxyindole monomers, and 5,6-droxyindole-2-carboxylic acid monomers.

In embodiments, the fused ring heteroaryl monomers of the pharmaceutical composition are a 6,6-fused ring heteroaryl monomer, a 5,6-fused ring heteroaryl monomer or a 6,5-fused ring heteroaryl monomer.

In embodiments, the fused ring heterocycloalkyl monomers of the pharmaceutical composition are a 6,6-fused ring heterocycloalkyl monomer, a 5,6-fused ring heterocycloalkyl 1 monomer or 6,5-fused ring heterocycloalkyl monomer.

In embodiments, the monomers of the pharmaceutical composition are dihydroxy fused ring heteroaryl monomers.

In embodiments, the monomers of the pharmaceutical composition are dihydroxy fused ring heterocycloalkyl monomers.

In embodiments, the monomers of the pharmaceutical composition are a catechol fused ring monomer comprising hydroxy substituents attached to adjacent carbons of a 6 membered ring of the catechol fused ring monomer.

In embodiments, the fused ring melanin polymer of the pharmaceutical composition is branched.

In embodiments, the synthetic melanin nanoparticle of the pharmaceutical composition is a sphere, a nanorod or a hollow sphere.

In embodiments, the synthetic melanin nanoparticle of the pharmaceutical composition is a sphere.

In embodiments, the synthetic melanin nanoparticle of the pharmaceutical composition is a hollow sphere.

In embodiments, the sphere of the pharmaceutical composition comprises silica.

In embodiments, the synthetic melanin nanoparticle of the pharmaceutical composition comprises at least one axis having a dimension of from about 1 nm to about 1000 nm.

In embodiments, the synthetic melanin nanoparticle of the pharmaceutical composition comprises at least one axis having a dimension of from about 50 nm to about 500 nm.

In embodiments, the synthetic melanin nanoparticle of the pharmaceutical composition comprises at least one axis having a dimension of from about 100 nm to about 300 nm.

In embodiments, the synthetic melanin nanoparticle of the pharmaceutical composition comprises at least one axis having a dimension of from about 150 nm to about 250 nm.

In embodiments, the pharmaceutical composition is a topical formulation.

In embodiments, the topical formulation is in the form of a cream.

In embodiments, the topical formulation is in the form of a lotion.

In embodiments, the topical formulation is in the form of an ointment.

In embodiments, the topical formulation is in the form of an aerosol.

In embodiments, the topical formulation is in the form of a liquid.

In embodiments, the topical formulation is suitable for administration with a transdermal patch.

In embodiments, the pharmaceutical composition is suitable for injection.

In embodiments, the injection is an intraocular injection.

In embodiments, the injection is a localized injection.

Provided herein are pharmaceutical compositions of synthetic melanin nanoparticles as disclosed herein suitable for formulation and administration in vitro or in vivo. Suitable carriers and excipients and their formulations are described in Remington: The Science and Practice of Pharmacy, 21st Edition, David B. Troy, ed., Lippincott Williams & Wilkins (2005). By pharmaceutically acceptable carrier is meant a material that is not biologically or otherwise undesirable, i.e., the material is administered to a subject without causing undesirable biological effects or interacting in a deleterious manner with the other components of the pharmaceutical composition in which it is contained. If administered to a subject, the carrier is optionally selected to minimize degradation of the active ingredient and to minimize adverse side effects in the subject.

Pharmaceutical compositions provided by the present invention include compositions wherein the synthetic melanin nanoparticles (e.g. compositions described herein, including embodiments or examples) is contained in a therapeutically effective amount, i.e., in an amount effective to achieve its intended purpose. The actual amount effective for a particular application will depend, inter alia, on the condition being treated. When administered in methods to treat a melanin-defective disease, the synthetic melanin nanoparticles described herein will contain an amount of active ingredient effective to achieve the desired result, e.g., modulating the activity of a target molecule, and/or reducing, eliminating, or slowing the progression of disease symptoms. Determination of a therapeutically effective amount of synthetic melanin nanoparticles of the invention is well within the capabilities of those skilled in the art, especially in light of the detailed disclosure herein.

Provided compositions can include a single agent or more than one agent. The compositions for administration will commonly include synthetic melanin nanoparticles as described herein dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of active agent in these formulations can vary widely, and will be selected primarily based on fluid volumes, viscosities, body weight and the like in accordance with the particular mode of administration selected and the subject's needs.

In one aspect, the compositions can be formulated as a topical composition applied directly to the skin. Formulations for topical administration can include, emulsions, creams, aqueous solutions, oils, ointments, putty, pastes, gels, lotions, milks and suspensions. In one aspect, the topical composition can include one or more surfactants and/or emulsifiers.

Surfactants (or surface-active substances) that may be present are anionic, non-ionic, cationic and/or amphoteric surfactants. Typical examples of anionic surfactants include, but are not limited to, soaps, alkylbenzenesulfonates, alkanesulfonates, olefin sulfonates, alkyl ether sulfonates, glycerol ether sulfonates, alpha-methyl ester sulfonates, sulfo fatty acids, alkyl sulphates, fatty alcohol ether sulphates, glycerol ether sulphates, fatty acid ether sulphates, hydroxy mixed ether sulphates, monoglyceride (ether) sulphates, fatty acid amide (ether) sulphates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, N-acylamino acids, e.g. acyl lactylates, acyl tartrates, acyl glutamates and acyl aspartates, alkyl oligoglucoside sulphates, protein fatty acid condensates (in particular wheat-based vegetable products) and alkyl (ether) phosphates. Examples of non-ionic surfactants include, but are not limited to, fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers or mixed formals, optionally partially oxidized alk(en)yl oligoglycosides or glucoronic acid derivatives, fatty acid N-alkylglucamides, protein hydrolysates (in particular wheat-based vegetable products), polyol fatty acid esters, sugar esters, sorbitan esters, polysorbates and amine oxides. Examples of amphoteric or zwitterionic surfactants include, but are not limited to, alkylbetaines, alkylamidobetaines, aminopropionates, aminoglycinates, imidazolinium-betaines and sulfobetaines.

In one aspect, the surfactant can be fatty alcohol polyglycol ether sulphates, monoglyceride sulphates, mono- and/or dialkyl sulfosuccinates, fatty acid isethionates, fatty acid sarcosinates, fatty acid taurides, fatty acid glutamates, alpha-olefinsulfonates, ether carboxylic acids, alkyl oligoglucosides, fatty acid glucamides, alkylamidobetaines, amphoacetals and/or protein fatty acid condensates.

Examples of zwitterionic surfactants include betaines, such as N-alkyl-N,N-dimethylammonium glycinates, for example cocoalkyldimethylammonium glycinate, N-acylaminopropyl-N,N-dimethylammonium glycinates, for example cocoacylaminopropyldimethylammonium glycinate, and 2-alkyl-3-carboxymethyl-3-hydroxyethylimidazolines having in each case 8 to 18 carbon atoms in the alkyl or acyl group, and cocoacylaminoethylhydroxyethyl-carboxymethyl glycinate.

In one aspect, the emulsifier can be a nonionogenic surfactant selected from the following: addition products of from 2 to 30 mol of ethylene oxide and/or 0 to 5 mol of propylene oxide onto linear fatty alcohols having 8 to 22 carbon atoms, onto fatty acids having 12 to 22 carbon atoms, onto alkylphenols having 8 to 15 carbon atoms in the alkyl group, and onto alkylamines having 8 to 22 carbon atoms in the alkyl radical; alkyl and/or alkenyl oligoglycosides having 8 to 22 carbon atoms in the alk(en)yl radical and the ethoxylated analogs thereof; addition products of from 1 to 15 mol of ethylene oxide onto castor oil and/or hydrogenated castor oil; addition products of from 15 to 60 mol of ethylene oxide onto castor oil and/or hydrogenated castor oil; partial esters of glycerol and/or sorbitan with unsaturated, linear or saturated, branched fatty acids having 12 to 22 carbon atoms and/or hydroxycarboxylic acids having 3 to 18 carbon atoms, and the adducts thereof with 1 to 30 mol of ethylene oxide; partial esters of polyglycerol (average degree of self-condensation 2 to 8), trimethylolpropane, pentaerythritol, sugar alcohols (e.g. sorbitol), alkyl glucosides (e.g. methyl glucoside, butyl glucoside, lauryl glucoside), and polyglucosides (e.g. cellulose) with saturated and/or unsaturated, linear or branched fatty acids having 12 to 22 carbon atoms and/or hydroxycarboxylic acids having 3 to 18 carbon atoms, and the adducts thereof with 1 to 30 mol of ethylene oxide; mixed esters of pentaerythritol, fatty acids, citric acid and fatty alcohols and/or mixed esters of fatty acids having 6 to 22 carbon atoms, methylglucose and polyols, preferably glycerol or polyglycerol, mono-, di- and trialkyl phosphates, and mono-, di- and/or tri-PEG alkyl phosphates and salts thereof; wool wax alcohols; polysiloxane-polyalkyl-polyether copolymers and corresponding derivatives; and block copolymers, e.g. polyethylene glycol-30 dipolyhydroxystearates. In one aspect, the emulsifier is a polyalkylene glycol such as, for example, polyethylene glycol or polypropylene glycol. In another aspect, the emulsifier is polyethylene glycol having a molecular weight 100 Da to 5,000 Da, 200 Da to 2,500 Da, 300 Da to 1,000 Da, 400 Da to 750 Da, 550 Da to 650 Da, or about 600 Da.

In another aspect, the emulsifier is a poloxamer. In one aspect, the poloxamer is a nonionic triblock copolymer composed of a central hydrophobic chain of polyoxypropylene (e.g., (poly (propylene oxide))) flanked by two hydrophilic chains of polyoxyethylene (e.g., poly (ethylene oxide)). In one aspect, poloxamer has the formula:

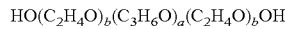

wherein a is from 10 to 100, 20 to 80, 25 to 70, or 25 to 70, or from 50 to 70; b is from 5 to 250, 10 to 225, 20 to 200, 50 to 200, 100 to 200, or 150 to 200. In another aspect, the poloxamer has a molecular weight from 2,000 to 15,000, 3,000 to 14,000, or 4,000 to 12,000. Poloxamers useful herein are sold under the tradename Pluronic® manufactured by BASF. Non-limiting examples of poloxamers useful herein include, but are not limited to, Pluronic® F68, P103, P105, P123, F127, and L121.

In another aspect, the emulsifier is composed of one or more fatty alcohols. In one aspect, the fatty alcohol is a linear or branched $C_6$ to $C_{35}$ fatty alcohol. Examples of fatty alcohols include, but are not limited to, capryl alcohol (1-octanol), 2-ethyl hexanol, pelargonic alcohol (1-nonanol), capric alcohol (1-decanol, decyl alcohol), undecyl alcohol (1-undecanol, undecanol, hendecanol), lauryl alcohol (dodecanol, 1-dodecanol), tridecyl alcohol (1-tridecanol, tridecanol, isotridecanol), myristyl alcohol (1-tetradecanol), pentadecyl alcohol (1-pentadecanol, pentadecanol), cetyl alcohol (1-hexadecanol), palmitoleyl alcohol (cis-9-hexadecen-1-ol), heptadecyl alcohol (1-n-heptadecanol, heptadecanol), stearyl alcohol (1-octadecanol), isostearyl alcohol (16-methylheptadecan-1-ol), elaidyl alcohol (9E-octadecen-1-ol), oleyl alcohol (cis-9-octadecen-1-ol), linoleyl alcohol (9Z, 12Z-octadecadien-1-ol), elaidolinoleyl alcohol (9E, 12E-octadecadien-1-ol), linolenyl alcohol (9Z, 12Z, 15Z-octadecatrien-1-ol) elaidolinolenyl alcohol (9E, 12E, 15-E-octadecatrien-1-ol), ricinoleyl alcohol (12-hydroxy-9-octadecen-1-ol), nonadecyl alcohol (1-nonadecanol), arachidyl alcohol (1-eicosanol), heneicosyl alcohol (1-heneicosanol), behenyl alcohol (1-docosanol), erucyl alcohol (cis-13-docosen-1-ol), lignoceryl alcohol (1-tetracosanol), ceryl alcohol (1-hexacosanol), montanyl alcohol, cluytyl alcohol (1-octacosanol), myricyl alcohol, melissyl alcohol (1-triacontanol), geddyl alcohol (1-tetratriacontanol), or cetearyl alcohol.

In one aspect, the carrier used to produce the topical composition is a mixture polyethylene and one or more fatty alcohols. For example, the carrier is composed of 50% to 99% by weight, 75% to 99% by weight, 90% to 990% by weight, or about 95% by weight polyethylene glycol and 1% to 50% by weight, 1% to 25% by weight, 1% to 10% by weight, or about 5% by weight fatty alcohol. In a further aspect, the carrier is a mixture of polyethylene glycol and cetyl alcohol.

The topical compositions can also include additional components typically present in such compositions. In one aspect, the topical composition can include one or more of the following components: fats, waxes, pearlescent waxes, bodying agents, thickeners, superfatting agents, stabilizers, polymers, silicone compounds, lecithins, phospholipids, biogenic active ingredients, deodorants, antimicrobial agents, antiperspirants, swelling agents, insect repellents, hydrotropes, solubilizers, preservatives, perfume oils and dyes. Examples of each of these components are disclosed in U.S. Pat. No. 8,067,044, which is incorporated by reference with respect these components.

The topical compositions composed of the synthetic melanin nanoparticles described herein can be prepared by mixing compositions with the carrier. In the case when the carrier is composed of two or more components, the components can be admixed with one another prior to the addition of the synthetic melanin nanoparticles. The amount of synthetic melanin nanoparticles present in the topical composition can vary depending upon the application. In one aspect, the synthetic melanin nanoparticles are from about 0.001 weight % to about 99 weight %, from about 0.01 weight % to about 90 weight %, from about 0.1 weight % to about 80 weight %, from about 1 weight % to about 70 weight %, from about 2 weight % to about 70 weight %, from about 3 weight % to about 60 weight %, from about 4 weight % to about 50 weight %, from about 5 weight % to about 40 weight %, from about 10 weight % to about 30 weight %, or from about 15 weight % to about 20 weight % of the topical composition.

In embodiments, the topical formulation may include one or more of a fast-spreading emollient such as, for example, dicaprylyl carbonate, and the like; a medium-spreading emollient such as, for example, cetearyl isononanoate, and the like; an antioxidant such as, for example, tocopherols, including but not limited to alpha-tocopherol, and the like, which are forms of and/or related to vitamin E; a rheological control agent such as, for example, polyquaternium-37, propylene glycol dicaprylate/dicaprate, PPG-1 Trideceth-6 (a cationic homopolymer), and the like; a water-resistant agent such as a hydrogenated dimer dilinoleyl/dimethylcarbonate copolymer, and the like; a self-emulsifying base such as, for example, cetearyl glucoside, cetearyl alcohol, and the like, which are ubiquitous in lotions and other similar products; and strong, anionic emulsifiers such as sodium stearoyl glutamate, and the like.

In embodiments, the topical formulation may include one or more of glycerin; PEG (various); petrolatum; stearic acid; preservatives such as parabens and the like; silicones such as dimethicone and the like; fruit oils such as avocado, olive, and the like; emulsifiers such as polysorbates, and the like; antioxidants such as plant flavonoids and the like; natural encapsulation systems such as oleosomes, including safflower oleosomes, elaiosomes, ethosomes, and the like (Akiladevi, D.; Basak, S. Ethosomes—A noninvasive approach for transdermal drug delivery. Int J Current Pharm Res, 2010, 2, 4; Akiladevi, D.; Basak, S. Ethosomes—A noninvasive approach for transdermal drug delivery. Int J Current Pharm Res, 2010, 2, 4; Rouse, J., et al. Effects of mechanical flexion on the penetration of fullerene amino acid-derivatized peptide nanoparticles through skin, Nano Letters, 2007, 7, 1); and dihydroxyacetone (DHA).

In embodiments, ethosomes may contain phospholipids with various chemical structures like phosphatidylcholine (PC), hydrogenated PC, phosphatidic acid (PA), phosphatidylserine (PS), phosphatidylethanolamine (PE), phosphatidylglycerol (PPG), phosphatidylinositol (PI), hydrogenated PC, alcohol (ethanol or isopropyl alcohol), water and propylene glycol (or other glycols) [69]. Drug delivery can be modulated by altering alcohol, water or alcohol-polyol: water ratio. Some preferred phospholipids are soya phospholipids such as Phospholipon 90 (PL-90). It is usually employed in a range of 0.5-10% w/w. Cholesterol at concentrations ranging between 0.1-1% can also be added to the preparation. Examples of alcohols, which can be used, include ethanol and isopropyl alcohol. Among glycols, propylene glycol and Transcutol are generally used. In addition, non-ionic surfactants (PEG-alkyl ethers) can be combined with the phospholipids in these preparations. Cationic lipids like cocoamide, POE alkyl amines, dodecylamine, cetrimide etc. can be added too. The concentration of alcohol in the final product may range from 20 to 50%. The concentration of the non-aqueous phase (alcohol and glycol combination) may range between 22 to 70%

In embodiments, ethasome formulations may include one or more of a phospholipid as a vesicle forming component such as, for example, soya phosphatidyl choline, egg phoshphatidyl choline, dipamityl phosphatidyl choline, distearyl phosphatidyl choline, and the like; a polyglycol as a skin penetration enhancer, such as for example propylene glycol, Transutol®, and the like; an alcohol for providing softness for vesicle membrane and as a penetration enhancer, such as, for example, ethanol, isopropyl alcohol, and the like; cholesterol to provide stability to the vesicle membrane; and a vehicle as a gel former, such as carbonyl D934, and the like.

Solutions of the synthetic melanin nanoparticles as free base or pharmacologically acceptable salt can be prepared in water suitably mixed with a surfactant, such as hydroxypropyl cellulose. Dispersions can also be prepared in glycerol, liquid polyethylene glycols, and mixtures thereof and in oils. Under ordinary conditions of storage and use, these preparations can contain a preservative to prevent the growth of microorganisms.

Pharmaceutical compositions can be delivered via intranasal or inhalable solutions or sprays, aerosols or inhalants. Nasal solutions can be aqueous solutions designed to be administered to the nasal passages in drops or sprays. Nasal solutions can be prepared so that they are similar in many respects to nasal secretions. Thus, the aqueous nasal solutions usually are isotonic and slightly buffered to maintain a pH of 5.5 to 6.5. In addition, antimicrobial preservatives, similar to those used in ophthalmic preparations and appropriate drug stabilizers, if required, may be included in the formulation. Various commercial nasal preparations are known and can include, for example, antibiotics and antihistamines.

Oral formulations can include excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders. In some embodiments, oral pharmaceutical compositions will comprise an inert diluent or assimilable edible carrier, or they may be enclosed in hard or soft shell gelatin capsule, or they may be compressed into tablets, or they may be incorporated directly with the food of the diet. For oral therapeutic administration, the active compounds may be incorporated with excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 75% of the weight of the unit, or preferably between 25-60%. The amount of active compounds in such compositions is such that a suitable dosage can be obtained.

For parenteral administration in an aqueous solution, for example, the solution should be suitably buffered and the liquid diluent first rendered isotonic with sufficient saline or glucose. Aqueous solutions, in particular, sterile aqueous media, are especially suitable for intravenous, intramuscular, subcutaneous and intraperitoneal administration. For example, one dosage could be dissolved in 1 ml of isotonic NaCl solution and either added to 1000 ml of hypodermoclysis fluid or injected at the proposed site of infusion.

Sterile injectable solutions can be prepared by incorporating the synthetic melanin nanoparticles in the required amount in the appropriate solvent followed by filtered sterilization. Generally, dispersions are prepared by incorporating the various sterilized active ingredients into a sterile vehicle which contains the basic dispersion medium. Vacuum-drying and freeze-drying techniques, which yield a powder of the active ingredient plus any additional desired ingredients, can be used to prepare sterile powders for reconstitution of sterile injectable solutions. The preparation of more, or highly, concentrated solutions for direct injection is also contemplated. DMSO can be used as solvent for extremely rapid penetration, delivering high concentrations of the active agents to a small area.

The formulations of synthetic melanin nanoparticles can be presented in unit-dose or multi-dose sealed containers, such as ampules and vials. Thus, the composition can be in unit dosage form. In such form the preparation is subdivided into unit doses containing appropriate quantities of the active component. Thus, the compositions can be administered in a variety of unit dosage forms depending upon the method of administration.

The dosage and frequency (single or multiple doses) administered to a subject can vary depending upon a variety of factors, for example, whether the mammal suffers from another disease, and its route of administration; size, age, sex, health, body weight, body mass index, and diet of the recipient; nature and extent of symptoms of the melanin-defective disease being treated, kind of concurrent treatment, complications from the melanin-defective disease being treated or other health-related problems. Other therapeutic regimens or agents can be used in conjunction with the methods and compounds of the invention. Adjustment and manipulation of established dosages (e.g., frequency and duration) are well within the ability of those skilled in the art.

Target concentrations will be those concentrations of the synthetic melanin nanoparticles that are capable of achieving the methods described herein, as measured using the methods described herein or known in the art. As is well known in the art, effective amounts for use in humans can also be determined from animal models. For example, a dose for humans can be formulated to achieve a concentration that has been found to be effective in animals. The dosage in humans can be adjusted by monitoring effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient. The dose administered to a patient, in the context of the present invention should be sufficient to affect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred

EMBODIMENTS

Embodiment 1. A method for protecting a cell from ultraviolet (UV) damage, the method comprising contacting a cell with a synthetic melanin-nanoparticle, the synthetic melanin nanoparticle comprising one or more melanin polymers, wherein the synthetic melanin nanoparticle is capable of functioning as a pigment for the protection of the cell from UV damage.

Embodiment 2. A method for treating a melanin-defective disease in a subject in need thereof, the method comprising administering to the subject a synthetic melanin-nanoparticle, the synthetic melanin nanoparticle comprising one or more melanin polymers, wherein the synthetic melanin nanoparticle is capable of protecting the subject from UV damage.

Embodiment 3. The method of Embodiments 1 or 2, wherein the synthetic melanin nanoparticle is biocompatible.

Embodiment 4. The method of Embodiment 1, wherein the cell is a keratinocyte.

Embodiment 5. The method of Embodiments 1 or 2, wherein the one or more melanin polymers is not bound to, conjugated to, attached to, coated by, encompassed by or otherwise associated with a lipid.

Embodiment 6. The method of Embodiments 1 or 2, wherein the one or more melanin polymers is not bound to, conjugated to, attached to, coated by, encompassed by or otherwise associated with a proteinaceous lipid.

Embodiment 7. The method of Embodiments 1 or 2, wherein the one or more melanin polymers is a metal-binding melanin polymer.

Embodiment 8. The method of Embodiment 7, wherein the metal component of the metal-binding melanin polymer is a transition metal.

Embodiment 9. The method of Embodiment 8, wherein the transition metal is iron.

Embodiment 10. The method of Embodiments 1 or 2, wherein the one or more melanin polymers is a fused ring melanin polymer comprising a plurality of fused ring heteroaryl monomers.

Embodiment 11. The method of Embodiments 1 or 2, wherein the one or more melanin polymers is a fused ring melanin polymer comprising a plurality of fused ring heterocycloalkyl monomers.

Embodiment 12. The method of Embodiments 10 or 11, wherein the fused ring melanin polymer is a fused ring metal-binding melanin polymer.

Embodiment 13. The method of Embodiment 12, wherein the metal component of the metal-binding melanin polymer is a transition metal.

Embodiment 14. The method of embodiment 13, wherein the transition metal is iron.

Embodiment 15. The method of any one of Embodiments 10, 11 or 12, wherein the fused ring melanin polymers comprise a plurality of dopamine monomers.

Embodiment 16. The method of Embodiment 15, wherein the dopamine monomers are selected from the group consisting of dihydoxydopamine monomers, 3,4-dihydoxydopamine monomers, dioxydpoamine monomers and 3,4-dioxydopamine monomers.

Embodiment 17. The method of Embodiment 10, wherein the fused ring heteroaryl monomers are substituted with one or more substituents selected from the group consisting of hydroxyl and carboxyl.

Embodiment 18. The method of Embodiment 11, wherein the fused ring heterocycloalkyl monomers are substituted with one or more substituents selected from the group consisting of hydroxyl, carboxyl and oxy.

Embodiment 19. The method of Embodiments 10 or 11, wherein the fused ring heteroaryl monomers and/or fused ring heterocycloalkyl monomers are selected from the group consisting of indole monomers, benzothiazine monomers and benzothiazole monomers.

Embodiment 20. The method of Embodiment 19, wherein the indole monomers are selected from the group consisting of dihydroxyindole monomers, 5,6-dihydroxyindole (DHI) monomers, 5,6-dihydroxyindole-2-carboxylic acid monomers, dioxyindole monomers, 5,6-dioxyindole monomers, and 5,6-droxyindole-2-carboxylic acid monomers.

Embodiment 21. The method of Embodiment 17, wherein the fused ring heteroaryl monomers are a 6,6-fused ring heteroaryl monomer, a 5,6-fused ring heteroaryl monomer or a 6,5-fused ring heteroaryl monomer.

Embodiment 22. The method of Embodiment 21, wherein the fused ring heterocycloalkyl monomers are a 6,6-fused ring heterocycloalkyl monomer, a 5,6-fused ring heterocycloalkyl 1monomer or 6,5-fused ring heterocycloalkyl monomer.

Embodiment 23. The method of Embodiment 10, wherein the monomers are dihydroxy fused ring heteroaryl monomers.

Embodiment 24. The method of Embodiment 11, wherein the monomers are dihydroxy fused ring heterocycloalkyl monomers.

Embodiment 25. The method of Embodiments 23 or 24, wherein the monomers are a catechol fused ring monomer comprising hydroxy substituents attached to adjacent carbons of a 6 membered ring of the catechol fused ring monomer.

Embodiment 26. The method of Embodiments 10 or 11, wherein the fused ring melanin polymer is branched.

Embodiment 27. The method of Embodiments 1 or 2, wherein the phenethylamine polymer results from spontaneous oxidation of a plurality of phenethylamine molecules in an aqueous solution and under alkaline conditions.

Embodiment 28. The method of Embodiments 1 or 2, wherein the synthetic melanin nanoparticle is a sphere, a nanorod or a hollow sphere.

Embodiment 29. The method of Embodiment 28, wherein the synthetic melanin nanoparticle is a sphere.

Embodiment 30. The method of Embodiment 28, wherein the synthetic melanin nanoparticle is a hollow sphere.

Embodiment 31. The method of Embodiment 29, wherein the sphere comprises silica.

Embodiment 32. The method of Embodiments 1 or 2, wherein the synthetic melanin nanoparticle comprises at least one axis having a dimension of from about 1 nm to about 1000 nm.

Embodiment 33. The method of Embodiments 1 or 2, wherein the synthetic melanin nanoparticle comprises at least one axis having a dimension of from about 50 nm to about 500 nm.

Embodiment 34. The method of Embodiments 1 or 2, wherein the synthetic melanin nanoparticle comprises at least one axis having a dimension of from about 100 nm to about 300 nm.

Embodiment 35. The method of Embodiments 1 or 2, wherein the synthetic melanin nanoparticle comprises at least one axis having a dimension of from about 150 nm to about 250 nm.

Embodiment 36. The method of Embodiment 29, wherein the sphere is from about 150 nm to about 250 nm in average diameter.

Embodiment 37. The method of Embodiment 29, wherein the sphere is about 250 nm in average diameter.

Embodiment 38. The method of Embodiment 1, wherein the synthetic melanin nanoparticle undergoes endocytosis in the cell.

Embodiment 39. The method of Embodiment 1, wherein the synthetic melanin nanoparticle undergoes perinuclear aggregation in the cell.

Embodiment 40. The method of Embodiment 1, wherein the synthetic melanin nanoparticle comprises a supranuclear cap in the cell.

Embodiment 41. The method of Embodiments 1 or 2, wherein the damage is DNA damage.

Embodiment 42. The method of Embodiments 1 or 2, wherein the damage results from reactive oxygen species (ROS).

Embodiment 43. The method of Embodiments 1 or 2, wherein the synthetic melanin nanoparticle forms part of a synthetic melanin nanoparticle composition wherein the synthetic melanin nanoparticle is present at a concentration of from about 0.01 mg/ml to about 1.0 mg/ml within the synthetic melanin nanoparticle composition.

Embodiment 44. The method of Embodiments 1 or 2, wherein the synthetic melanin nanoparticle forms part of a synthetic melanin nanoparticle composition wherein the synthetic melanin nanoparticle is present at a concentration of from about 0.01 mg/ml to about 0.4 mg/ml within the synthetic melanin nanoparticle composition.

Embodiment 45. The method of Embodiments 1 or 2, wherein the synthetic melanin nanoparticle forms part of a synthetic melanin nanoparticle composition wherein the synthetic melanin nanoparticle is present at a concentration of about 0.02 mg/ml within the synthetic melanin nanoparticle composition.

Embodiment 46. The method of Embodiment 2, wherein the melanin-defective disease is vitiligo.

Embodiment 47. The method of Embodiment 2, wherein the melanin-defective disease is albinism.

Embodiment 48. The method of Embodiment 2, wherein the melanin-defective disease is skin cancer.

Embodiment 49. The method of Embodiment 2, wherein the synthetic melanin nanoparticle is administered topically.

Embodiment 50. The method of Embodiment 49, wherein the synthetic melanin nanoparticle is administered topically as a cream, gel, ointment, lotion, aerosol or liquid.

Embodiment 51. The method of Embodiment 49, wherein the synthetic melanin nanoparticle is administered topically with a transdermal patch.

Embodiment 52. The method of Embodiment 2, wherein the synthetic melanin nanoparticle is administered intravenously.

Embodiment 53. The method of Embodiment 2, wherein the synthetic melanin nanoparticle is administered orally.

Embodiment 54. The method of Embodiment 2, wherein the synthetic melanin nanoparticle is administered by injection.

Embodiment 55. The method of Embodiment 54, wherein the injection is by intraocular injection.

Embodiment 56. The method of Embodiment 54, wherein the injection is a localized injection.

Embodiment 57. The method of Embodiments 1 or 2, wherein the synthetic melanin nanoparticle is administered prior to, simultaneous with, or subsequent to UV exposure.

Embodiment 58. A pharmaceutical composition comprising a synthetic melanin nanoparticle and one or more pharmaceutically acceptable excipients, the synthetic melanin nanoparticle comprising one or more melanin polymers.

Embodiment 59. The pharmaceutical composition of Embodiment 58, wherein the synthetic melanin nanoparticle is biocompatible.

Embodiment 60. The pharmaceutical composition of Embodiment 58, wherein the one or more melanin polymers is not bound to, conjugated to, attached to, coated by, encompassed by or otherwise associated with a lipid.

Embodiment 61. The pharmaceutical composition of Embodiment 58, wherein the one or more melanin polymers is not bound to, conjugated to, attached to, coated by, encompassed by or otherwise associated with a proteinaceous lipid.

Embodiment 62. The pharmaceutical composition of Embodiment 58, wherein the one or more melanin polymers is a metal-binding melanin polymer.

Embodiment 63. The pharmaceutical composition of Embodiment 62, wherein the metal component of the metal-binding melanin polymer is a transition metal.

Embodiment 64. The pharmaceutical composition of Embodiment 63, wherein the transition metal is iron.

Embodiment 65. The pharmaceutical composition of Embodiment 58, wherein the one or more melanin polymers is a fused ring melanin polymer comprising a plurality of fused ring heteroaryl monomers.

Embodiment 66. The pharmaceutical composition of Embodiment 58, wherein the one or more melanin polymers is a fused ring melanin polymer comprising a plurality of fused ring heterocycloalkyl monomers.

Embodiment 67. The pharmaceutical composition of Embodiment 65 or 66, wherein the fused ring melanin polymer is a fused ring metal-binding melanin polymer.

Embodiment 68. The pharmaceutical composition of Embodiment 67, wherein the metal component of the fused ring metal-binding melanin polymer is a transition metal.

Embodiment 69. The pharmaceutical composition of Embodiment 68, wherein the transition metal is iron.

Embodiment 70. The pharmaceutical composition of Embodiment 58, wherein the fused ring melanin polymers comprise a plurality of dopamine monomers.

Embodiment 71. The pharmaceutical composition of Embodiment 70, wherein the dopamine monomers are selected from the group consisting of dihydoxydopamine monomers, 3,4-dihydoxydopamine monomers, dioxydpoamine monomers and 3,4-dioxydopamine monomers.

Embodiment 72. The pharmaceutical composition of Embodiment 65, wherein the fused ring heteroaryl monomers are substituted with one or more substituents selected from the group consisting of hydroxyl and carboxyl.

Embodiment 73. The pharmaceutical composition of Embodiment 66, wherein the fused ring heterocycloalkyl monomers are substituted with one or more substituents selected from the group consisting of hydroxyl, carboxyl and oxy.

Embodiment 74. The pharmaceutical composition of Embodiments 65 or 66, wherein the fused ring heteroaryl monomers and/or fused ring heterocycloalkyl monomers are selected from the group consisting of indole monomers, benzothiazine monomers and benzothiazole monomers.

Embodiment 75. The pharmaceutical composition of Embodiment 74, wherein the indole monomers are selected from the group consisting of dihydroxyindole monomers, 5,6-dihydroxyindole (DHI) monomers, 5,6-dihydroxyindole-2-carboxylic acid monomers, dioxyindole monomers, 5,6-dioxyindole monomers, and 5,6-droxyindole-2-carboxylic acid monomers.

Embodiment 76. The pharmaceutical composition of Embodiment 65, wherein the fused ring heteroaryl monomers are a 6,6-fused ring heteroaryl monomer, a 5,6-fused ring heteroaryl monomer or a 6,5-fused ring heteroaryl monomer.

Embodiment 77. The pharmaceutical composition of Embodiment 66, wherein the fused ring heterocycloalkyl monomers are a 6,6-fused ring heterocycloalkyl monomer, a 5,6-fused ring heterocycloalkyl 1monomer or 6,5-fused ring heterocycloalkyl monomer.

Embodiment 78. The pharmaceutical composition of Embodiment 65, wherein the monomers are dihydroxy fused ring heteroaryl monomers.

Embodiment 79. The pharmaceutical composition of Embodiment 66, wherein the monomers are dihydroxy fused ring heterocycloalkyl monomers.

Embodiment 80. The pharmaceutical composition of Embodiments 78 or 79, wherein the monomers are a catechol fused ring monomer comprising hydroxy substituents attached to adjacent carbons of a 6 membered ring of the catechol fused ring monomer.

Embodiment 81. The pharmaceutical composition of Embodiment 58, wherein the fused ring melanin polymer is branched.

Embodiment 82. The pharmaceutical composition of Embodiment 58, wherein the synthetic melanin nanoparticle is a sphere, a nanorod or a hollow sphere.

Embodiment 83. The pharmaceutical composition of Embodiment 82, wherein the synthetic melanin nanoparticle is a sphere.

Embodiment 84. The pharmaceutical composition of Embodiment 82, wherein the synthetic melanin nanoparticle is a hollow sphere.

Embodiment 85. The pharmaceutical composition of Embodiment 82, wherein the sphere comprises silica.

Embodiment 86. The pharmaceutical composition of Embodiment 58, wherein the synthetic melanin nanoparticle comprises at least one axis having a dimension of from about 1 nm to about 1000 nm.

Embodiment 87. The pharmaceutical composition of Embodiment 58, wherein the synthetic melanin nanoparticle comprises at least one axis having a dimension of from about 50 nm to about 500 nm.

Embodiment 88. The pharmaceutical composition of Embodiment 58, wherein the synthetic melanin nanoparticle comprises at least one axis having a dimension of from about 100 nm to about 300 nm.

Embodiment 89. The pharmaceutical composition of Embodiment 58, wherein the synthetic melanin nanoparticle comprises at least one axis having a dimension of from about 150 nm to about 250 nm.

Embodiment 90. The pharmaceutical composition of Embodiment 58, wherein the pharmaceutical composition is a topical formulation.

Embodiment 91. The pharmaceutical composition of Embodiment 90, wherein the topical formulation is in the form of a gel.

Embodiment 92. The pharmaceutical composition of Embodiment 90, wherein the topical formulation is in the form of a cream.

Embodiment 93. The pharmaceutical composition of Embodiment 90, wherein the topical formulation is in the form of a lotion.

Embodiment 94. The pharmaceutical composition of Embodiment 90, wherein the topical formulation is in the form of an ointment.

Embodiment 95. The pharmaceutical composition of Embodiment 90, wherein the topical formulation is in the form of an aerosol.

Embodiment 96. The pharmaceutical composition of Embodiment 90, wherein the topical formulation is in the form of a liquid.

Embodiment 97. The pharmaceutical composition of Embodiment 90, wherein the topical formulation is suitable for administration with a transdermal patch.

Embodiment 98. The pharmaceutical composition of Embodiment 58, wherein the pharmaceutical composition is suitable for injection.

Embodiment 99. The pharmaceutical composition of Embodiment 98, wherein the injection is an intraocular injection.

Embodiment 100. The pharmaceutical composition of Embodiment 98, wherein the injection is a localized injection.

Further Embodiments

P-Embodiment 1. A biocompatible melanin-like nanoparticle (MelNP), the MelNP capable of mimicking the physiological function of a naturally occurring melanosome, the MelNP comprising a dopamine polymer.

P-Embodiment 2. The MelNP according to P-Embodiment 1, wherein the dopamine polymer results from spontaneous oxidation of a plurality of dopamine molecules in an aqueous solution.

P-Embodiment 3. The MelNP according to P-Embodiment 2, wherein the spontaneous oxidation is conducted under alkaline conditions.

P-Embodiment 4. The MelNP according to P-Embodiment 1, wherein the MelNP is a sphere, a nanorod or a hollow sphere.

P-Embodiment 5. The MelNP according to P-Embodiment 1, wherein the MelNP can undergo endocytosis in a keratinocyte.

P-Embodiment 6. The MelNP according to P-Embodiment 1, wherein the MelNP can undergo perinuclear aggregation in a keratinocyte.

P-Embodiment 7. The MelNP according to P-Embodiment 1, wherein the MelNP can comprise a supranuclear cap in a keratinocyte.

P-Embodiment 8. A method for protecting a cell from ultraviolet (UV) induced damage, the method comprising contacting a cell with a biocompatible melanin-like nanoparticle (MelNP) under conditions suitable to afford uptake of the MelNP into the cell, thereby protecting the cell from the UV damage.

P-Embodiment 9. The method according to P-Embodiment 8, wherein the cell is a keratinocyte.

P-Embodiment 10. The method according to P-Embodiment 8, wherein the damage is DNA damage P-Embodiment 11. The method according to P-Embodiment 8, wherein the damage results from reactive oxygen species (ROS).

EXAMPLES

A primary role of melanin in skin is the prevention of UV-induced nuclear DNA damage to human skin cells, where it serves to screen out harmful UV radiation. Melanin is delivered to keratinocytes in the skin after being excreted as melanosomes from melanocytes. Defects in melanin production in humans can cause diseases, many of which currently lack effective treatments due to their genetic origins (e.g. skin cancer, vitiligo and albinism). The widespread prevalence of melanin-related diseases and an increasing interest in the performance of various polymeric materials related to melanin necessitates novel synthetic routes for preparing melanin-like materials.

Natural melanins are found across animal and plant kingdoms, where they perform various biological functions, including photoprotection, photosensitization, free radical quenching, metal ion chelation, and neuroprotection in the central nervous system of humans. [1] Several types of melanins exist in the human body, including eumelanin[2], pheomelanin[3] and neuromelanin.[4] Eumelanin is the most common, primarily determining the color of human skin. More importantly, it is able to prevent UV-induced nuclear DNA damage of human skin cells by screening out harmful UV radiation. [5] Solar UV radiation is absorbed by DNA and damages nuclei in epidermal cells, which can lead to the formation of mutations and subsequent, irrecoverable damage. In the basal layer of the epidermis, specialized melanocytes produce melanin-containing organelles, termed melanosomes, in which melanin is synthesized and deposited. [6] In skin, melanosomes are transferred from melanocytes to neighboring keratinocytes to form perinuclear melanin caps. [7,8] The melanosomes accumulate around the nuclei in the form of melanin caps for the mitigation of UV damage to DNA. Indeed, people are generally familiar with the process by which exposure to UV-radiation causes melanogenesis, observed as a change in skin color commonly referred to as tanning. [9] The integrated biological system for the induction, production, transfer and degradation of melanosomes is significant for the health of human skin, with melanin-defective diseases, such as vitiligo and albinism highlighting the importance of these processes. For example, vitiligo develops when the immune system wrongly attempts to clear normal melanocytes from the skin, effectively stopping the production of melanosomes. [10,11] Albinism is caused by genetic defects causing the failure of a copper-containing tyrosinase involved in the production of melanin. [12,13] Both diseases lack effective treatments and they both promote significant risk of skin cancer in patients.

Water-dispersible, melanin-like nanoparticles (MelNPs) with high biocompatibility have been investigated for various biomedical applications, including as iron-chelated Ti-weighted MRI contrast agents,[14] and in targeted therapeutic and bio-responsive applications. [15] MelNPs are prepared synthetically via the spontaneous oxidative polymerization of dopamine under alkaline conditions in aqueous solution. [16] By contrast, biosynthetic melanins are formed in epidermal melanocytes involving tyrosinase-catalyzed oxidative polymerization of tyrosine,[17] giving rise to black, insoluble eumelanins. Both synthetic and biosynthetic melanins appear to consist of largely planar oligomeric scaffolds.[18] MelNPs can be prepared in a variety of sizes and shapes, including spheres,[14] nanorods,[19] and hollow spheres. [20,21] These various morphologies are prevalent in nature, such as in bird feathers, where they play a shape- and packing-dependent role as iridescent structural color elements. [22] However, extraction of melanins from natural sources can be problematic and potentially more complex than direct synthetic routes. Therefore, synthetic MelNPs have been used as models for exploring the function and mechanism of natural eumelanins. For example, our own work on MelNPs has shown that synthetic forms can be used to mimic the performance of bird feathers in terms of structural coloration, and the materials themselves can be prepared in a facile and precisely controllable manner.[23]

Without being bound by theory, we hypothesized that synthetic melanin nanoparticles (MelNPs) would mimic naturally occurring melanosomes and be taken up by keratinocytes and transported intracellularly, providing photoprotection by adopting the same kind of perinuclear melanin cap in human epidermal keratinocytes as is observed for natural melanin. This hypothesis was predicated on two known facts. Firstly, the process of transfer of melanosomes from melanocytes to keratinocytes can occur when these two cell types are co-cultured in vitro. [6,24] Secondly, synthetic fluorescent microspheres had been used to establish the role of the dynactin p150Glucd subunit as a required part of the cellular machinery for keratinocytes in which the knock out showed a lack of microparasol formation. [25]

Figure 2E:
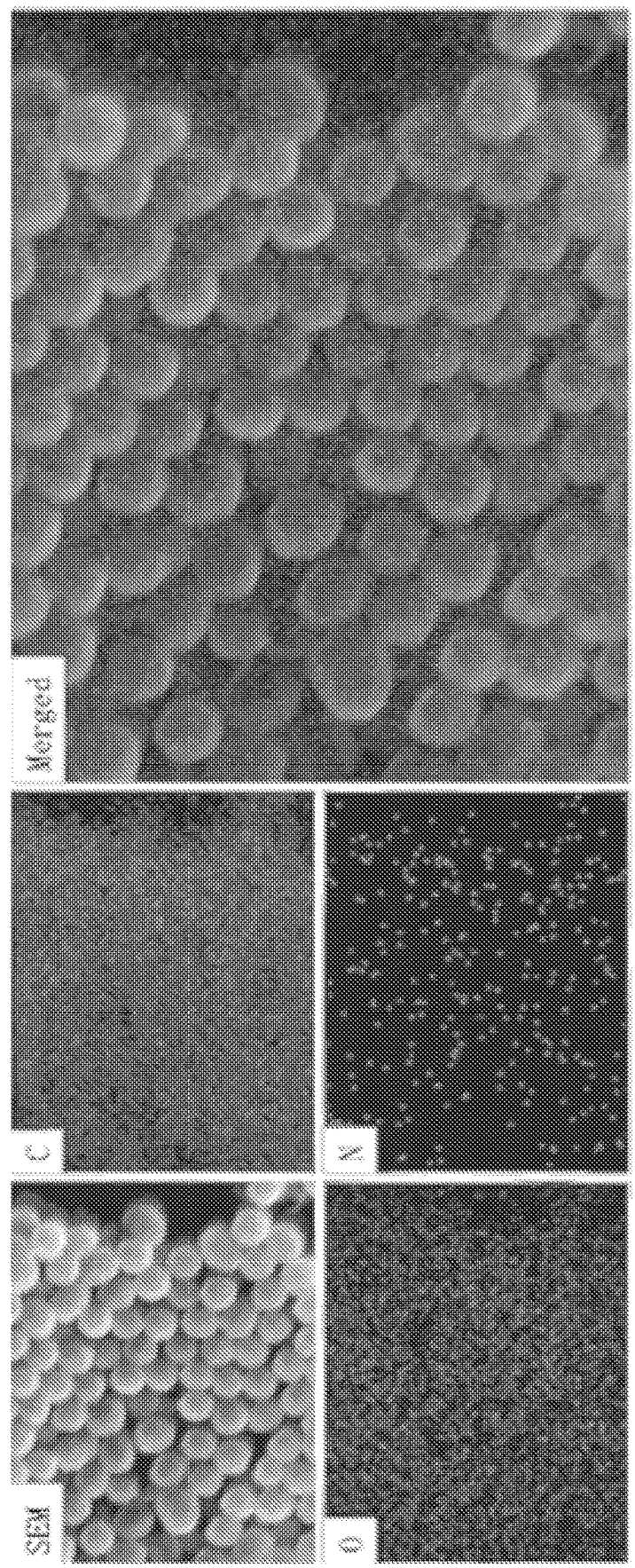
FIG. 2E. Energy-dispersive X-ray (EDX) mapping of MelNPs. SEM: scanning electron microscope results: C: carbon: O: oxygen; N: nitrogen; Merged: EDX mapping merged with C, O and N results.
Figure 3C:
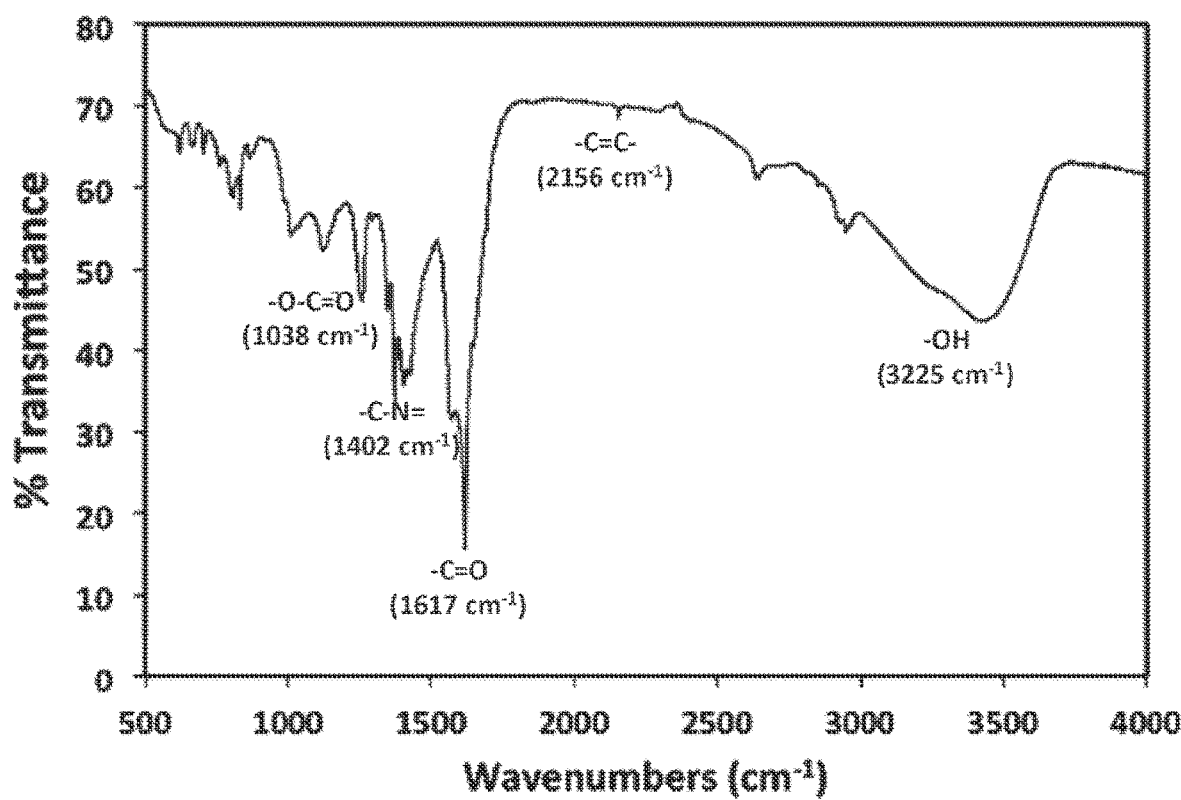
FIG. 3C. Fourier Transform Infrared Spectroscopic (FTIR) measurement of MelNPs.
Figure 4:
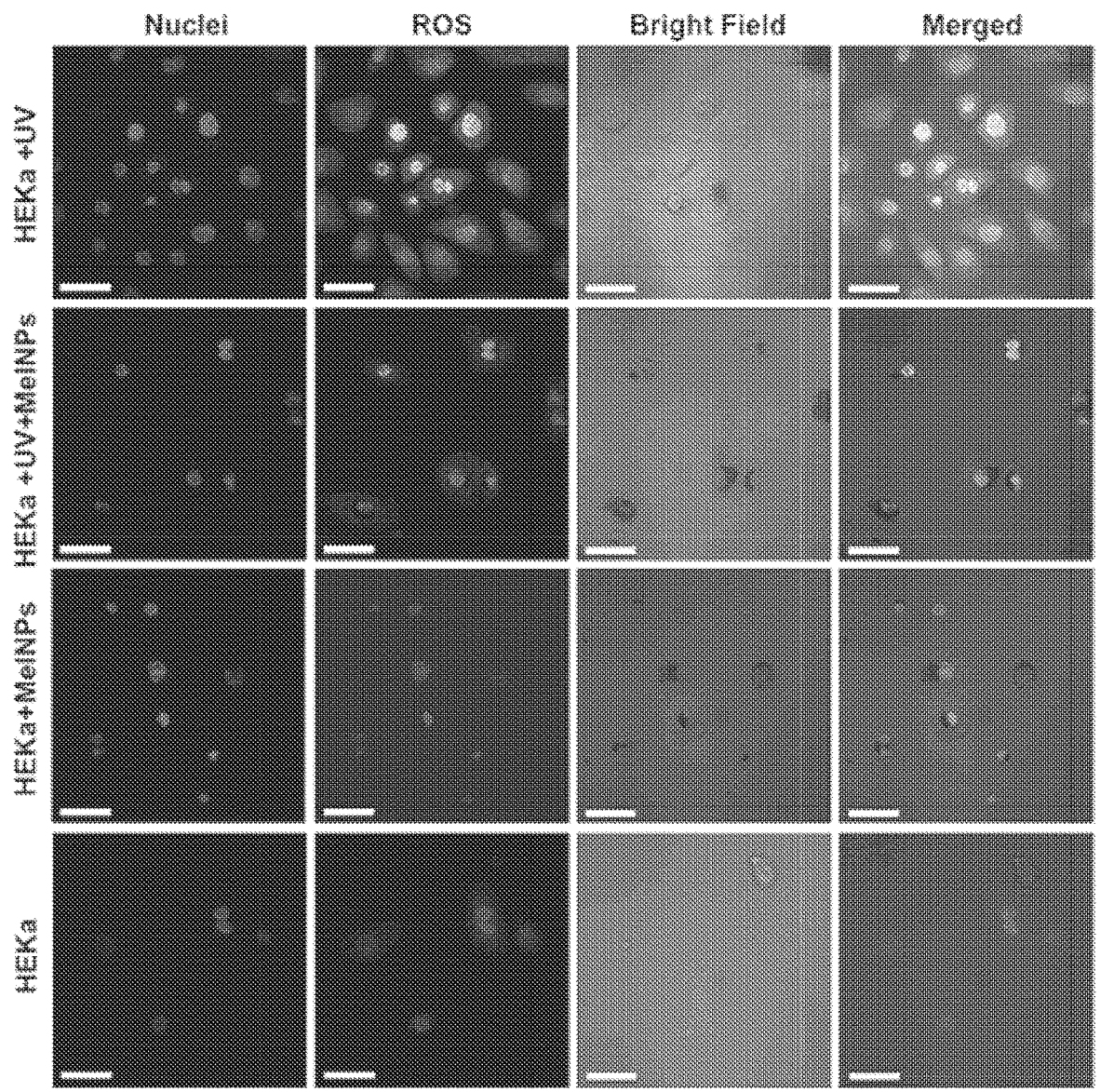
FIG. 4. Confocal imaging for ROS detection in HEKa cells with/without MelNPs and with/without UV irradiation. The nuclei were stained with NucBlue: ROS generated in HEKa cells were detected with DCFH-DA. Scale bars are 40μm.
Figure 4A:
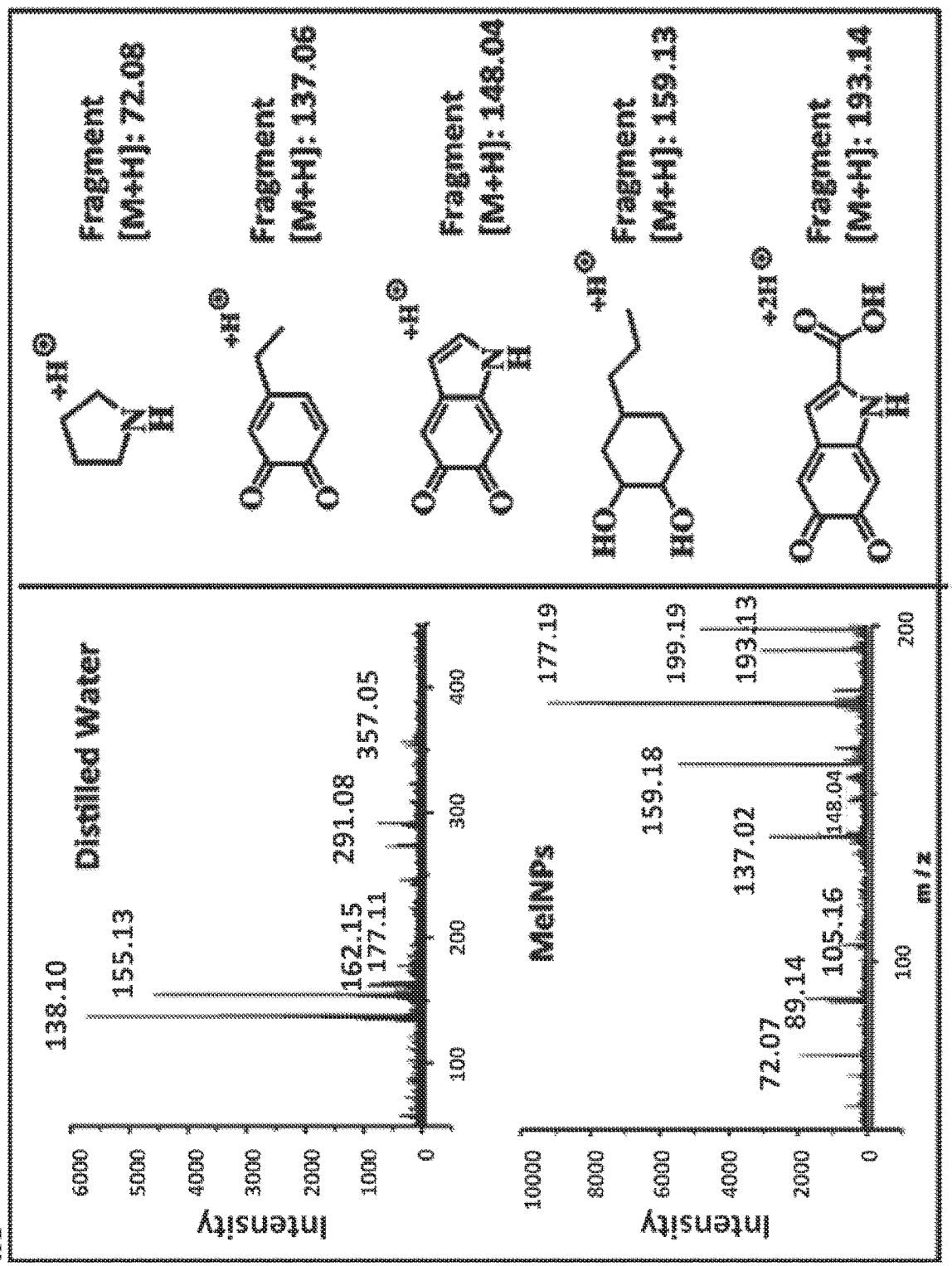
FIG. 4A. Matrix assisted laser desorption/ionization time of flight mass spectroscopic (MALDI-TOF MS) spectrum of distilled water and MelNPs, and structures consistent with masses observed in the spectrum.

To test our hypothesis, we first synthesized spherical MelNPs by spontaneous oxidization of dopamine under alkaline conditions, introducing aqueous ammonia to an aqueous solution of monomers (FIG. 1). The resulting spherical MelNPs showed a narrow size distribution around 200 nm, demonstrated by dynamic light scattering (DLS) (FIG. 1E), transmission electron microscopy (TEM) and scanning electron microscopy (SEM). Moreover, Energy Dispersive X-ray (EDX) measurements demonstrated that the elemental composition (C, N, O) and distribution in MelNPs (FIG. 2E) matches natural eumelanin. Additionally, Fourier transform infrared spectroscopy (FTIR) of MelNPs showed signals consistent with natural eumelanin including carboxylic acids (1038 $cm^{-1}$), hydroxyls (3225 $cm^{-1}$), —C=O (1617 $cm^{-1}$), —C=C— bond (2156 $cm^{-1}$) and —C=N=bond (1402 $cm^{-1}$) (FIG. 3C).[26] Eumelanin in the condensed phase and in solution has a well-known, broad-band monotonic absorbance, including in the ultraviolet and the visible range. [27] Aqueous solutions of MelNPs appeared black in color (FIG. 1, inserted picture) with a broad absorption in the UV-vis spectrum from 250 to 850 nm, consistent with eumelanin extracted from natural organelles. [27] To gain insight into the chemical structure of the particles, the MelNPs were analyzed using MALDI-TOF mass spectrometry. The signals with high intensities revealed oligomeric structures of both 5,6-dihydroxyindole (DHI) and 5,6-dihydroxyindole-2-carboxylic acid (DHICA) (FIG. 4A). Similar monomeric units have been observed previously by MALDI-MS analyses of natural sepia eumelanin. [28,29] The combined results illustrate that synthetic MelNPs exhibit similar chemical composition with natural eumelanin.

Figure 2A:
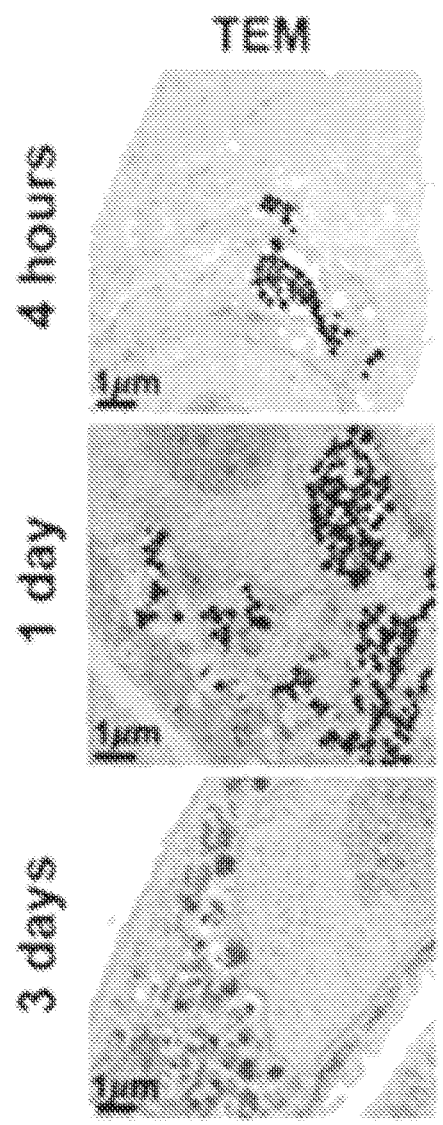
FIGS. 2A-2D. Imaging the uptake and cellular distribution of MelNPs in HEKa cells.
Figure 6:
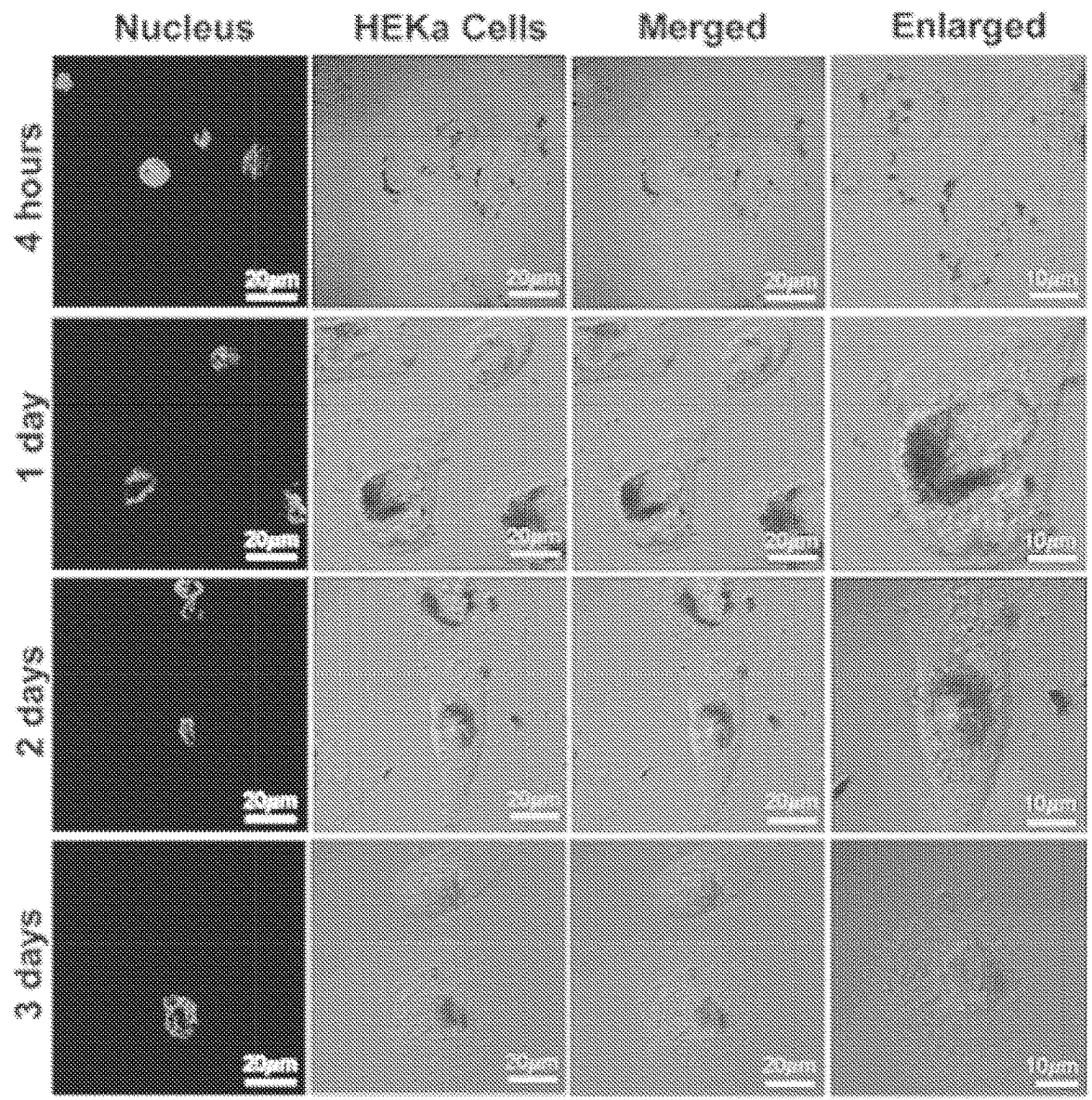
FIG. 6. Confocal images for HEKa cells incubated with 0.02 mg/ml MelNPs for 4 hours, 1 day, 2 days and 3 days, respectively, top to bottom. Nuclei of HEKa cells were stained by NUCBLUE®; MelNPs were black in HEKa cells under bright field microscopy.
Figure 7:
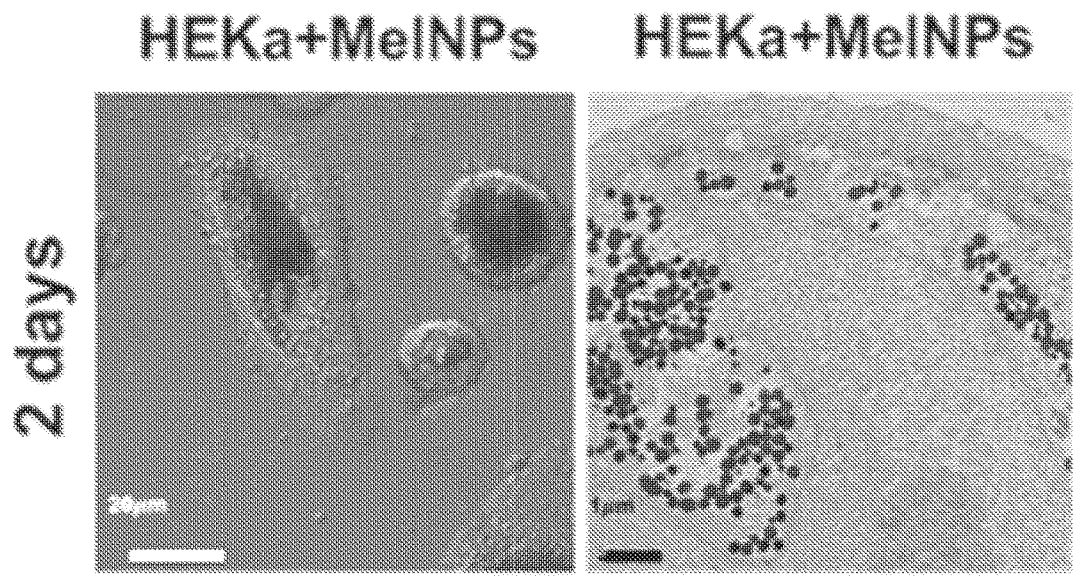
FIG. 7. Confocal image (left) and stained TEM image (right) of HEKa cells after incubating with 0.02 mg/mL MelNPs for 2 days. Nuclei of HEKa cells were stained by NUCBLUE®; MelNPs were black in HEKa cells under bright field microscopy.
Figure 8:
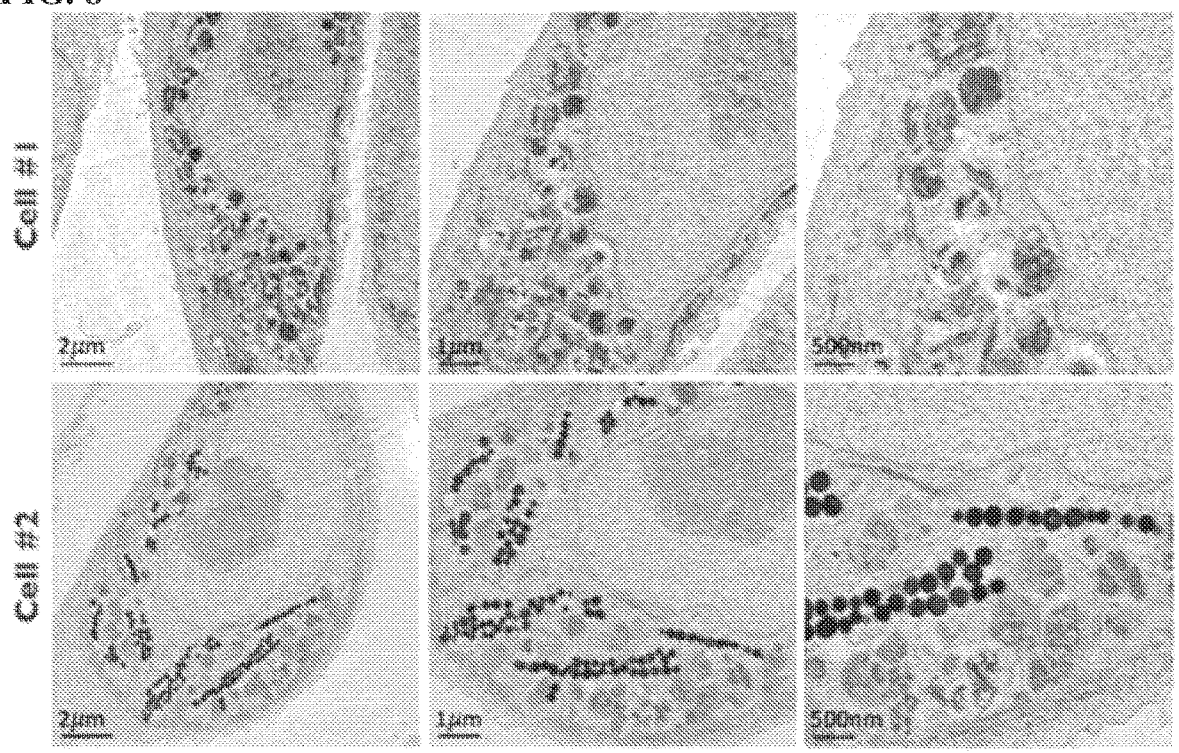
FIG. 8. Stained TEM images at different magnifications of HEKa cells incubated with 0.02 mg/mL MelNPs for 3 days.
Figure 9:
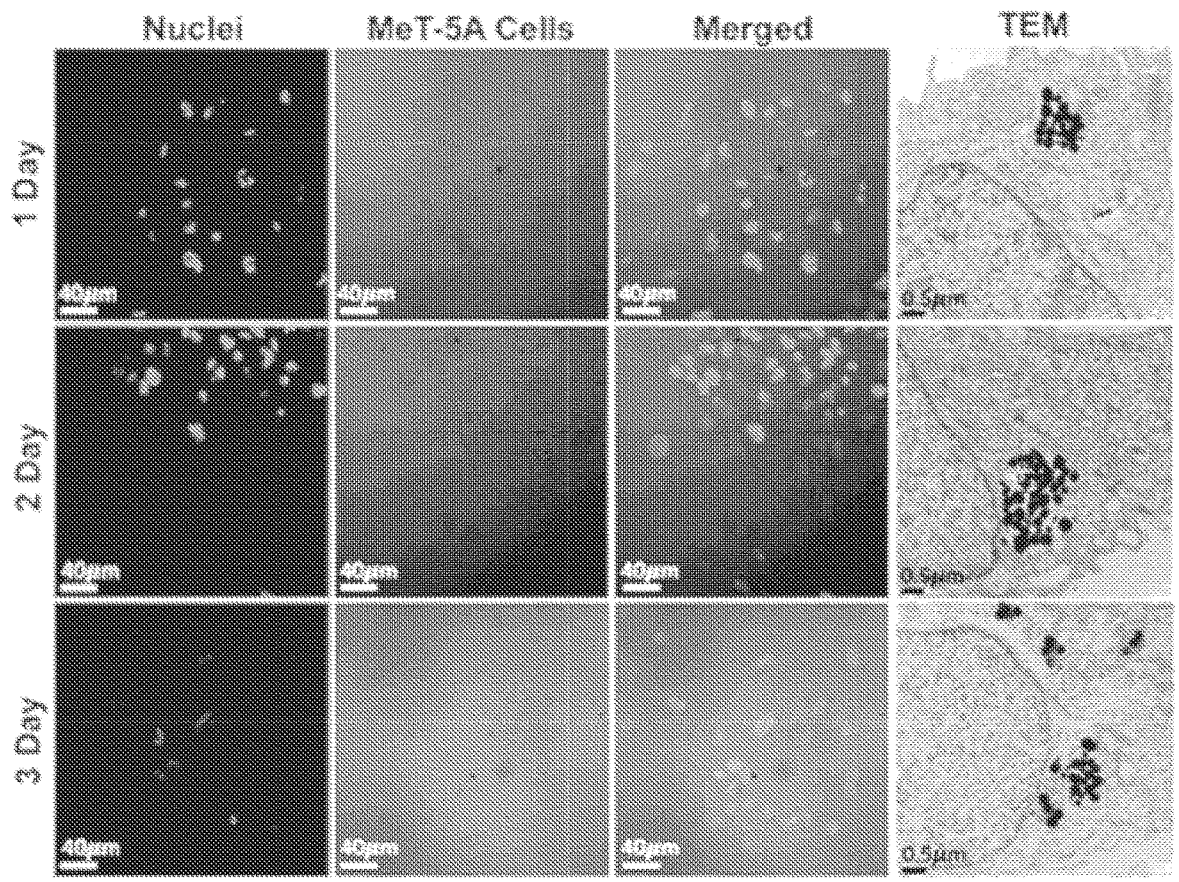
FIG. 9. Confocal images and stained TEM images of the time-dependent uptake of 0.02 mg/mL MelNPs in MeT-5A cells at 1, 2 and 3 days respectively. Nuclei of MeT-5A cells were stained by NUCBLUE®; MelNPs were black in HEKa cells under bright field microscopy.
Figure 10A:
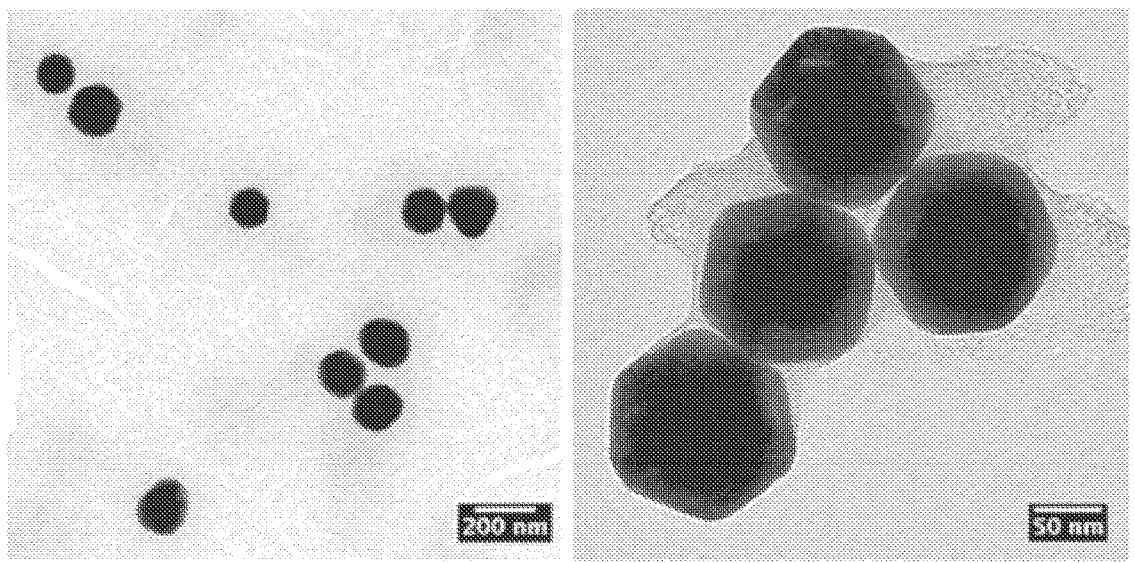
FIGS. 10A-10C. Characterization of AuNPs.
Figure 10B:
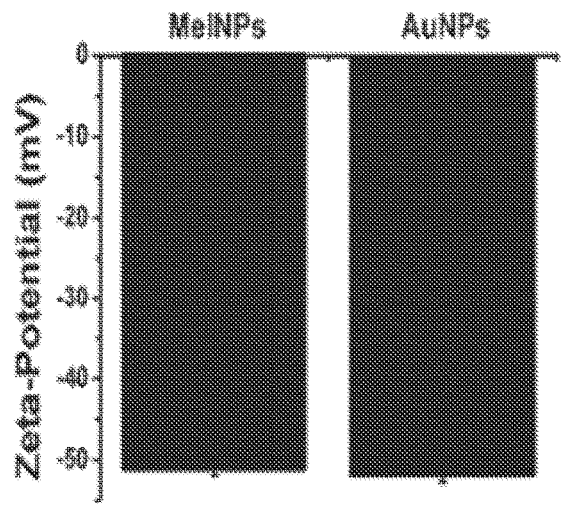
Figure 10C:
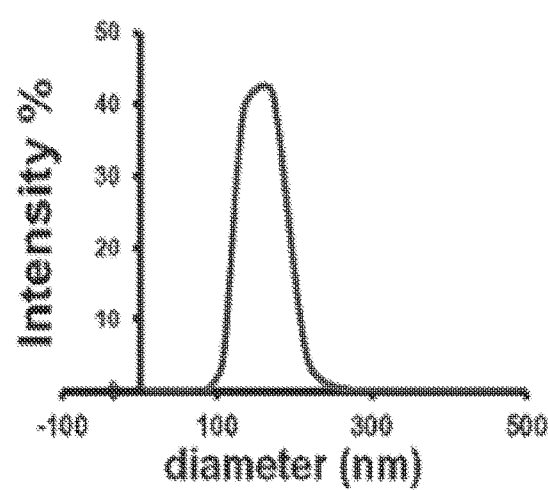
Figure 11:
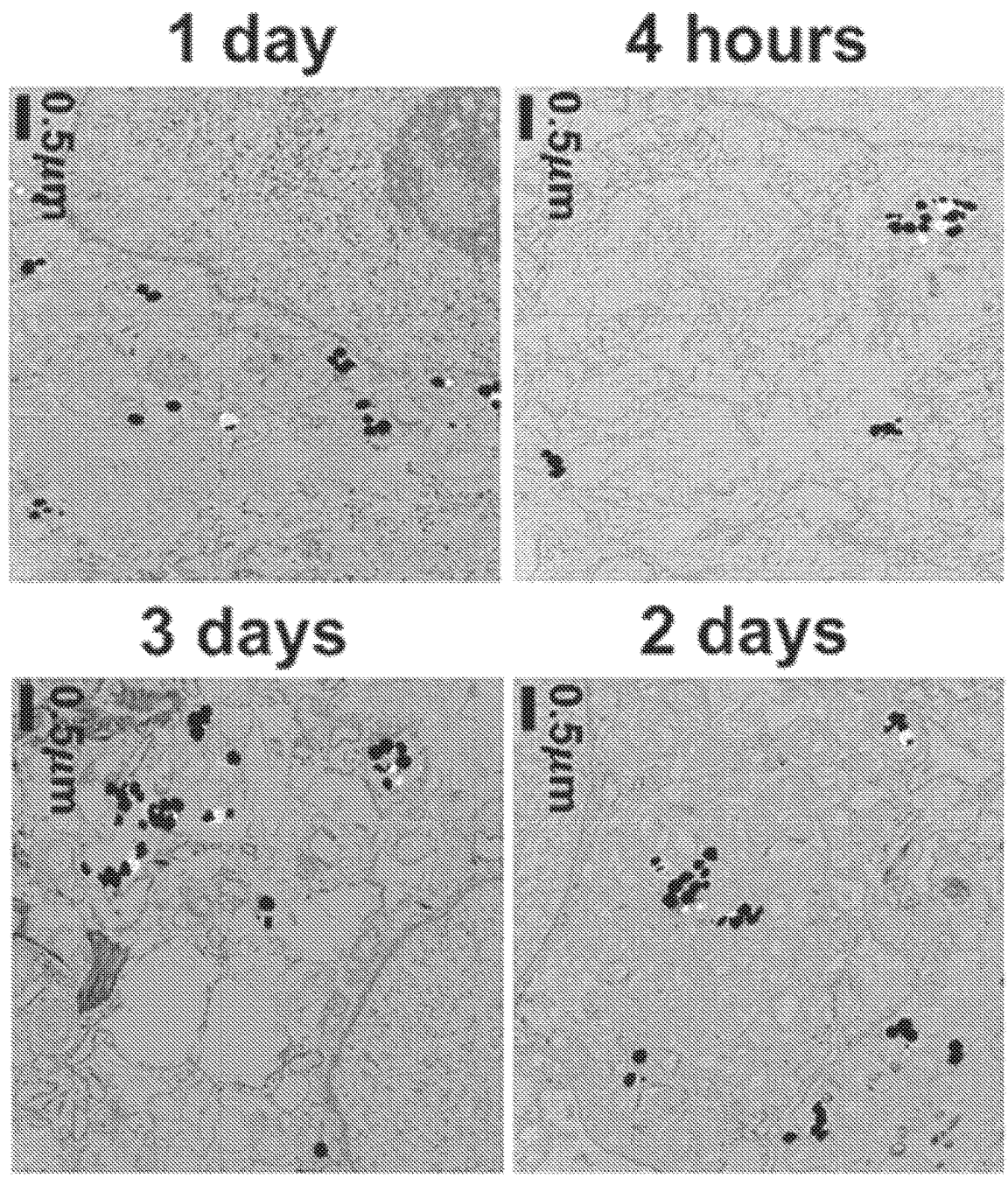
FIG. 11. Stained TEM images of HEKa cells incubated with AuNPs for 4 hours, 1 day, 2 days and 3 days as indicated, showing random distribution of AuNPs in HEKa cells.

Uptake of synthetic MelNPs into human epidermal keratinocytes (HEKa) was first examined with respect to the concentration dependence (FIG. 4A) and time dependence of the process. Initially, MelNPs at concentrations of 0.4 mg/ml, 0.1 mg/ml and 0.02 mg/ml were incubated with HEKa cells for 4 hours. TEM images of the cells indicated MelNPs were taken up. However, some MelNPs tended to adhere to the cell membrane at high concentrations (0.4 and 0.1 mg/ml). Therefore, a concentration of 0.02 mg/ml was chosen for subsequent experiments. In a prior study, Ichihashi et al. extracted natural melanosomes from melanocytes and studied their interactions with keratinocytes. It was shown that the melanosomes are gradually degraded, leading to the melanin being dispersed around the nucleus of the keratinocytes asymmetrically in a process occurring over the time course of 24 hours. [8] Therefore, to test whether MelNPs showed similar behavior, they were incubated at 0.02 mg/ml, with HEKa cells and observed at 4 hours, 1 day, 2 days and 3 days (FIG. 2). MelNPs were observed as black regions under bright-field confocal microscopy. At 4 hours the confocal images revealed MelNPs (black) surrounding the nuclei (blue), with others distributed in the cytoplasm, which was consistent with TEM data (FIG. 2, FIG. 6). However, after 1 day of incubation, melanin accumulated unevenly in the perinuclear area in a manner that appears consistent with observations of natural melanosomes. After 3 days incubation, the MelNPs showed clear signs of morphological transformation (FIG. 2A, FIG. 6 and FIG. 7 for 2 day data). Further, we observed that the transformed MelNPs and spherical MelNPs exist in some HEKa cells simultaneously, which may be caused by sequential order of uptake into cells, or the time course of processing (FIG. 8). To examine whether these processes were inherent to the MelNPs within keratinocytes, we incubated the particles with mesothelial cells (MeT-5A), chosen as a control epithelial cell-type distributed within tissues that do not normally take up and process melanosomes. [30] At the same time points, MelNPs lacked any specific trafficking or localization indicating a random distribution in the cytoplasm (FIG. 9). In addition, gold nanoparticles (AuNPs) with a similar size and surface charge to the MelNPs (FIG. 10) were incubated with HEKa cells, again showing random dispersion, rather than specific localization (FIG. 11). This suggests that the transport process is in some way dependent on particle type, and that the chemistry of the MelNPs plays a role in governing the cellular distribution pattern. [25]

Figure 2B:
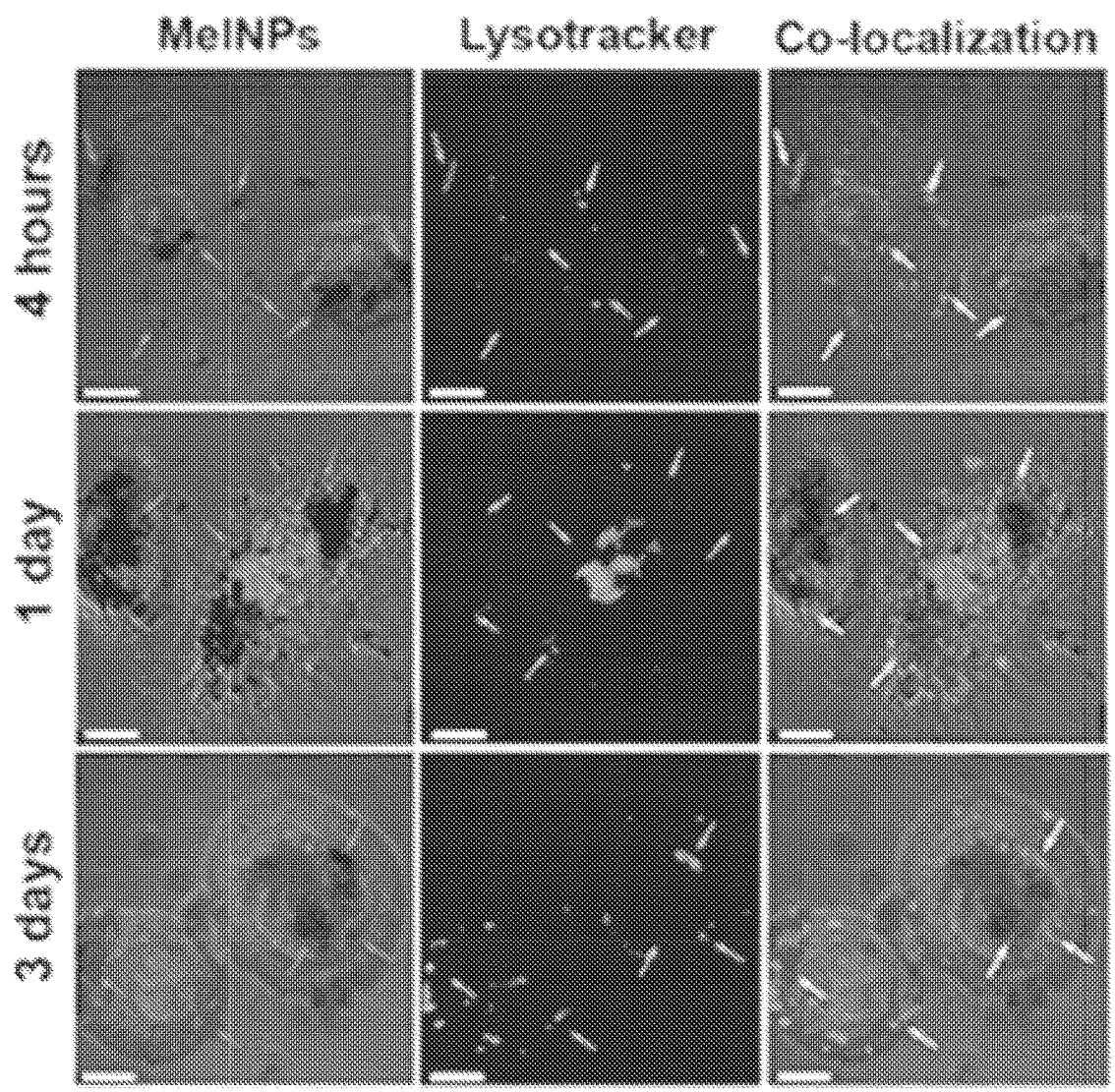
Figure 2C:
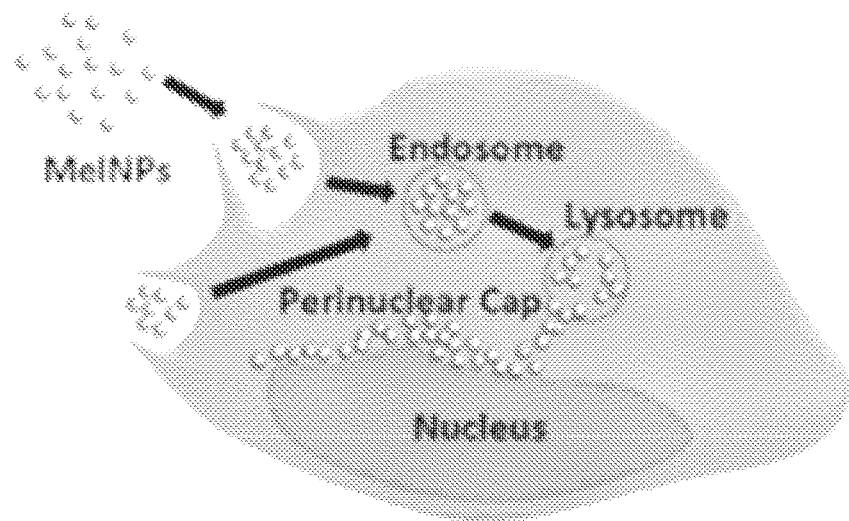
Figure 2D:
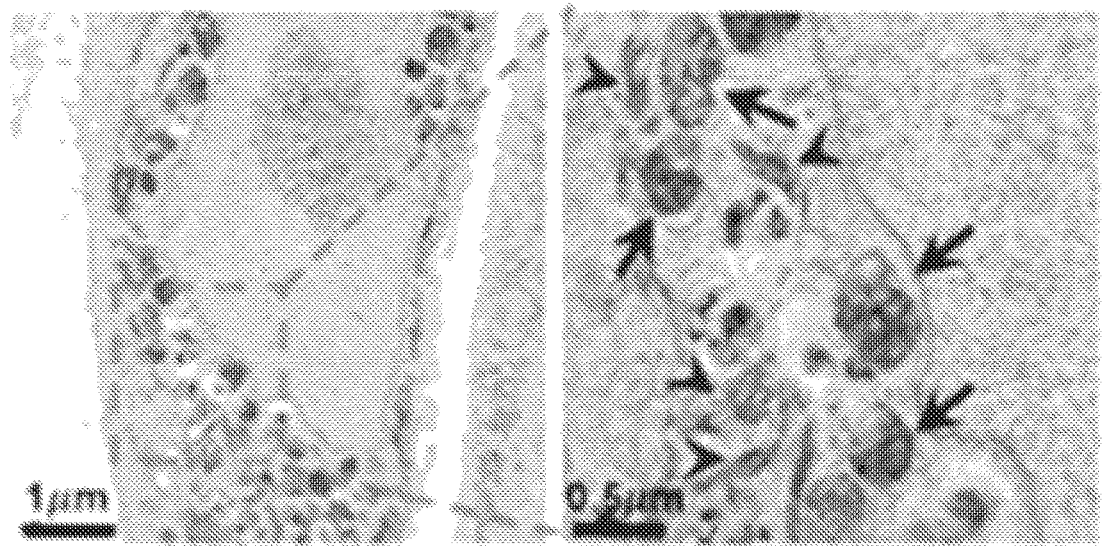

Melanosomes are tissue-specific, lysosome-related organelles of pigment cells in which melanins are synthesized and stored. [31,32] In epidermal melanocytes, melanosomes are ultimately transported to neighboring keratinocytes, which retain the melanin while in the basal layer and degrade as they move to the skin surface and differentiate. [33] The melanosome is characterized as a lysosome-related organelle because melanin must be synthesized and polymerized with the help of enzymes and structural proteins within the organelle, where acidic pH seems to be required. [34,35] We hypothesized the transportation and degradation of MelNPs was similarly driven by a lysosomal process in HEKa cells. To test this hypothesis, we investigated the possible co-localization of lysosomes and MeNPs. We incubated MelNPs with HEKa cells for 4 hours, 1 day and 3 days, and stained for lysosomes (LYSGTRACKER®, Red DND-99, red, FIG. 2). Confocal fluorescence microscopy images show the co-localization of lysosome and melanin (FIG. 2B). Therefore, MelNPs might utilize a similar pathway to natural melanosomes, undergoing lysosome-induced degradation and subsequent accumulation to form an artificial perinuclear cap (evident in FIG. 2C). After 4 hours of incubation, MelNPs appear as clusters in the cytosol surrounded by a membrane (FIG. 2A). After 3 days, MelNPs in cells were observed by TEM, without a surrounding membrane in the cytosol and dispersed among keratin fibers (FIG. 2D). Similar phenomena were observed when treating keratinocytes with extracted natural melanosomes, [8] supporting our conclusion that the MelNPs perform as artificial melanosomes utilizing the same transportation and degradation pathway as natural melanosomes.

Figure 3A:
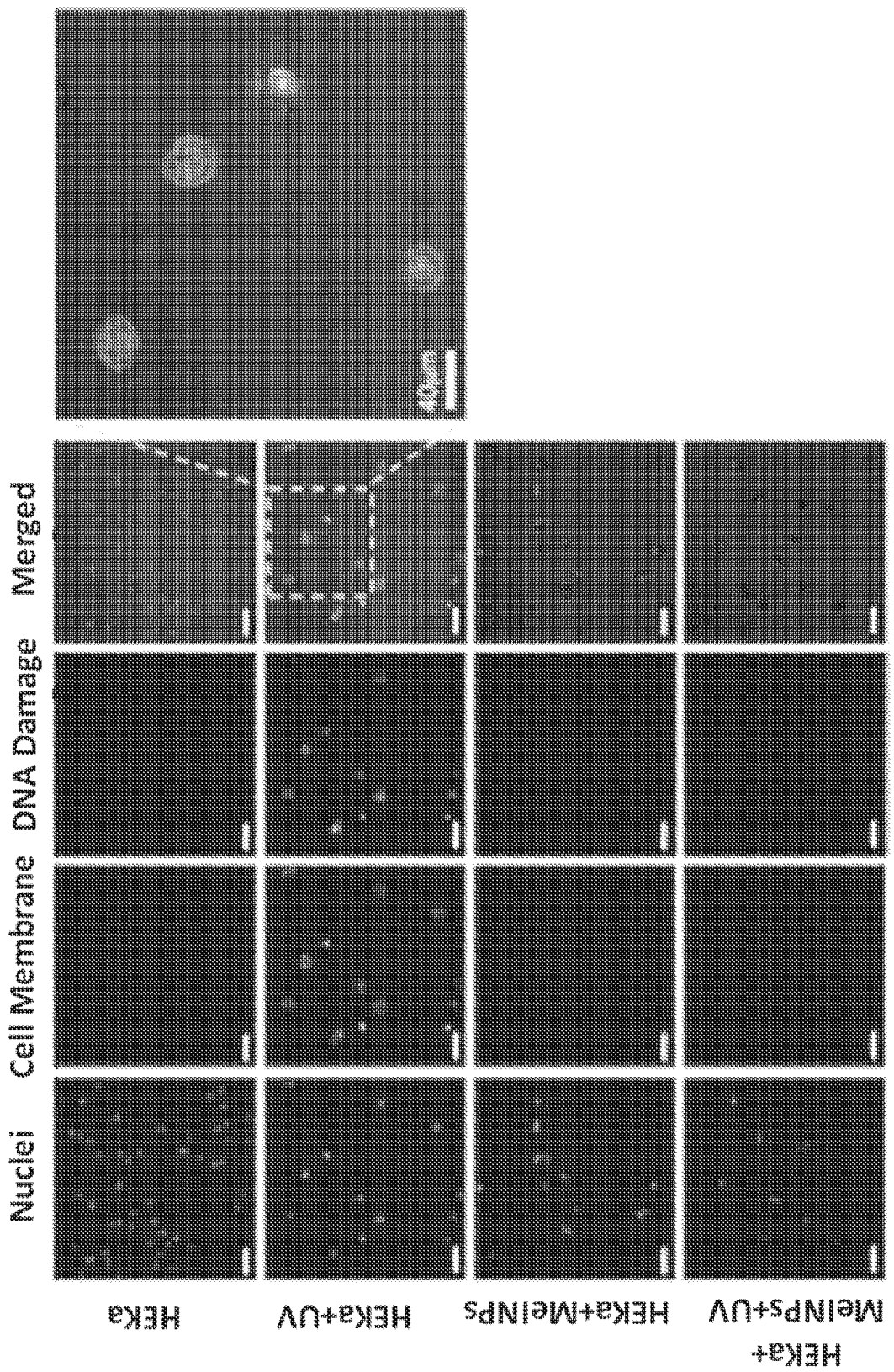
FIGS. 3A-3B. Evaluation of MelNPs as protective materials against UV damage to keratinocytes.
Figure 3B:
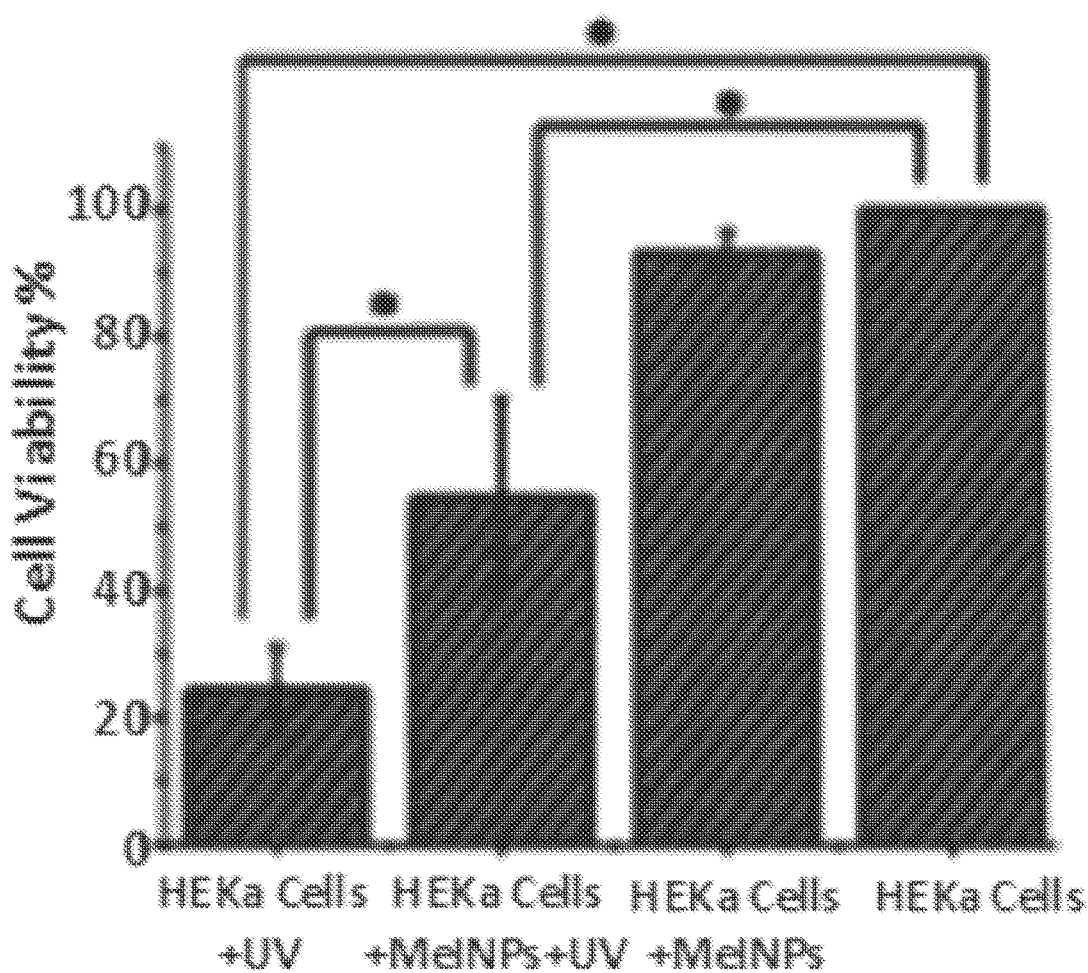
Figure 13:
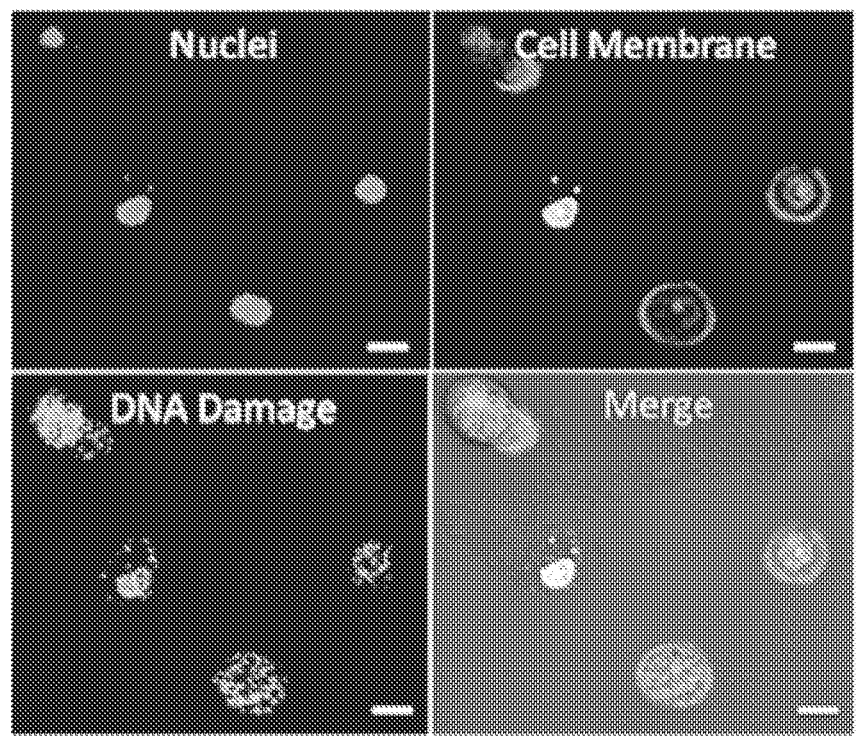
FIG. 13. Confocal microscopy images of HEKa cells irradiated by UV Nuclei were stained by Hochest 33342. Ceil membranes were stained by IMAGE-IT® DEAD GREEN™. Damaged DNA was stained by antibody against phosphorylated H2ax labeled with Alexa Fluor 555. Scale bars are 40μm.
Figure 14:
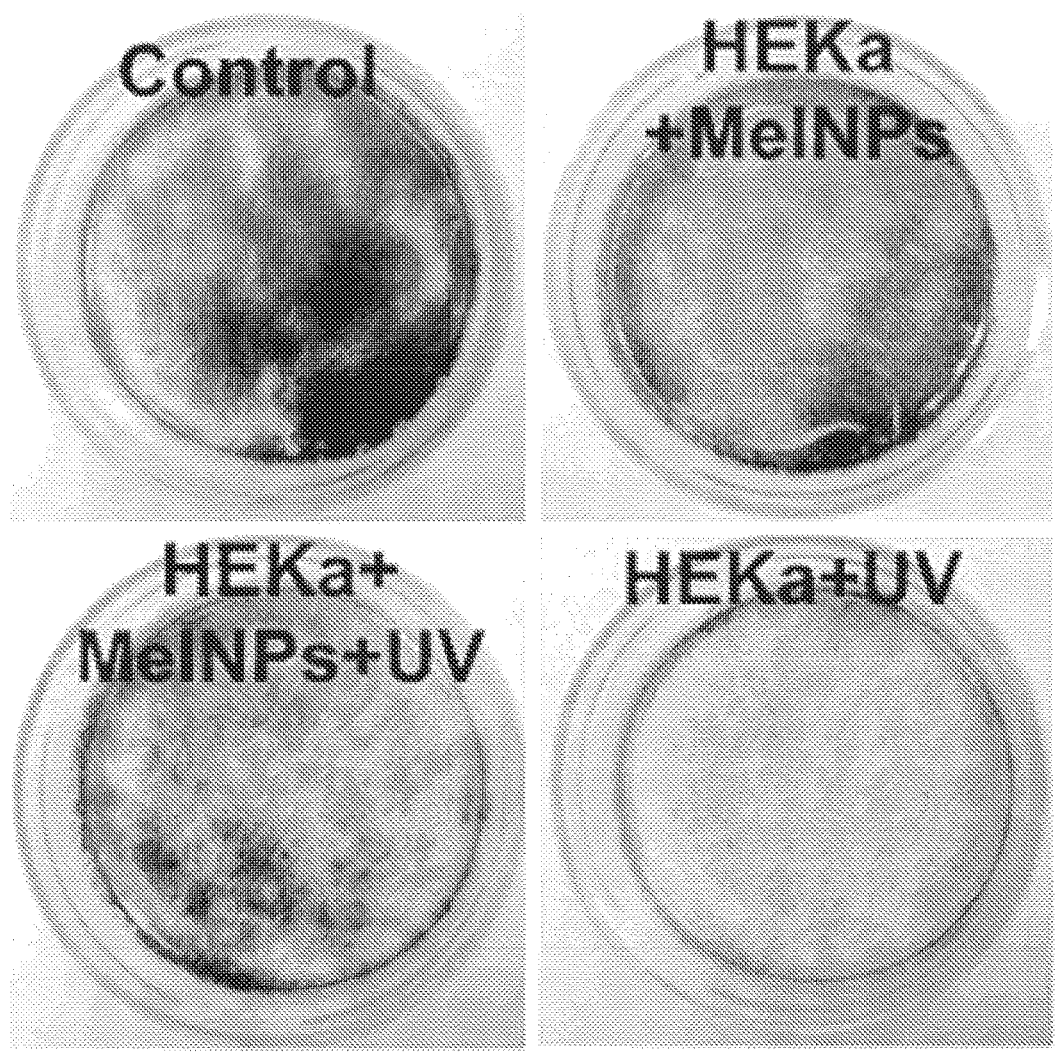
FIG. 14. Photos of crystal violet stained HEKa cells treated with or without MelNPs for 3 days, and with or without UV-irradiation. Control group was HEKa cells without UV and MelNPs treatment.

DNA damage is the predominant mode of damage caused by UV radiation. UV radiation induces two of the most abundant mutagenic and cytotoxic DNA lesions known; cyclobutane-pyrimidine dimers (CPDs) and 6-4 photoproducts (6-4PPs) and their Dewar valence isomers.[5,36] Therefore, we tested for protective qualities of MelNPs by analyzing DNA damage in HEKa cells after treatment with MelNPs followed by UV irradiation (FIG. 3). In mammalian cells, damage to genomic DNA can be lethal, inducing the formation of phosphorylated H2AX.[37] In our study, DNA damage was detected using a red fluorescent antibody (Alexa Fluor 555) against phosphorylated H2AX. At the same time, cell viability was investigated by Image-iT DEAD Green, which permeates when the plasma membrane is compromised. HEKa cells were treated for 5 min with UV light and subsequently cultured under normal conditions for 1 day. The results show HEKa cells suffering this treatment had dramatically increased DNA damage (red) and cell death (green), seen simultaneously (see FIG. 12 for controls, and magnified images in FIG. 13). By contrast, after incubating with MelNPs for 3 days, HEKa cells with the same 5 min UV irradiation and subsequent 24 hours incubation displayed no DNA damage and excellent viability (FIG. 3A, FIG. 3B, and FIG. 14). Therefore, the supranuclear artificial melanin caps are able to reduce damage from ultraviolet light in HEKa cells, similar to the performance of natural supranuclear melanin caps. [38]

We next assayed for reactive oxygen species (ROS) occurring in response to UV irradiation. Here, we used 2',7'-dichlorofluorescin diacetate (DCFH-DA), which exhibits green fluorescence under ROS activation as a ROS sensor.[39] Following UV irradiation, the level of green fluorescence in untreated HEKa cells is clearly higher than with MelNP treatment, confirming the protective qualities provided by artificial perinuclear cap formation (FIG. 4).

Accordingly, the melanin-like nanoparticles (MelNPs) according to the present disclosure were prepared by spontaneous oxidation of dopamine in alkaline solution to investigate their potential as artificial melanosomes. MelNPs were taken up by HEKa cells, followed by accumulation in patterns typical of so-called microparasols or perinuclear caps. This cellular distribution is similar to that observed for natural melanosomes occurring in human skin in vivo[8] observed in tissue culture of keratinocytes treated with extracted melanosomes, [31] and in co-cultures of melanocytes with keratinocytes.[24] Assays indicate that MelNPs are transported by similar pathways as natural melanosomes with subsequent degradation of MelNPs observed in ITEKa cells after incubating for 3 days to generate structures observed in natural systems. Finally, we demonstrated the UV photoprotective qualities of synthetic MelNPs. Considering limitations in the treatment of melanin-defective related diseases and the biocompatibility of these synthetic MelNPs in terms of uptake and degradation, these systems have potential as artificial melanosomes for the development of novel therapies, possibly supplementing the biological functions of natural melanins.

General Methods. All reagents were purchased as listed below and used without further purification. Dopamine hydrochloride, Triton X-100, Crystal violet and, 2',7'-dichlorofluorescin diacetate (DCFH-DA) were purchased from Sigma-Aldrich (St. Louis, MO). AuNPs were purchased from BBI Solutions (Cardiff, United Kingdom). EpiLife medium, HKGS growth supplement, Nucblue and LYSOTRACKER® Red DND-99 were purchased from Life Technologies (Carlsbad, CA). Mesothelial cell growth medium was purchased from Zen-Bio Inc. (Research Triangle Park, NC). Image-iT DEAD Green, Alexa Fluor 555, and Hoechst 33342 were purchased from Thermo Fisher Scientific (Waltham, MA). MALDI TOF-Mass Spectra were obtained on a Bruker Bifiex IV at the UCSD Chemistry and Biochemistry Molecular Mass Spectrometry Facility. Confocal Laser Scanning Microscopy images were obtained on an Olympus FV1000. Cell sectioning was performed by the UCSD School of Medicine Cellular & Molecular Medicine Electron Microscopy Core Facility. Cell Transmission Electron Microscopy (TEM) images were acquired on carbon grids (Ted Pella, Inc.) and obtained on a JEOL 1200 EX H TEM at 80 kV. All other TEM images were acquired on carbon grids (Ted Pella) and obtained on a FEI Tecnai G2 Sphera at 200 kV. FTIR spectra were obtained using a Thermo Scientific Nicoiet 6700. Optical density measurements were recorded using a Perkin Elmer EnSpire Multimode Plate Reader. Cells were irradiated at 365 nm using a hand held UV lamp (8W) (UVP, LLC). Dynamic Light Scattering (DLS) was performed on a DynaPro Nanostar (Wyatt Technology Corp.). Zeta-potentials were obtained on a Zetasizer Nano (Malvern Instruments Ltd.), Scanning Electron Microscopy (SEM) images were acquired using a FEI XL30 at 10 KV, and Energy-dispersive X-ray spectroscopy (EDX) was obtained by EDX Silicon Drift Deter (SDD) system on FEI XL30 in the Nano3 cleanroom at UCSD.

Synthesis of MelNPs. MelNPs were prepared by spontaneous oxidation of dopamine. Briefly, 40 mL 100% ethanol and 90 ml deionized water were mixed in a 250 mL round flask. 2 mL of a 28-30% $NH_4OH$ solution was added to the flask and stirred vigorously for 10 min to ensure adequate mixing. A dopamine hydrochloride solution of 400 mg dopamine hydrochloride (Sigma) in 10 mL deionized water was slowly added to the mixture, under vigorous stirring. The color of the solution turned to pale yellow as soon as the dopamine hydrochloride solution was added, and gradually changed to dark brown over the course of the reaction. After 8 h, MelNPs were retrieved by centrifugation (14000 rpm, 10 min) and washed with deionized water three times.

MALDI TOF-Mass Spectrum Measurement. MALDI measurements were performed on a Bruker Reflex time of flight instrument, operating in positive linear mode. Ionization was achieved with a pulsed UV laser beam (nitrogen laser, $\lambda=337$ nm) were accelerated to 15 keV, UV laser light (energy about 50 uJ) was focused onto the sample, using a focal diameter of about 100-300μιη. Synthetic MelNPs were suspended in double-distilled water to reach a final concentration of 1 mg/mL. This suspension was deposited on the stainless steel sample holder and air-dried. A saturated solution of the matrix (2,5-dihydroxybenzoinc acid, DUB) in 50/50 (v/v) water/acetonitrile was then added and allowed to air-dry before insertion into the mass spectrometer. Mass spectra were obtained by averaging the ions from 100 laser shots. Daily external calibration was provided by the [M+H] ions of angiotensin II (m/z 1046) and DUB (m/z 155). (FIG. 4A)

Confocal Laser Scanning Microscopy for Time-dependent Uptake in HEKa cells. HEKa ceils were plated and incubated overnight in 35 mm glass-bottom round dishes in a 5% $CO_2$ atmosphere at 37° C. using EpiLife medium with HKGS growth supplement (Life Technologies). 2 ml of a 0.02 mg/ml MelNPs suspension was added and incubated with the cells for either 4 hours, 1 day, 2 days or 3 days. After washing with PBS buffer, the cells were incubated with the nuclear stain Nucblue (Life Technologies) for 25 min and then fixed with a 4% paraformaldehyde solution for 20 min. Finally, the cells were washed with PBS and imaged by confocal microscopy. (FIG. 6)

Transmission Electron Microscopy for Concentration-dependent Uptake of MeNPs in HEKa cells. HEKa cells were plated in 35 mm round plastic dishes and incubated in a 5% $CO_2$ atmosphere at 37° C. using EpiLife medium with HKGS growth supplement (Life Technologies) until reaching ~80% confluency. Different concentrations of MelNPs in growth media were added and incubated for 4 hours. The cells were washed three times with PBS to remove free MelNPs, then fixed with 2% glutaraldehyde in 0.1 M sodium cacodylate buffer at pH=7.4 (SC buffer) on ice for more than 2 hours. After washing three times with 0.1 M SC buffer for 5 min, the cells were postfixed with 1% osmium tetroxide in 0.1 M SC buffer for 1 hour on ice. The cell pellets were washed 3 times with 0.1 M SC buffer for 5 min, followed by a quick rinse in distilled $H_2O$. Cell pellets were stained with 2% uranyi acetate (UA) for 1 hour on ice, then dehydrated in a graded series of ethanol (50%, 70%, 90% and 2 times 100%) for 5-8 min, and dried in acetone at room temperature. The cell pellets were infiltrated by a 50:50 dry acetone/DURCUPAN™ solution for 1-2 hours on a shaker, followed by 100% DURCUPAN™ overnight and two further treatments of 100% DURCUPAN™ the next day. Finally, cell pellets were embedded in DURCUPAN™ and incubated at 60° C. for 36-48 hours. Ultrathin sections (around 60 nm) were cut and examined by electron microscopy (FIG. 5).

Transmission Electron Microscopy for Time-dependent Uptake of MelNPs in HEKa cells. HEKa cells were plated in 35 mm round plastic dishes and incubated in a 5% $CO_2$ atmosphere at 37° C. using EpiLife medium with HKGS growth supplement (Life Technologies) until reaching ~80% confluency. Then 0.02 mg/mL MelNPs were added in medium and incubated for either 4 hours, 1 day, 2 days or 3 days. The cells were washed 3 times with PBS in order to remove excess MelNPs, and then fixed with SC buffer, on ice for more than 2 hours. After washing three times with 0.1 M SC buffer for 5 min, the cells were postfixed with 1% osmium tetroxide in 0.1 M SC buffer for 1 hour on ice. The cell pellets were washed with 0.1 M SC buffer three times for 5 min, followed by a quick rinse with distilled $H_2O$. The cell pellets were stained with 2% uranyi acetate for 1 hour on ice, then dehydrated in a graded series of ethanol (50%, 70%, 90% and 2 times 100%) for 5-8 rain, then dried in acetone at room temperature. The cell pellets were infiltrated by a 50:50 dry acetone/DURCUPAN™ solution for 1-2 hours on a shaker, followed by 100% DURCUPAN™ overnight and two further treatments of 100% DURCUPAN™ next day. Finally, cell pellets were embedded in DURCUPAN™ and incubated at 60° C. for 36-48 hours. Ultrathin sections (around 60 nm) were cut and were examined by electron microscopy. (FIG. 2 and FIG. 7)

Confocal Laser Scanning Microscopy for Time-dependent Uptake of MelNPs in MeT-5A cells. MeT-5A cells were plated in 35 mm round glass-bottom dishes in a 5% $CO_2$ atmosphere at 37° C. using EpiLife medium with HKGS growth supplement (Life Technologies) overnight. 2 mL of a 0.02 mg/mL MelNP suspension were added and incubated with the cells for either 4 hours, 1 day, 2 days or 3 days. After washing with PBS buffer, the cells were stained with the nuclear stain Nucbiue (Life Technologies) for 20 min. The cells were fixed with a 4% paraformaldehyde solution, then washed with PBS and imaged by confocal microscopy. (FIG. 9)

Transmission Electron Microscopy for Time-dependent Uptake of MelNPs in MeT-5A cells. MeT-5A cells were plated in 35 mm round plastic dishes and incubated in a 5% $CO_2$ atmosphere at 37° C. using mesothelial cell growth medium (Zen-Bio Inc.) until reaching −80% confluency. Then, 2 ml of a 0.02 mg/mL suspension of MelNPs were added to the medium for different time incubation (1 day, 2 days and 3 days). The cells were washed with PBS three times to remove free MelNPs, then were fixed with 2% glutaraidehyde in 0.1M sodium cacodylate buffer at pH=7.4 (SC buffer) on ice for more than 2 hours. After washing three times with 0.1M SC buffer for 5 min, the ceils were postfixed with 1% osmium tetroxide in 0.1M SC buffer for 1 hour on ice. The cell pellets were washed with 0.1M SC buffer 3 times for 5 min, followed by a quick rinse with distilled $H_2O$. The cell pellets were stained with 2% uranyl acetate (UA) for 1 hour on ice, then dehydrated in a graded series of ethanol (50%, 70%, 90% and 2 times 100%) for 5-8 min, and dried in acetone at room temperature. The, cell pellets were infiltrated by a 50:50 dry acetone/DURCUPAN™ solution for 1-2 hours on a shaker, followed by 100% DURCUPAN™ overnight and two treatments of 100% DURCUPAN™ the next day. Finally, cell pellets were embedded in DURCUPAN™ and incubated at 60° C. for 36-48 hours. Ultrathin sections (about 60 nm) were cut and examined by electron microscopy (FIG. 9).

Transmission Electron Microscopy for Time-dependent Uptake of AuNPs in HEKa cells. HEKa cells were plated in 35 mm round plastic dishes and incubated in a 5% $CO_2$ atmosphere at 37° C. using EpiLife medium with HKGS growth supplement until reaching −80% confluency. Then, AuNPs (BBI solutions) at a similar nanoparticle concentration to the MelNPs were added to the medium for different times (1 day, 2 days and 3 days). The cells were washed three times with PBS in order to remove excess AuNPs, then fixed with 0.1 M SC buffer for more than 2 hours on ice. After washing three times with 0.1 M SC buffer for 5 min, the cells were postfixed with 1% osmium tetroxide in 0.1 M SC buffer for 1 hour on ice. The cell pellets were washed with 0.1 M SC buffer three times for 5 min, followed by a quick rinse with distilled $H_2O$, then stained with 2% uranyl acetate for 1 hour on ice. After staining, the pellets were dehydrated in a graded series of ethanol (50%, 70%, 90% and 2 times 100%) for 5-8 min, and dried in acetone at room temperature. The cell pellets were infiltrated by a 50:50 dry acetone/DURCUPAN™ solution for 1-2 hours on a shaker, followed by 100% DURCUPAN™ overnight and two treatments of 100% DURCUPAN™ the next day. Finally, cell pellets were embedded in DURCUPAN™ and incubated at 60° C. for 36-48 hours. Ultrathin sections (around 60 nm) were cut and examined by electron microscopy. (FIG. 11).

Confocal Laser Scanning Microscopy for Colocalization of MelNPs and LYSOTRACKER®. HEKa cells were plated in 35 mm round glass-bottom dishes in a 5% CO) atmosphere at 37° C. using EpiLife medium with HKGS growth supplement (Life Technologies) overnight. 2 mL of a 0.02 mg/ml MelNP suspension was a incubated with the cells for either 4 hours, 1 day, 2 days or 3 days. After washing to remove free MelNPs the ceils were stained with the nuclear stain Nucblue (Life Technologies) and the lysosome stain LYSOTRACKER® Red DND-99 (Life Technologies), fixed with a 4% paraformaldehyde solution, washed with PBS, then imaged via confocal microscopy (FIG. 2).

Confocal Laser Scanning Microscopy for DNA Damage Stain. HEKa cells were plated in 35 mm round glass-bottom dishes in a 5% $CO_2$ atmosphere at 37° C. using EpiLife medium with HKGS growth supplement (Life Technologies) overnight. 2 mL of a 0.02 mg/mL MelNP suspension was incubated with the ceils for 3 days, after which they were washed with PBS buffer to remove free MeNPs. Cells, treated with and without MelNPs, were irradiated by UV for 5 min, then incubated under normal cell culture conditions for another 24 hours. To test cell viability, Image-iT DEAD Green (Thermo Fisher Scientific) was added to the cells and allowed to incubate for 30 min under normal cell culture conditions. The cells were then fixed in a 4% paraformaldehyde solution for 15 min, permeabilized by a Triton X-100 solution (15 ul in 6 ml PBS) for 15 min, and blocked by a BSA solution (0.25 g in 25 ml PBS) for 1 hour. Subsequently, a solution of the primary antibody pH2ax was added to the cells and incubated for 1 hour. The Alexa Fluor 555 conjugated secondary antibody/Hoechst 33342 nuclear counterstain (Thermo Fisher Scientific) (3 ul/1 ul respectively in 6 ml BSA blocking buffer) was added to the cells and incubated for another hour. Finally, the cells were washed with PBS buffer and imaged by confocal microscopy. (FIG. 3A and FIG. 13).

Crystal Violet Stain for HEKa cells. HEKa cells were plated in 35 mm round glass-bottom dishes in a 5% $CO_2$ atmosphere at 37° C. using Epilife medium with HKGS growth supplement (Life Technologies) overnight. 2 mL of a 0.02 mg/mL MeiNP suspension was incubated with the cells for 3 days, after which they were washed with PBS buffer to remove free MelNPs. Cells treated with and without MelNPs were irradiated by UV for 5 min, then incubated under normal cell culture conditions for another 24 hours. The ceils were fixed in a 4% paraformaldehyde solution for 15 min at room temperature, then stained with 0.1% w/v crystal violet for 20 min at room temperature. After pouring off the crystal violet solution, the cells were gently washed with deionized water until the water ran clear, then dried at room temperature overnight. 1 mL of 100% methanol was added to re-solubilize the cells, whose OD absorption at 540 nm was measured using a plate reader (FIG. 3B, FIG. 14).

Figure 12:
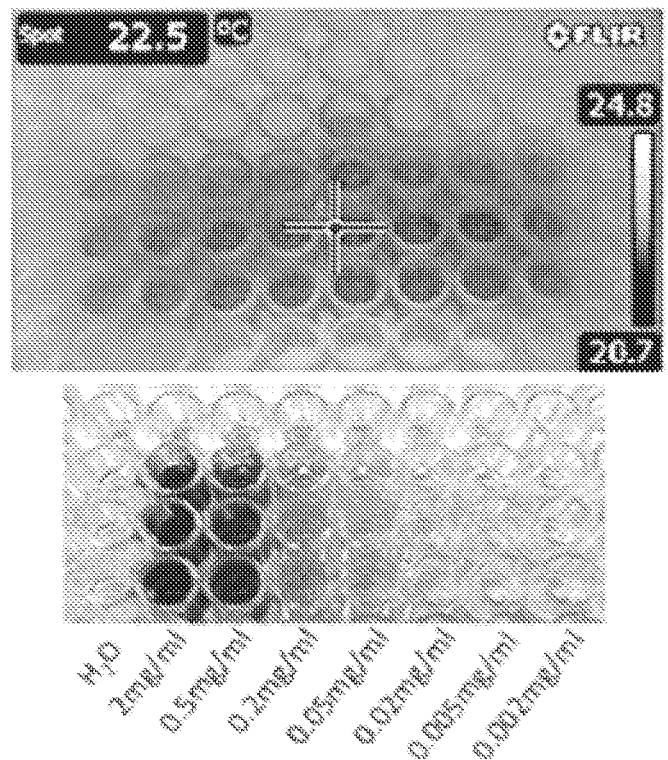
FIG. 12. IR image (top) of MelNP solutions over a 1000-fold concentration range (bottom) after irradiation at (wavelength) for 5 minutes. The uniform color shows that no heat is generated upon UV irradiation.

IR images for MelNPs with gradient concentrations. To test for the heat generation under UV-irradiation, aqueous solutions with a concentration range from 2 mg/mL to 0.002 mg/mL were prepared. These solutions were irradiated for 5 min. IR spectra were obtained immediately after UV irradiation. Pure distilled water was used as a reference (FIG. 12).

Confocal Laser Scanning Microscopy for ROS detection. HEKa cells were plated in 35 mm round glass-bottom dishes in a 5% $CO_2$ atmosphere at 37° C. using EpiLife medium with HKGS growth supplement (life Technologies) overnight. 2 nil. of a 0.02 mg/mL MelNP suspension was incubated with the ceils for 3 days. After washing with PBS buffer to remove free MelNPs, 2 ml 0.01 μM 2',7'-dichlorofluorescin diacetate (DCFH-DA) PBS solution was added to the cells and incubated for 20 min. After washing with PBS buffer, cells with and without treated MelNPs were irradiated by UV for 5 min, then stained by the nuclear stain Nucblue for 25 min at room temperature and fixed with a 4% paraformaldehyde solution for 20 rain at room temperature. The ceils were washed with PBS and imaged by confocal microscopy. (FIG. 4).

REFERENCES

[1] Ju, K.-Y. et al. Bio-Inspired, Melanin-Like Nanoparticles as a Highly Efficient Contrast Agent for T I-Weighted Magnetic Resonance Imaging. Biomacromolecules 14, 3491-3497 (2013); [2] Hunt, G. et al. Eumelanin and phaeomelanin contents of human epidermis and cultured melanocytes. Pigment Cell Res. 8, 202-208 (1995); [3] Ito, S. et al. Quantitative analysis of eumelanin and pheomelanin in humans, mice, and other animals: a comparative review. Pigment Cell Res. 16, 523-531 (2003); [4] Zucca, F. A. et al. Neuromelanin of the human substantia nigra: an update. Neurotox. Res. 25, 13-23 (2014); [5] Brenner, M. et al. The Protective Role of Melanin Against UV Damage in Human Skint. Photochem. Photobiol. 84, 539-549 (2008); [6] Taieb, A. et al. Melanins and Melanosomes: Biosynthesis, Biogenesis, Physiological, and Pathological Functions. Wiley-VCH Verlag GmbH & Co., Weinheim, (2011); [7] Wu, X. S. et al. Melanoregulin regulates a shedding mechanism that drives melanosome transfer from melanocytes to keratinocytes. Proc. Natl. Acad. Sci. 109, E2101-E2109 (2012); [8] Ando, H. et al. Melanosomes are transferred from melanocytes to keratinocytes through the processes of packaging, release, uptake, and dispersion. J. Invest. Dermatol. 132, 1222-1229 (2012); [9] Tadokoro, T. et al. UV-induced DNA damage and melanin content in human skin differing in racial/ethnic origin. FASEB J. 17, 1177-1179 (2003); [10] Jin, Y. et al. Genome-wide association analyses identify 13 new susceptibility loci for generalized vitili-go. Nat. Genet. 44, 676-680 (2012); [11] Alikhan, A. et al. Vitiligo: a comprehensive overview: part I. Introduction, epidemiology, quality of life, diagnosis, differential diagnosis, associations, histopathology, etiology, and work-up. J. Am. Acad. Dermatol. 65, 473-491 (2011); [12] Lee, H. et al. Retinal development in albinism: a prospective study using optical coherence tomography in infants and young children. Lancet. 385, 14 (2015); [13] Montoliu, L. et al. Increasing the complexity: new genes and new types of albinism. Pigment Cell Melanoma Res. 27, 11-18 (2014); [14] Ju, K. Y. et al. Bio-inspired Development of a Dual-Mode Nanoprobe for MRI and Raman Imaging. Small 11, 84-89 (2015); [15] Liu, Y. et al. Polydopamine and its derivative materials: synthesis and promising applications in energy, environmental, and biomedical fields. Chem. Rev. 114, 5057-5115 (2014); [16] Ju. K.-Y. et al. Bioinspired polymerization of dopamine to generate melanin-like nanoparticles having an excellent free-radical-scavenging property. Biomacromolecules 12, 625-632 (2011): [17] Ando, H. et al. Approaches to identify inhibitors of melanin biosynthesis via the quality control of tyrosinase. J. Invest. Dermatol. 127, 751-761 (2007); [18] Watt, A. A. et al. The supramolecular structure of melanin. Soft Matter 5, 3754-3760 (2009); [19] Yu, X. et al. Formation of polydopamine nanofibers with the aid of folic acid. Angew. Chem. Int. Ed. 53, 12600-12604 (2014); [20] Ochs, C. J. et al. Dopamine-mediated continuous assembly of biodegradable capsules. Chem. Mater. 23, 3141-3143 (2011): [21] Chen, X. et al. Engineering fluorescent poly (dopamine) capsules. Langmuir 30, 2921-2925 (2014); [22] Wogelius, R. et al. Trace metals as biomarkers for eumelanin pigment in the fossil record. Science 333, 1622-1626 (2011); [23] Xiao, M. et al. Bio-Inspired Structural Colors Produced via Self-Assembly of Synthetic Melanin Nano-particles. ACS nano 9, 5454-5460 (2015); [24] Kasraee, B. et al. Ebselen is a new skin depigmenting agent that inhibits melanin biosynthesis and melanosomal transfer. Exp. Dermatol. 19, 19-24 (2012); [25] Byers, H. R. et al. Requirement of dynactin p150Glued subunit for the functional integrity of the keratinocyte microparasol. J. Investi. Dermatol. 127, 1736-1744 (2007); [26] Meredith, P. et al. The physical and chemical properties of eumelanin. Pigment Cell Res. 19, 572-594 (2006); [27] Tran, M. L. et al. Chemical and structural disorder in eumelanins: a possible explanation for broadband absorbance. Biophys. J. 90, 743-752 (2006); [28] Strube, O. I. et al. Site-Specific In Situ Synthesis of Eumelanin Nanoparticles by an Enzymatic Autodeposition-like Process. Biomacromolecules. 16, 1608-1613 (2015); [29] Pezzella, A. et al. Identification of Partially Degraded Oligomers of 5, 6-Dihydroxyindole-2-carboxylic Acid in Sepia Melanin by Matrix-assisted Laser Desorption/Ionization Mass Spectrometry. Rapid Commun. Mass Spectrom. 11, 368-372 (1997); [30] Mutsaers, S. E. The mesothelial cell. Int. J. Biochem. Cell Biol. 36, 9-16 (2004); [31] Orlow, S. J. Melanosomes are specialized members of the lysosomal lineage of organelles. J. Invest. Dermatol. 105, 3-7 (1995); [32] Dell'angelica, E. C. et al. Lysosome-related organelles. FASEB J. 14, 1265-1278 (2000); [33] Scott, G. et al. Filopodia are conduits for melanosome transfer to keratinocytes. J. Cell Sci. 115, 1441-1451 (2002); [34] Raposo, G. et al. Melanosomes-dark organelles enlighten endosomal membrane transport. Nat. Rev. Mol. Cell Biol. 8, 786-797 (2007); [35] Marks, M. S. et al. The melanosome: membrane dynamics in black and white. Nat. Rev. Mol. Cell Biol. 2, 738-748 (2001); [36] Mouret, S. et al. Cyclobutane pyrimidine dimers are predominant DNA lesions in whole human skin exposed to UVA radiation. Proc. Natl. Acad. Sci. 103, 13765-13770 (2006); [37] Kim, S. et al. Development of a high-content screening method for chemicals modulating DNA damage response. J. Biomol. Screen. 16, 259-265 (2011): [38] Kobayashi, N. et al. Supranuclear melanin caps reduce ultraviolet induced DNA photoproducts in human epidermis. J. Invest. Dermatol. 110. 806-810 (1998); [39] Han, K. et al. Dual-Stage-Light-Guided Tumor Inhibition by Mitochondria-Targeted Photodynam-ic Therapy. Adv. Funct. Mater. 25, 2961-2971 (2015);

In view of the foregoing detailed description of preferred embodiments of the present disclosure, it readily will be understood by those persons skilled in the art that the present disclosure is susceptible to broad utility and application. While various aspects have been described in the context of screen shots, additional aspects, features, and methodologies of the present disclosure will be readily discernable therefrom. Many embodiments and adaptations of the present disclosure other than those herein described, as well as many variations, modifications, and equivalent arrangements and methodologies, will be apparent from or reasonably suggested by the present disclosure and the foregoing description thereof, without departing from the substance or scope of the present disclosure. Furthermore, any sequence(s) and/or temporal order of steps of various processes described and claimed herein are those considered to be the best mode contemplated for carrying out the present disclosure. It should also be understood that, although steps of various processes may be shown and described as being in a preferred sequence or temporal order, the steps of any such processes are not limited to being carried out in any particular sequence or order, absent a specific indication of such to achieve a particular intended result. In most cases, the steps of such processes may be carried out in various different sequences and orders, while still falling within the scope of the present inventions. In addition, some steps may be carried out simultaneously. Accordingly, while the present disclosure has been described herein in detail in relation to preferred embodiments, it is to be understood that this disclosure is only illustrative and exemplary of the present disclosure and is made merely for purposes of providing a full and enabling disclosure of the disclosure. The foregoing disclosure is not intended nor is to be construed to limit the present disclosure or otherwise to exclude any such other embodiments, adaptations, variations, modifications and equivalent arrangements, the present disclosure being limited only by the claims appended hereto and the equivalents thereof.

What is claimed is:

1. A method comprising:
   treating a melanin-defective disease in a subject in need thereof, wherein the subject has the melanin-defective disease, said step of treating comprising:
   administering to said subject a synthetic melanin-like nanoparticle, said synthetic melanin-like nanoparticle comprising one or more melanin polymers, wherein said synthetic melanin-like nanoparticle is capable of protecting cells of said subject from UV-induced damage to the cells' DNA;
   wherein said synthetic melanin-like nanoparticle is capable of functioning as a pigment for the protection of said cell from ultraviolet damage; and
   wherein the synthetic melanin-like nanoparticle is capable of forming a supranuclear cap in a keratinocyte cell when the nanoparticle is incubated with the keratinocyte cell.

2. The method of claim 1, wherein said synthetic melanin-like nanoparticle is biocompatible.

3. The method of claim 1, wherein said one or more melanin polymers of said synthetic melanin-like nanoparticle is not bound to, conjugated to, attached to, coated by, encompassed by or otherwise associated with a lipid or a proteinaceous lipid.

4. The method of claim 1, wherein said one or more melanin polymers is a fused ring melanin polymer comprising a plurality of fused ring heteroaryl monomers or a plurality of fused ring heterocycloalkyl monomers;
   and wherein said fused ring melanin polymer is a fused ring metal-binding melanin polymer.

5. The method of claim 4, wherein the metal component of said metal-binding melanin polymer is iron.

6. The method of claim 4, wherein said fused ring melanin polymers comprise a plurality of dopamine monomers selected from the group consisting of dihydroxydopamine monomers, 3,4-dihydroxydopamine monomers, dioxydopamine monomers and 3,4-dioxydopamine monomers.

7. The method of claim 4, wherein said fused ring heteroaryl monomers are substituted with one or more substituents selected from the group consisting of hydroxyl and carboxyl; and wherein said fused ring heterocycloalkyl monomers are substituted with one or more substituents selected from the group consisting of hydroxyl, carboxyl and oxy.

8. The method of claim 4, wherein said fused ring heteroaryl monomers and/or fused ring heterocycloalkyl monomers are selected from the group consisting of indole monomers, benzothiazine monomers and benzothiazole monomers.

9. The method of claim 8, wherein said indole monomers are selected from the group consisting of dihydroxyindole monomers, 5,6-dihydroxyindole (DHI) monomers, 5,6-dihydroxyindole-2-carboxylic acid monomers, dioxyindole monomers, 5,6-dioxyindole monomers, 5,6-dioxyindole-2-carboxylic acid monomers.

10. The method of claim 7, wherein said fused ring heteroaryl monomers are a 6,6-fused ring heteroaryl monomer, a 5,6-fused ring heteroaryl monomer or a 6,5-fused ring heteroaryl monomer; and wherein said fused ring heterocycloalkyl monomers are a 6,6-fused ring heterocycloalkyl monomer, a 5,6-fused ring heterocycloalkyl monomer or 6,5-fused ring heterocycloalkyl monomer.

11. The method of claim 4, wherein said fused ring heteroaryl monomers are dihydroxy fused ring heteroaryl monomers and wherein said fused ring heterocycloalkyl monomers are dihydroxy fused ring heterocycloalkyl monomers.

12. The method of claim 11, wherein said monomers are a catechol fused ring monomer comprising hydroxy substituents attached to adjacent carbons of a 6 membered ring of said catechol fused ring monomer.

13. The method of claim 1, wherein said melanin polymer results from spontaneous oxidation of a plurality of melanin monomers in an aqueous solution and under alkaline conditions.

14. The method of claim 1, wherein the said synthetic melanin-like nanoparticle comprises at least one axis having a dimension of from about 1 nm to about 1000 nm.

15. The method of claim 1, wherein said damage is DNA damage.

16. The method of claim 1, wherein said damage results from reactive oxygen species (ROS).

17. The method of claim 1, wherein said synthetic melanin-like nanoparticle forms part of a synthetic melanin-like nanoparticle composition wherein said synthetic melanin-like nanoparticle is present at a concentration of from about 0.01 mg/ml to about 1.0 mg/ml within said synthetic melanin-like nanoparticle composition.

18. The method of claim 1, wherein said melanin-defective disease is vitiligio, albinism, or skin cancer.

19. The method of claim 1, wherein said synthetic melanin-like nanoparticle is administered topically.

20. The method of claim 19, wherein said synthetic melanin-like nanoparticle is administered topically as a cream, gel, ointment, lotion, aerosol or liquid; or wherein said synthetic melanin-like nanoparticle is administered topically with a transdermal patch.

21. The method of claim 1, wherein said synthetic melanin-like nanoparticle is administered intravenously.

22. The method of claim 1, wherein said synthetic melanin-like nanoparticle is administered orally.

23. The method of claim 1, wherein said synthetic melanin-like nanoparticle is administered by injection.

24. The method of claim 23, wherein said injection is an intraocular injection or a localized injection.

25. The method of claim 1, wherein said synthetic melanin-like nanoparticle is administered prior to, simultaneous with, or subsequent to UV exposure.

26. The method of claim 1, wherein the step of administering comprises contacting a cell of the subject with the synthetic melanin-like nanoparticle; and wherein the method comprises protecting the cell of the subject from ultraviolet-induced damage to the cell's DNA.

27. The method of claim 1, wherein the method comprises forming the synthetic melanin-like nanoparticle via spontaneous oxidation of dopamine monomers under alkaline conditions in an aqueous solution.

28. The method of claim 26, wherein the step of contacting is performed under conditions suitable to afford uptake of the synthetic melanin nanoparticle into the cell, thereby protecting a cell's DNA from UV-induced damage.

29. The method of claim 28, wherein the synthetic melanin nanoparticle is taken up by the cell and transported intracellularly to the cell's perinuclear area.

30. The method of claim 28, wherein the step of contacting comprises contacting a cell with a composition having a plurality of the synthetic melanin-like nanoparticles; wherein at least a portion of the plurality of the synthetic melanin nanoparticles are taken up by the cell and form a supranuclear cap in the cell.

31. The method of claim 30, wherein the cell is alive after contacting the synthetic melanin nanoparticles for 3 days.

* * * * *